(12) United States Patent
Sakai

(10) Patent No.: US 10,638,916 B2
(45) Date of Patent: May 5, 2020

(54) ENDOSCOPE DEVICE

(71) Applicant: OLYMPUS CORPORATION, Tokyo (JP)

(72) Inventor: Hiroshi Sakai, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/388,946

(22) Filed: Apr. 19, 2019

(65) Prior Publication Data

US 2019/0320877 A1 Oct. 24, 2019

(30) Foreign Application Priority Data

Apr. 23, 2018 (JP) ................................ 2018-082652

(51) Int. Cl.
| | | |
|---|---|---|
| *A61B 1/045* | (2006.01) | |
| *A61B 1/00* | (2006.01) | |
| *G02B 23/24* | (2006.01) | |
| *A61B 1/06* | (2006.01) | |
| *H04N 5/225* | (2006.01) | |

(52) U.S. Cl.
CPC ...... *A61B 1/00009* (2013.01); *A61B 1/00045* (2013.01); *A61B 1/045* (2013.01); *A61B 1/0676* (2013.01); *G02B 23/2461* (2013.01); *A61B 1/00193* (2013.01); *H04N 2005/2255* (2013.01)

(58) Field of Classification Search
USPC ......................................................... 348/65
See application file for complete search history.

(56) References Cited

U.S. PATENT DOCUMENTS

| | | | | |
|---|---|---|---|---|
| 9,554,028 | B2* | 1/2017 | Ichikawa | G03B 15/00 |
| 2004/0186351 | A1* | 9/2004 | Imaizumi | A61B 1/00009 |
| | | | | 600/160 |
| 2010/0245551 | A1* | 9/2010 | Morita | A61B 1/00009 |
| | | | | 348/68 |
| 2018/0000330 | A1* | 1/2018 | Takeuchi | G02B 23/24 |
| 2018/0344136 | A1* | 12/2018 | Kikuchi | A61B 1/045 |
| 2019/0239725 | A1* | 8/2019 | Ogasawara | A61B 1/00163 |

FOREIGN PATENT DOCUMENTS

JP 2013-105078 A 5/2013

* cited by examiner

*Primary Examiner* — Behrooz M Senfi

(74) *Attorney, Agent, or Firm* — Scully, Scott, Murphy & Presser, P.C.

(57) ABSTRACT

In an endoscope device, a control unit brings an imaging device into an operation in a first read-out mode. In the first read-out mode, the imaging device reads out pixel signals from a plurality of pixels in a first time. After an instruction for the measurement of a subject is generated, the control unit brings the imaging device into an operation in a second read-out mode. In the second read-out mode, the imaging device reads out the pixel signals from the plurality of pixels in a second time. The second time is shorter than the first time. The control unit causes an imaging condition switching unit to switch imaging conditions on the basis of an operation of the imaging device in the second read-out mode.

20 Claims, 34 Drawing Sheets

|  | | OPTICAL PATH SWITCHING TIME [ms] |
|---|---|---|
| TEMPERATURE [°C] | t1 | 4 |
|  | t2 | 5 |
|  | t3 | 6 |

ENDOSCOPE DEVICE

BACKGROUND OF THE INVENTION

Field of the Invention

The present invention relates to an endoscope device.

Priority is claimed on Japanese Patent Application No. 2018-082652, filed Apr. 23, 2018, the content of which is incorporated herein by reference.

Description of Related Art

Industrial endoscopes are widely used for observing internal damage and corrosion in boilers, engines, turbines, chemical plants, and the like. When defects such as damage and corrosion are found, it is necessary to perform switching between countermeasure methods in accordance with a degree thereof. Thus, an industrial endoscope having a measurement function of measuring sizes of damage and corrosion has been developed.

An endoscope device disclosed in Japanese Unexamined Patent Application, First Publication No. 2013-105078 includes an optical system for causing two optical images of a subject to be formed in a common region of an imaging device. Light passing through two optical paths corresponding to two different viewpoints forms two optical images. Hereinafter, the two optical paths are referred to as a first optical path and a second optical path. The endoscope device includes an optical path switching means for performing switching between two optical paths. The endoscope device captures an optical image formed by only light passing through either one of the two optical paths.

The endoscope device performs switching between two imaging conditions and acquires two images. The light passing through the first optical path forms a first optical image. The first optical image is an optical image from a first viewpoint. The endoscope device generates a first image by capturing the first optical image. At this moment, the first imaging condition is implemented. Subsequently, optical paths are switched. The light passing through the second optical path forms a second optical image. The second optical image is an optical image from a second viewpoint. The endoscope device generates a second image by imaging the second optical image. At this moment, the second imaging condition is implemented. The endoscope device measures a shape of a subject using the principle of stereo measurement on the basis of parallaxes provided in the first image and the second image. The first image and the second image are images captured from viewpoints different from each other.

When the tip of the endoscope or the subject moves while the first image and the second image are acquired, a positional relationship between two viewpoints changes and a mismatch between a stereo measurement parameter (such as a baseline length) and positions of two viewpoints occurs. Therefore, the endoscope device cannot accurately measure the shape of the subject. The endoscope device disclosed in Japanese Unexamined Patent Application, First Publication No. 2013-105078 alternately acquires a first image and a second image. When the amount of position shift between two first images is less than a predetermined threshold value, the endoscope device determines that there is no movement of an endoscope tip (tip movement) or movement of a subject (tip movement) during a period in which two first images are acquired and performs a measurement process.

SUMMARY OF THE INVENTION

According to a first aspect of the present invention, an endoscope device includes an imaging device, an imaging condition switching unit, a measurement unit, and a control unit. The imaging device includes a plurality of pixels arranged in a matrix. The imaging device generates a pixel signal of each pixel based on an optical image of a subject in each frame period of a plurality of frame periods. The imaging device outputs an image in each frame period of the plurality of frame periods. The imaging device continuously scans all or some of a plurality of rows in an array of the plurality of pixels, for each row, in each frame period of the plurality of frame periods. The imaging device reads out the pixel signals from the pixels in all or some of the plurality of rows. The image is generated on the basis of the pixel signals generated in at least some of the plurality of pixels. The imaging condition switching unit switches between a plurality of imaging conditions so that the imaging device captures an image of the subject. The measurement unit executes measurement of the subject in measurement coordinates within the image on the basis of the images for at least two frame periods. The imaging device reads out the pixel signals from the pixels in all or some of the plurality of rows in a first time in a first read-out mode. The imaging device reads out the pixel signals from the pixels in all or some of the plurality of rows in a second time in a second read-out mode. The second time is shorter than the first time. The control unit brings the imaging device into an operation in the first read-out mode before an instruction for the measurement of the subject is generated. The control unit brings the imaging device into an operation in the second read-out mode after the instruction for the measurement of the subject is generated. The control unit causes the imaging condition switching unit to switch the imaging conditions on the basis of an operation of the imaging device in the second read-out mode. The imaging device operates in the second read-out mode while the imaging condition switching unit switches the imaging conditions.

According to a second aspect of the present invention, in the first aspect, a first size of the image may be larger than a second size of the image. The first size may be a size of the image based on the pixel signals which are read out in the first read-out mode by the imaging device. The second size may be a size of the image based on the pixel signals which are read out in the second read-out mode by the imaging device.

According to a third aspect of the present invention, in the second aspect, the control unit may control a read-out position on the basis of a position of the measurement coordinates. The read-out position may be a position of a row in which the imaging device reads out the pixel signals in the second read-out mode.

According to a fourth aspect of the present invention, in the third aspect, a first row number may be larger than a second row number. The first row number may be the number of rows in which the imaging device reads out the pixel signals in the first read-out mode. The second row number may be the number of rows in which the imaging device reads out the pixel signals in the second read-out mode.

According to a fifth aspect of the present invention, in the third aspect, the control unit may control a column number on the basis of the position of the measurement coordinates.

The column number may be the number of columns in which the imaging device reads out the pixel signals in the second read-out mode.

According to a sixth aspect of the present invention, in the fifth aspect, a first column number may be larger than a second column number. The first column number may be the number of columns in which the imaging device reads out the pixel signals in the first read-out mode. The second column number may be the number of columns in which the imaging device reads out the pixel signals in the second read-out mode.

According to a seventh aspect of the present invention, in the third aspect, the imaging device may read out the pixel signals from the pixels disposed in a measurement row in the second read-out mode. The measurement row may include the pixel corresponding to the measurement coordinates.

According to an eighth aspect of the present invention, in the seventh aspect, when the imaging device reads out the pixel signals from the pixels disposed in the measurement row in the second read-out mode, the control unit may cause the imaging condition switching unit to switch the imaging conditions.

According to a ninth aspect of the present invention, in the first aspect, a time period in which the pixel signals are read out from the pixels in each row of the plurality of rows may include a blanking time. The blanking time may be a time period from a timing at which read-out of the pixel signal is completed in one row to a timing at which read-out of the pixel signal is started in a row different from the one row. The blanking time when the imaging device reads out the pixel signals in the second read-out mode may be shorter than the blanking time when the imaging device reads out the pixel signals in the first read-out mode.

According to a tenth aspect of the present invention, in the first aspect, the control unit may equalize brightnesses of the images for at least two frame periods used in the measurement of the subject by the measurement unit.

According to an eleventh aspect of the present invention, in the first aspect, the measurement unit may execute the measurement on the basis of a first image and a second image. The first image may be generated on the basis of the pixel signals of the pixels exposed in a first exposure period. The second image may be generated on the basis of the pixel signals of the pixels exposed in a second exposure period. The first exposure period may include a timing at which the instruction for the measurement of the subject is generated. The second exposure period may be started after the imaging condition switching unit completes the switching between imaging conditions. The control unit may equalize a length of the first exposure period with a length of the second exposure period on the basis of the length of the second exposure period determined in advance.

According to a twelfth aspect of the present invention, in the first aspect, the measurement unit may execute the measurement on the basis of a first image and a second image. The first image may be generated on the basis of the pixel signals of the pixels exposed in a first exposure period. The second image may be generated on the basis of the pixel signals of the pixels exposed in a second exposure period. The first exposure period may include a timing at which the instruction for the measurement of the subject is generated. The second exposure period is started after the imaging condition switching unit completes the switching between imaging conditions. The control unit may equalize a length of the second exposure period with a length of the first exposure period on the basis of the length of the first exposure period.

According to a thirteenth aspect of the present invention, in the first aspect, the endoscope device may further include a light source that generates illumination light with which the subject is irradiated. The measurement unit may execute the measurement on the basis of a first image and a second image. The first image may be generated on the basis of the pixel signals of the pixels exposed in a first exposure period. The second image may be generated on the basis of the pixel signals of the pixels exposed in a second exposure period. The first exposure period may include a timing at which the instruction for the measurement of the subject is generated. The second exposure period may be started after the imaging condition switching unit completes the switching between imaging conditions. The light source may generate the illumination light in the first exposure period and the second exposure period. The control unit may control the amount of light of the light source in the second exposure period on the basis of brightness of the first image.

According to a fourteenth aspect of the present invention, in the first aspect, the control unit may control a row number on the basis of an estimated time. The estimated time may be a time period estimated in the switching between imaging conditions by the imaging condition switching unit. The row number may be the number of rows in which the imaging device reads out the pixel signals in the second read-out mode.

According to a fifteenth aspect of the present invention, in the fourteenth aspect, the endoscope device may further include a temperature detection unit that detects a temperature of the imaging condition switching unit. The control unit may control the row number on the basis of the temperature detected by the temperature detection unit.

According to a sixteenth aspect of the present invention, in the first aspect, the plurality of imaging conditions may include a first imaging condition and a second imaging condition. The first imaging condition and the second imaging condition may be different from each other. The control unit may control a third row number on the basis of a first estimated time. The first estimated time may be a time period estimated in the switching between imaging conditions from the first imaging condition to the second imaging condition by the imaging condition switching unit. The third row number may be the number of rows in which the imaging device reads out the pixel signals in the second read-out mode. The control unit may control a fourth row number on the basis of a second estimated time. The second estimated time may be a time period estimated in the switching between imaging conditions from the second imaging condition to the first imaging condition by the imaging condition switching unit. The fourth row number may be the number of rows in which the imaging device reads out the pixel signals in the second read-out mode.

According to a seventeenth aspect of the present invention, in the first aspect, the measurement unit may execute the measurement on the basis of the pixel signals of a measurement row in the image. The measurement row may include at least two rows which are continuous. Any one of the at least two rows may include the pixel corresponding to the measurement coordinates.

According to an eighteenth aspect of the present invention, in the first aspect, the imaging condition switching unit may set any one of a first optical path and a second optical path as an imaging optical path, to form only any one of a first optical image of the subject and a second optical image of the subject in an imaging region of the imaging device.

According to a nineteenth aspect of the present invention, in the first aspect, the imaging condition switching unit may include a light source that generates white light and pattern light The pattern light has a spatial structure in which a bright portion and a dark portion are included. The control unit may cause the imaging condition switching unit to switch a state of the light source from a first state to a second state. The first state may be a state in which the subject is irradiated with the white light. The second state may be a state in which the subject is irradiated with the pattern light. The imaging device may operate in the first read-out mode when the light source is in the first state. The imaging device may operate in the second read-out mode when the light source is in the second state.

According to a twentieth aspect of the present invention, in the first aspect, the images of the at least two frame periods may be generated on the basis of the pixel signals which are read out in the second read-out mode by the imaging device.

DETAILED DESCRIPTION OF THE INVENTION

Hereinafter, embodiments of the present invention will be described with reference to the drawings.

First Embodiment

Figure 1:
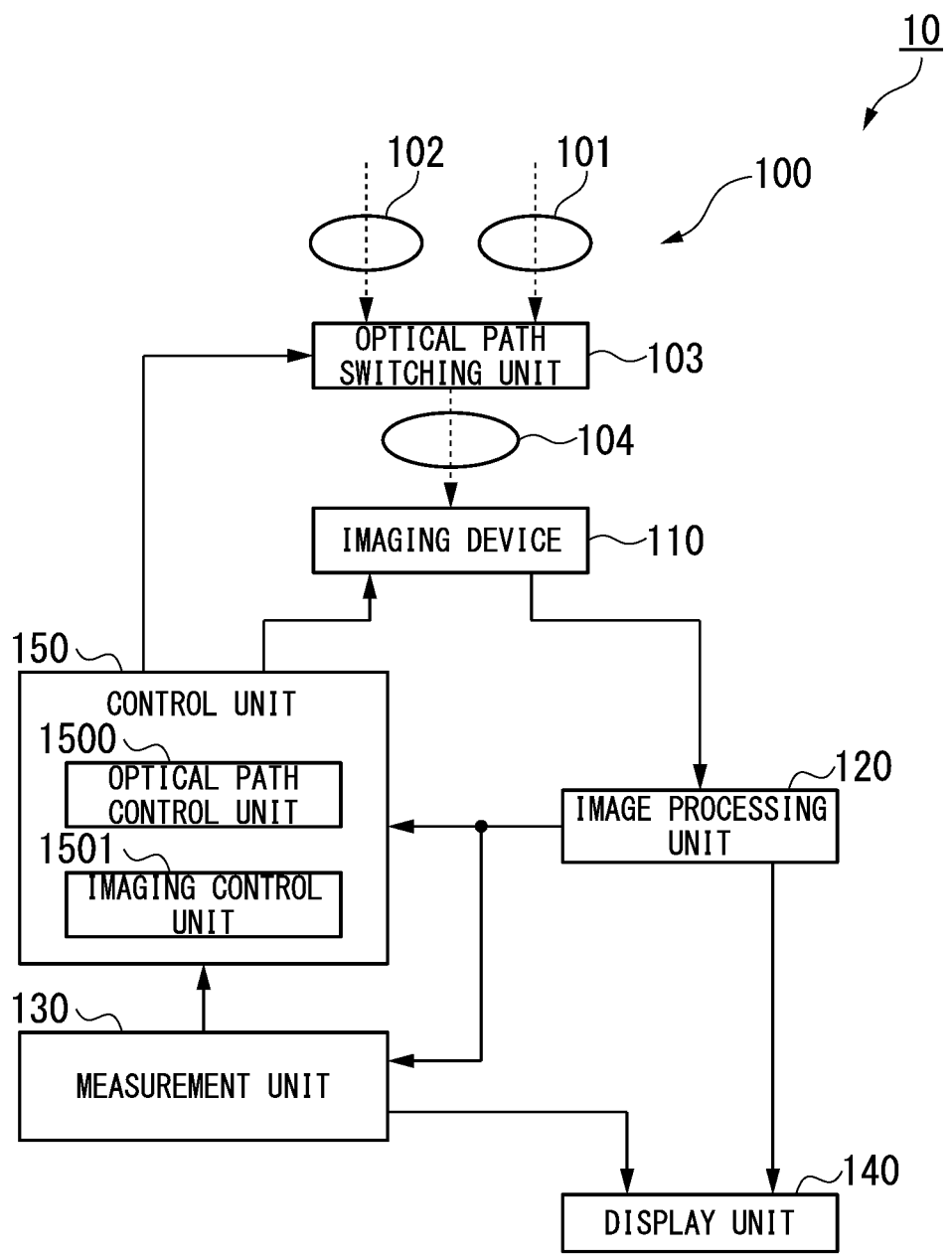
FIG. 1 is a block diagram showing a configuration according to an endoscope device of a first embodiment of the present invention.

A first embodiment of the present invention will be described below. FIG. 1 shows a configuration of an endoscope device 10 according to the first embodiment. The endoscope device 10 shown in FIG. 1 includes an optical system 100, an imaging device 110, an image processing unit 120, a measurement unit 130, a display unit 140, and a control unit 150. The optical system 100 includes a first optical system 101, a second optical system 102, an optical path switching unit 103 (imaging condition switching unit), and a third optical system 104.

Figure 3:
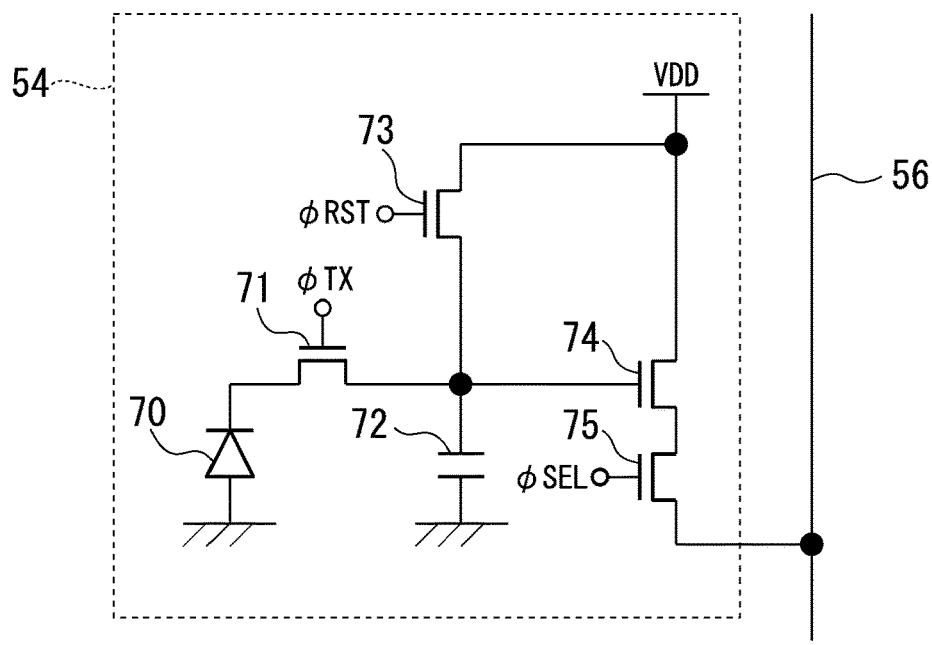
FIG. 3 is a circuit diagram showing a configuration of a pixel included in the imaging device according to the first embodiment of the present invention.

The schematic configuration of the endoscope device 10 will be described below. The imaging device 110 has a plurality of pixels 54 arranged in a matrix. The configuration of a pixel 54 is shown in FIG. 3. The configuration of the pixel 54 will be described later. The imaging device 110 generates a pixel signal of each pixel 54 based on the optical image of a subject in each frame period of a plurality of frame periods. The imaging device 110 outputs an image in each frame period of a plurality of frame periods. The imaging device 110 continuously scans all or some of a plurality of rows in the array of the plurality of pixels 54 for each row in each frame period of a plurality of frame periods. The imaging device 110 scans all or some of a plurality of rows, to thereby read out pixel signals from the pixels 54 in all or some of the plurality of rows. The image is generated on the basis of the pixel signals generated in at least some of the plurality of pixels 54. The optical path switching unit 103 switches between a plurality of imaging conditions so that the imaging device 110 captures an image of a subject. The measurement unit 130 executes the measurement of a subject in measurement coordinates within an image on the basis of the images in at least two frame periods.

In a first read-out mode, the imaging device 110 reads out the pixel signals from pixels 54 in all or some of a plurality of rows in a first time. In a second read-out mode, the imaging device 110 reads out the pixel signals from pixels 54 in all or some of a plurality of rows in a second time. The second time is shorter than the first time. Before an instruction for the measurement of a subject is generated, the control unit 150 brings the imaging device 110 into an operation in the first read-out mode. After the instruction for the measurement of a subject is generated, the control unit 150 brings the imaging device 110 into an operation in the second read-out mode.

The control unit 150 causes the optical path switching unit 103 to switch the imaging conditions on the basis of the operation of the imaging device 110 in the second read-out mode. While the optical path switching unit 103 switches the imaging conditions, the imaging device 110 reads out the pixel signals at a second frame rate. The images in at least two frame periods used in the measurement of a subject by the measurement unit 130 are generated on the basis of the pixel signals read out by the imaging device 110 in the second read-out mode. An image in at least one frame period used in the measurement of a subject by the measurement unit 130 is generated on the basis of the pixel signals read out from pixels 54 exposed between the read-out in the first read-out mode and the read-out in the second read-out mode. The image in at least one frame period used in the measurement of a subject by the measurement unit 130 is generated on the basis of the pixel signals read out from pixels 54 exposed after the read-out in the second read-out mode.

For example, when the imaging device 110 starts an operation in the second read-out mode, the control unit 150 causes the optical path switching unit 103 to switch the imaging conditions. Immediately after a timing at which the imaging device 110 starts the operation in the second read-out mode, the control unit 150 may cause the optical path switching unit 103 to switch the imaging conditions. Immediately before a timing at which the imaging device 110 starts the operation in the second read-out mode, the control unit 150 may cause the optical path switching unit 103 to switch the imaging conditions.

The detailed configuration of the endoscope device 10 will be described below. For example, the first optical system 101 and the second optical system 102 have a lens in which a concave lens and a convex lens are combined with each other. The optical axis of the second optical system 102 on the subject side is approximately parallel to the optical axis of the first optical system 101 on the subject side. The second optical system 102 has a parallax with respect to the first optical system 101. That is, the first optical system 101 and the second optical system 102 are separated from each other in a parallax direction. The parallax direction is a direction of a straight line passing through the optical center (principal point) of the first optical system 101 and the optical center (principal point) of the second optical system 102. The parallax direction is approximately orthogonal to the optical axis of each optical system. Light incident on the first optical system 101 passes through a first optical path. Light incident on the second optical system 102 passes through a second optical path different from the first optical path. The first optical system 101 forms a first optical image of the subject, and the second optical system 102 forms a second optical image of the subject.

The optical path switching unit 103 switches optical paths between the first optical path and the second optical path. The optical path switching unit 103 sets any one of the first optical path and the second optical path as an imaging optical path, to form only any one of the first optical image and the second optical image in an imaging region of the imaging device 110. The optical path switching unit 103 transmits only light passing through any one of the first optical path and the second optical path, and blocks light passing through the other.

For example, the optical path switching unit 103 includes a shutter (shielding plate) which is inserted into only any one of the first optical path and the second optical path. When the optical path switching unit 103 transmits the light of the first optical path, the shutter is inserted into the second optical path, and the light of the second optical path is blocked. When the optical path switching unit 103 transmits the light of the second optical path, the shutter is inserted into the first optical path, and the light of the first optical path is blocked. The operation of the optical path switching unit 103 is controlled by a control signal from the control unit 150. The optical path switching unit 103 may be a liquid crystal shutter including a polarizing plate and a liquid crystal cell. The optical path switching unit 103 is not limited to the above configuration.

The third optical system 104 forms a subject image based on any one of light having passed through the first optical path and light having passed through the second optical path in an imaging region of the imaging device 110. The subject image formed in the imaging region of the imaging device 110 is based on light having passed through only the optical path which is set as an imaging optical path between the first optical path and the second optical path.

The first optical image of the subject is formed on the basis of light having passed through the first optical path. The second optical image of the subject is formed on the basis of light having passed through the second optical path. The first optical image and the second optical image are incident on the imaging region of the imaging device 110. The imaging device 110 captures the first optical image and the second optical image. The imaging device 110 captures the first optical image formed by the first optical system 101 at a first imaging timing. The imaging device 110 captures the second optical image formed by the second optical system 102 at a second imaging timing. The first imaging timing and the second imaging timing are different from each other. The imaging device 110 generates a first image and a second image. The first image is generated on the basis of the first optical image formed in the imaging region. The second image is generated on the basis of the second optical image formed in the imaging region. The imaging device 110 outputs the first image and the second image to the image processing unit 120. The operation of the imaging device 110 is controlled in accordance with a command from the control unit 150.

The plurality of imaging conditions include a first imaging condition and a second imaging condition. The first imaging condition and the second imaging condition are different from each other. Under the first imaging condition, the first optical path is set as an imaging optical path. The imaging device 110 captures an image of a subject in the first imaging condition to thereby generate the first image of the subject. Under the second imaging condition, the second optical path is set as an imaging optical path. The imaging device 110 captures an image of a subject in the second imaging condition to thereby generate the second image of the subject.

The imaging device 110 is an XY-address scanning type complementary metal oxide semiconductor (CMOS) sensor. The imaging device 110 is driven by a rolling shutter system. In the rolling shutter system, pixel signals are sequentially read out from the pixels 54 for each row. Therefore, timings of exposure start for each pixel 54 are different from each other for each row. Hereinafter, the embodiment of the present invention will be described in an example in which a CMOS sensor (16×16 pixels, depth 10 bits) of a single-plate primary color Bayer array is used.

In the imaging device 110, an analog pixel signal is generated by photoelectric conversion. An analog front end (AFE) process is performed on the analog pixel signal by the imaging device 110. The AFE process includes correlated double sampling (CDS), analog gain control (AGC), analog-to-digital conversion (ADC), and the like. A circuit outside of the imaging device 110 may perform the AFE process. An image processed by the imaging device 110 is transferred to the image processing unit 120.

The image processing unit 120 executes image processing for display with respect to the image which is output from the imaging device 110. For example, the image processing executed by the image processing unit 120 includes at least one of optical black (OB) subtraction, pixel defect correction, white balance, colorization, a color correction process, a γ process, an enlargement process, a reduction process, and edge enhancement. An image on which these processes are performed is output to the display unit 140.

On the other hand, the image processing unit 120 executes image processing for measurement with respect to the image which is output from the imaging device 110. The image processing for measurement may be any process insofar as it is a process that makes it possible to generate an image appropriate for measurement. For example, an image having luminance, that is, a monochrome image can be used in measurement. The Bayer array has a structure in which a basic array is periodically arranged. The basic array includes respective pixels of R (red), Gr (green), Gb (green), and B (blue). For example, the image processing unit 120 may calculate luminance by adding pixel signals of four pixels within the basic array including a pixel of interest. Generally, the sensitivity of a green pixel is higher than the sensitivity of a red pixel and the sensitivity of a blue pixel. The image processing unit 120 may execute a white balance process by multiplying the pixel signal of a red pixel and the pixel signal of a blue pixel by a gain. An image on which a process for measurement is performed by the image processing unit 120 is output to the measurement unit 130.

The image processing unit 120 outputs a horizontal synchronizing signal and a vertical synchronizing signal, in addition to the image, to the measurement unit 130. The image processing unit 120 outputs a horizontal synchronizing signal and a vertical synchronizing signal to the control unit 150. The image processing unit 120 may include an image memory for adjusting the rate of imaging and the rate of display. A difference between the rate of imaging and the rate of display is alleviated by the image memory.

The measurement unit 130 executes the measurement of a subject in measurement coordinates by using the first image which is output from the imaging device 110 and the second image which is output from the imaging device 110. For example, the measurement result indicates a three-dimensional distance to the subject. For example, measurement coordinates (x, y) are set in an image out of the first image and the second image which corresponds to a right viewpoint. The measurement unit 130 compares the luminance profile of a line including the measurement coordinates in an image corresponding to a right viewpoint with the luminance profile of a line in an image corresponding to a left viewpoint. The measurement unit 130 detects the amount of deviation between two luminance profiles in units of pixels. The measurement unit 130 calculates a three-dimensional distance in the measurement coordinates on the basis of the detected amount of deviation. The measurement unit 130 outputs the measurement coordinates and a measurement result to the display unit 140. Before the measurement is executed, the measurement unit 130 outputs the measurement coordinates and a measurement trigger (TRG) to the control unit 150.

The display unit 140 is a transmissive liquid crystal display (LCD) requiring a backlight, an electro luminescence (EL) element (organic EL), or the like. The transmissive LCD is a display requiring a backlight. The EL element is a light-emission type display. For example, the display unit 140 is a transmissive LCD, and includes a drive unit required for LCD drive. The drive unit generates a drive signal, and drives an LCD on the basis of the drive signal. The display unit 140 displays an image processed by the image processing unit 120.

The control unit 150 includes an optical path control unit 1500 and an imaging control unit 1501. The control unit 150 controls the optical path switching unit 103 and the imaging device 110 on the basis of a synchronizing signal from the image processing unit 120. The optical path control unit 1500 controls the optical path switching unit 103. Specifically, the optical path control unit 1500 causes the optical path switching unit 103 to execute switching from the first optical path to the second optical path or switching from the second optical path to the first optical path in a time-division manner.

The imaging control unit 1501 controls the imaging device 110. Specifically, the imaging control unit 1501 controls an exposure time, a gain, an arithmetic operation relating to the gain, an image size, a read-out position, and the like. The image size is the size of an image which is output from the imaging device 110. The read-out position is the position of a row in which the imaging device 110 reads out the pixel signals. The imaging control unit 1501 has an arithmetic operation function. The imaging control unit 1501 calculates the image size on the basis of a time period required for the switching between optical paths. The imaging control unit 1501 calculates the read-out position on the basis of the measurement coordinates notified of by the measurement unit 130. When the measurement unit 130 outputs the measurement trigger to the control unit 150, an instruction for the measurement of a subject is generated. At this moment, the imaging control unit 1501 transmits a command for switching the operation mode of the imaging device 110 to the imaging device 110.

The image processing unit 120, the measurement unit 130, and the control unit 150 may be an application specific integrated circuit (ASIC), a field-programmable gate array (FPGA), a microprocessor, and the like. For example, the image processing unit 120, the measurement unit 130, and the control unit 150 are constituted by an ASIC and an embedded processor. The image processing unit 120, the measurement unit 130, and the control unit 150 may be constituted by other hardware, software, or firmware, or a combination thereof.

A computer of the endoscope device 10 may read a program and execute the read program. The program includes commands for specifying the operations of the image processing unit 120, the measurement unit 130, and the control unit 150. That is, the functions of the image processing unit 120, the measurement unit 130, and the control unit 150 may be realized by software. The program may be provided by a "computer readable recording medium" such as, for example, a flash memory. The program may be transmitted from a computer having the program held therein, through a transmission medium or through transmitted waves in the transmission medium, to the endoscope device 10. The "transmission medium" that transmits a program is a medium having a function of transmitting information. The medium having a function of transmitting information includes networks (communication networks) such as the Internet and communication channels (communication lines) such as a telephone line. The above-described program may realize a portion of the above-described functions. Further, the above-described program may be a difference file (difference program). The above-described function may be realized by a combination of a program which is already recorded in a computer and a difference program.

The endoscope device 10 has an insertion unit which is not shown in the drawing. The insertion unit is inserted into the inside of an object which is a target for observation and measurement. The optical system 100 and the imaging device 110 are disposed at the tip of the insertion unit. The tip of the insertion unit constitutes an endoscope.

Figure 2:
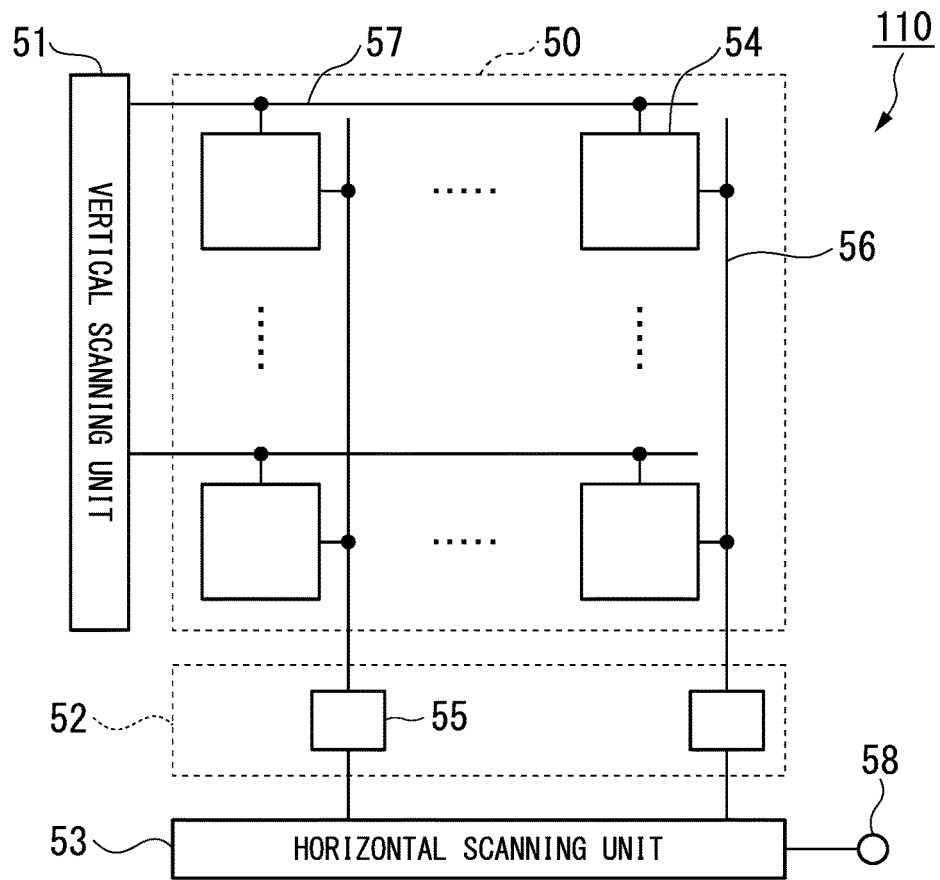
FIG. 2 is a block diagram showing a configuration of an imaging device according to the first embodiment of the present invention.

FIG. 2 shows a configuration of the imaging device 110. The imaging device 110 shown in FIG. 2 includes a pixel unit 50, a vertical scanning unit 51, a signal processing unit 52, and a horizontal scanning unit 53.

The pixel unit 50 has a plurality of pixels 54 arranged in a matrix. The plurality of pixels 54 are arranged in the imaging region of the imaging device 110. The number of rows and the number of columns in an array of the plurality of pixels 54 are two or more. The number of rows and the number of columns may not be the same as each other. Each pixel 54 of the plurality of pixels 54 generates a pixel signal in accordance with to the amount of light incident on the pixel 54. Each pixel 54 of the plurality of pixels 54 is connected to a vertical signal line 56. A plurality of vertical signal lines 56 are arranged. The plurality of vertical signal lines 56 are arranged for each column in the array of the plurality of pixels 54. Each pixel 54 of the plurality of pixels 54 outputs the generated pixel signal to the vertical signal line 56.

Each pixel 54 of the plurality of pixels 54 is connected to a control signal line 57. A plurality of control signal lines 57 are arranged. Each control signal line 57 of the plurality of control signal lines 57 is arranged for each row in the array of the plurality of pixels 54. Each control signal line 57 of the plurality of control signal lines 57 is connected to the vertical scanning unit 51. A control signal for controlling the operations of the plurality of pixels 54 is output from the vertical scanning unit 51 to the control signal line 57. A plurality of control signal lines 57 are arranged with respect to pixels 54 of one row. In FIG. 2, one control signal line 57 is shown with respect to pixels 54 of one row, and other control signal lines 57 are omitted. The details of the control signal will be described later.

The operations of the plurality of pixels 54 are controlled on the basis of the control signal which is output to the control signal line 57. The control signal corresponding to pixels 54 of one row is supplied in common to all the pixels 54 in the row. Therefore, the same operation timing is set with respect to two or more pixels 54 arranged in the same row. That is, two or more pixels 54 arranged in the same row operate simultaneously. The details of the configuration of the pixel 54 will be described later.

The control signal generated by the imaging control unit 1501 is transmitted to the imaging device 110. The vertical scanning unit 51 generates a control signal for controlling the operations of the plurality of pixels 54 on the basis of the control signal from the imaging control unit 1501. The vertical scanning unit 51 generates a control signal corresponding to each row of a plurality of rows in the array of the plurality of pixels 54. The vertical scanning unit 51 outputs the generated control signal to the control signal line 57.

The signal processing unit 52 includes a plurality of signal processing circuits 55. The signal processing circuits 55 are arranged for each column in array of the plurality of pixels 54. The signal processing circuit 55 is connected to the vertical signal line 56. The signal processing circuit 55 performs signal processing on a pixel signal which is output from the pixel 54 to the vertical signal line 56. The signal processing which is performed by the signal processing circuit 55 includes CDS, AGC and the like.

The pixel signal processed by the signal processing circuit 55 is input to the horizontal scanning unit 53. The horizontal scanning unit 53 sequentially selects columns in the array of the plurality of pixels 54. A pixel signal corresponding to a column selected by the horizontal scanning unit 53 is output from an output terminal 58.

The imaging device 110 includes the plurality of pixels 54 arranged in a matrix. The imaging device 110 generates a pixel signal of each pixel 54 based on the optical image of a subject in each frame period of a plurality of frame periods.

The imaging device 110 generates an image of the subject using the pixel signal in each frame period of a plurality of frame periods.

A frame is a set of a plurality of pixel signals included in one image. One image (one frame) is generated in one frame period. An imaging device 22 generates one image on the basis of pixel signals of one frame.

FIG. 3 shows a configuration of the pixel 54. The pixel 54 shown in FIG. 3 includes a photoelectric conversion unit 70, a charge transfer unit 71, a charge holding unit 72, a capacitor reset unit 73, an amplification unit 74, and an output unit 75. The photoelectric conversion unit 70 is a photodiode. The charge holding unit 72 is a capacitor. The charge transfer unit 71, the capacitor reset unit 73, the amplification unit 74, and the output unit 75 are transistors.

The photoelectric conversion unit 70 generates and accumulates electric charge in accordance with the amount of light incident on the pixel 54. The charge transfer unit 71 transfers the electric charge generated and accumulated by the photoelectric conversion unit 70 to the charge holding unit 72. The charge holding unit 72 holds the electric charge transferred from the photoelectric conversion unit 70. The capacitor reset unit 73 resets the electric charge of the charge holding unit 72 on the basis of a power supply voltage VDD. The capacitor reset unit 73 is turned on and therefore the capacitor reset unit 73 resets the electric charge of the charge holding unit 72. The amplification unit 74 amplifies a signal based on the electric charge held by the charge holding unit 72. The output unit 75 outputs the signal amplified by the amplification unit 74, as a pixel signal, to the vertical signal line 56.

The operation of the charge transfer unit 71 is controlled by a control signal φTX. The operation of the capacitor reset unit 73 is controlled by a control signal φRST. The operation of the output unit 75 is controlled by a control signal φSEL. The control signal φTX, the control signal φRST, and the control signal φSEL are supplied from the vertical scanning unit 51 through the control signal line 57.

The operation of the pixel 54 includes capacitor reset, charge transfer, and signal read-out. The capacitor reset corresponds to the operation of the capacitor reset unit 73. The charge transfer corresponds to the operation of the charge transfer unit 71. The signal read-out corresponds to the operation of the output unit 75. A period from an accumulation start timing to a transfer timing is a period (exposure period) in which exposure can be performed in the pixel 54. The accumulation start timing is a timing at which the photoelectric conversion unit 70 starts the generation of electric charge based on light incident on the pixel 54 and the accumulation of the electric charge. The transfer timing is a timing at which the charge transfer unit 71 transfers the electric charge accumulated in the photoelectric conversion unit 70 to the charge holding unit 72. In the exposure period, the photoelectric conversion unit 70 accumulates electric charge. In the following description, a state in which the pixel 54 is reset indicates a state of the pixel 54 at a timing when the exposure period ends, and the charge transfer unit 71 transfers the electric charge accumulated in the photoelectric conversion unit 70 to the charge holding unit 72.

The imaging device 110 outputs a pixel signal from the output unit 75, to thereby read out the pixel signal from the pixel 54. The imaging device 110 reads out the pixel signal from the pixel 54, to thereby acquire an image. The read-out of a pixel signal and the acquisition of an image are equivalent to each other.

Figure 4:
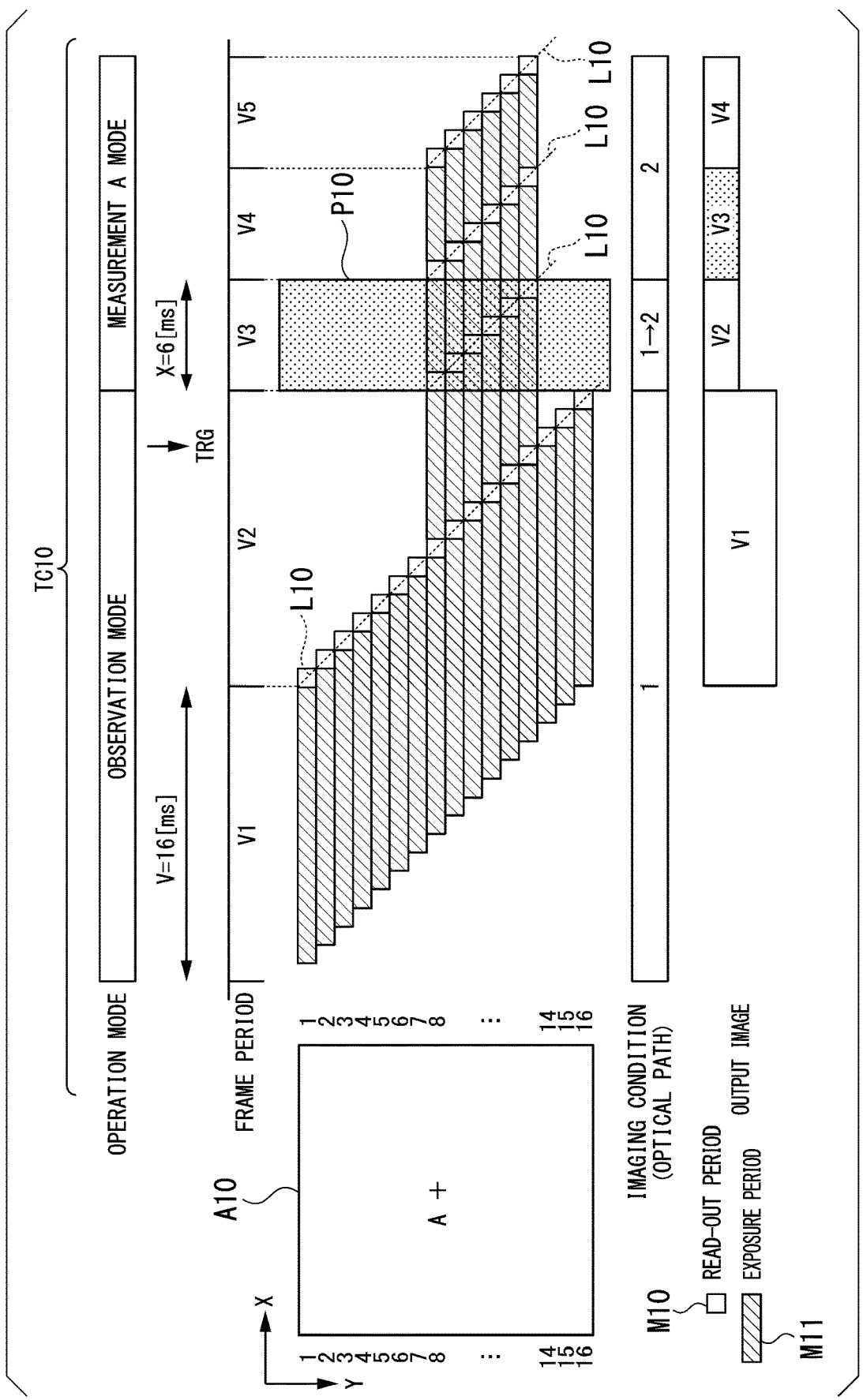
FIG. 4 is a timing chart showing an operation of the imaging device according to the first embodiment of the present invention.

FIG. 4 shows an operation of the imaging device 110. The operation of the imaging device 110 will be described with reference to FIG. 4. In the example shown in FIG. 4, measurement coordinates A are set substantially in the center of an imaging region A10. In the first embodiment, the position of the measurement coordinates A is determined in advance. The position of the measurement coordinates A is not limited to the center of the imaging region A10. In the example shown in FIG. 4, the imaging region A10 has sixteen rows. A pixel 54 located at the position of the measurement coordinates A is disposed in the eighth row of the imaging region A10. The number of rows of the imaging region A10 is not limited to sixteen.

A timing chart TC10 shows the operation of the imaging device 110. In the timing chart TC10, the horizontal direction represents time, and the vertical direction represents the row position of the pixel 54. The uppermost row is a first row, and the lowermost row is a sixteenth row.

In FIG. 4, frame periods are shown. Each of the frame periods includes an exposure period and a read-out period. In the read-out period, the pixel signal of the pixel 54 is read out. The read-out of the pixel signal includes charge transfer and signal read-out. Frame periods based on the start timing of a read-out period in pixels 54 of the first row are shown. A read-out period before one frame in a frame period V1 is not shown in FIG. 4. The frame periods from the second row to the sixteenth row are started later than the frame period of each row one level up by a predetermined time period. A pixel signal accumulated in a pixel 54 in the exposure period of a frame period Vn is read out from the pixel 54 in the read-out period of a frame period V(n+1).

Broken lines L10 in FIG. 4 indicate the start timing of a frame period of each row. The broken line L10 is used in common in all the timing charts including the timing chart TC10. The meaning of the broken line L10 is common in the present specification. A sign M10 in FIG. 4 indicates a read-out period. A sign M11 in FIG. 4 indicates an exposure period. The sign M10 and the sign M11 are omitted in timing charts other than the timing chart TC10, but each meaning of the sign M10 and the sign M11 is common in the present specification.

The imaging device 110 operates in an observation mode in the frame period V1. In the frame period V1, the imaging condition of the imaging device 110 is the first imaging condition. Therefore, the first optical path is set as an imaging optical path. In the example shown in FIG. 4, the length of a frame period in the observation mode is sixteen milliseconds. In an operation in each frame period in the observation mode, a time period (first time) required for the read-out of pixel signals of all the pixels 54 is sixteen milliseconds.

In a case where the exposure time is set to sixteen milliseconds, the start timing of the exposure period of the frame period V1 is the same as a timing at which the read-out of a pixel signal in a frame period previous to the frame period V1 is completed. In the start timing of the exposure period, the pixels 54 of the first row are reset. Thereby, the exposure period of the pixels 54 of the first row are started. In the exposure period, a signal based on light incident on the pixel 54 is accumulated in the pixel 54. After the exposure period of the pixels 54 of the first row are started, the exposure period of the pixels 54 of the second row are started. Similarly, the exposure periods of the pixels 54 from the third row to the sixteenth row are sequentially started.

The vertical scanning unit 51 sequentially generates a control signal of each row, and sequentially outputs the generated control signal to the pixels 54 of each row. The imaging device 110 continuously scans the pixels 54 of a plurality of rows for each row on the basis of the control signal which is sequentially output from the vertical scanning unit 51. The imaging device 110 sequentially starts the exposure periods of the pixels 54 of a plurality of rows through this scanning The pixel signals generated in the exposure period of the pixels 54 of each row in the frame period V1 are read out in a frame period V2. When the exposure period of the pixels 54 of the first row ends, the read-out period of the pixels 54 of the first row is started. The pixels 54 of the first row output the pixel signals to the vertical signal lines 56. When a predetermined time period has elapsed from a timing at which the read-out period of the pixels 54 of the first row is started, the read-out period of the pixels 54 of the first row ends. At this moment, the pixels 54 of the first row are reset, and the exposure period of the pixels 54 of the first row in the frame period V2 is started.

When the read-out period of the pixels 54 of the first row ends, the read-out period of the pixels 54 of the second row is started. The pixels 54 of the second row output the pixel signals to the vertical signal lines 56. When a predetermined time period has elapsed from a timing at which the read-out period of the pixels 54 of the second row is started, the read-out period of the pixels 54 of the second row ends. At this moment, the pixels 54 of the second row are reset, and the exposure period of the pixels 54 of the second row in the frame period V2 is started. Similarly, the read-out periods of the pixels 54 from the third row to the sixteenth row are sequentially started, and the pixel signals of the pixels 54 from the third row to the sixteenth row are sequentially read out. The pixels 54 from the third row to the sixteenth row are sequentially reset, and the exposure periods of the pixels 54 of the third row to the sixteenth row in the frame period V2 are sequentially started.

The vertical scanning unit 51 sequentially generates a control signal of each row, and sequentially outputs the generated control signal to the pixels 54 of each row. The imaging device 110 continuously scans the pixels 54 of a plurality of rows for each row on the basis of the control signal which is sequentially output from the vertical scanning unit 51. The imaging device 110 sequentially reads out the pixel signals of the pixels 54 of a plurality of rows through this scanning.

The imaging control unit 1501 brings the imaging device 110 into an operation in the observation mode (first read-out mode) in the frame period V1. In the observation mode, the imaging device 110 sequentially scans sixteen rows, and sequentially reads out the pixel signals from the pixels 54 of each row. The imaging device 110 outputs the first image at a first frame rate. The first image includes the pixel signals which are read out from the pixels 54 of sixteen rows.

In the rolling shutter system, rows to be read out are changed row by row, and the pixel signals are read out continuously from the pixels 54 of each row. In the rolling shutter system, an exposure period is sequentially started for each row, and a pixel signal is sequentially read out for each row. The pixels 54 of a row in which the read-out of the pixel signal is completed are reset, and the exposure period is resumed.

In FIG. 4, the operation of a frame period before the frame period V1 is not shown. In each frame period before the frame period V1, the same operation as the operation in the frame period V1 is executed.

A measurement trigger (TRG) is generated within a period in which the pixel signals generated in the exposure period of the pixels 54 of each row in the frame period V1 are read out. That is, a measurement trigger is generated within a read-out period in the frame period V2. When the read-out period of the pixels 54 of the sixteenth row in the frame period V2 ends, the read-out of the pixel signals generated in the exposure period of the pixels 54 of each row in the frame period V2 is started. Before a measurement trigger is generated, the read-out of a pixel signal in each frame period is executed in order from the first row. In a case where the measurement trigger is generated, a row in which the read-out of a pixel signal is started is changed. Specifically, the pixel signals of the pixels 54 of the eighth row in which the pixel 54 corresponding to the measurement coordinates A is disposed are initially read out.

The pixel signals generated in the exposure period of the pixels 54 of each row in the frame period V2 are read out in a frame period V3. The read-out period of the pixels 54 of the sixteenth row in the frame period V2 ends. At this moment, the exposure period of the pixels 54 of the eighth row in the frame period V2 ends, and the read-out period of the pixels 54 of the eighth row in the frame period V3 is started. The imaging control unit 1501 brings the imaging device 110 into an operation in a measurement A mode (second read-out mode). The imaging control unit 1501 outputs a command for switching the operation mode of the imaging device 110 from the observation mode to the measurement A mode to the imaging device 110. The imaging device 110 starts its operation in the measurement A mode on the basis of the command from the imaging control unit 1501. In the measurement A mode, the imaging device 110 sequentially scans six rows, and sequentially reads out the pixel signals from the pixels 54 of each row. The imaging device 110 outputs the second image at the second frame rate. The second image includes the pixel signals which are read out from the pixels 54 of six rows. The second frame rate is higher than the first frame rate in the observation mode.

Since a row in which the read-out of a pixel signal is started is changed in the frame period V3, the exposure period of the pixels 54 of the eighth row in the frame period V2 becomes shorter than the exposure period of the pixels 54 of the eighth row in the frame period V1. The length of the exposure period of the pixels 54 of each row in the frame period V2 is based on the position of a row in which a pixel signal is initially read out in the frame period V3. That is, the length of the exposure period of the pixels 54 of each row in the frame period V2 is based on the position of a row in which the pixel 54 corresponding to the measurement coordinates A is disposed.

When the read-out period of the pixels 54 of the eighth row in the frame period V3 is started, switching between imaging conditions, that is, switching between imaging optical paths is started. The imaging control unit 1501 outputs a control signal for the switching between imaging optical paths to the optical path switching unit 103. Thereby, the optical path control unit 1500 causes the optical path switching unit 103 to switch imaging optical paths. The optical path switching unit 103 starts switching from the first optical path to the second optical path on the basis of the control signal from the imaging control unit 1501. When the frame period V3 subsequent to the frame period V2 in which the measurement trigger is generated is started, the optical path switching unit 103 starts switching between imaging optical paths.

In the read-out period of the pixels 54 of the eighth row in the frame period V3, the pixels 54 of the eighth row output the pixel signals to the vertical signal lines 56. When a predetermined time period has elapsed from a timing at which the read-out period of the pixels 54 of the eighth row is started, the read-out period of the pixels 54 of the eighth row ends. At this moment, the pixels 54 of the eighth row are reset, and the exposure period of the pixels 54 of the eighth row in the frame period V3 is started.

In FIG. 4, a switching period P10 is shown. The switching period P10 is a period from the start of switching between optical paths to the completion of switching between optical paths. For example, six milliseconds are required for the switching between imaging optical paths. The length of the switching period P10 is shorter than the length of a frame period in the observation mode. The imaging control unit 1501 causes the imaging device 110 to read out the pixel signals from the pixels 54 of six rows in the switching period P10. In the switching period P10, the imaging device 110 sequentially starts the read-out periods of the pixels 54 of the eighth row to the thirteenth row, and sequentially reads out the pixel signals of the pixels 54 of the eighth row to the thirteenth row. The pixels 54 of the eighth row to the thirteenth row are sequentially reset, and the exposure periods of the pixels 54 of the eighth row to the thirteenth row in the frame period V3 are sequentially started.

The pixel signals generated in the exposure period of the pixels 54 of each row in the frame period V3 are read out in a frame period V4. The read-out period of the pixels 54 of the thirteenth row in the frame period V3 ends. At this moment, the exposure period of the pixels 54 of the eighth row in the frame period V3 ends, and the read-out period of the pixels 54 of the eighth row in the frame period V4 is started. At this moment, switching between imaging conditions, that is, switching between imaging optical paths is completed. The imaging optical path is the second optical path. The imaging device 110 sequentially starts the read-out periods of the pixels 54 of the eighth row to the thirteenth row, and sequentially reads out the pixel signals of the pixels 54 of the eighth row to the thirteenth row. An operation in which the imaging device 110 reads out the pixel signals in the frame period V4 is the same as the operation in which the imaging device 110 reads out the pixel signals in the frame period V3. In the frame period V4 and a frame period V5, the imaging device 110 continues the same operation as the operation for the frame period V3.

In the example shown in FIG. 4, the length of a frame period in the measurement A mode is six milliseconds. In the operation for each frame period in the measurement A mode, a time period (second time) required for the read-out of the pixel signals of the pixels 54 of the eighth row to the thirteenth row is six milliseconds.

In the measurement A mode, pixel signals are not read out from the pixels 54 of the first row to the seventh row and the fourteenth row to the sixteenth row. Rows to be read out are the eighth row to the thirteenth row. In FIG. 4, the exposure periods of the pixels 54 of rows other than the rows to be read out are not shown.

In FIG. 4, an image (output image) which is output from the imaging device 110 is schematically shown. An image V1 includes the pixel signals which are read out from the pixels 54 of sixteen rows after the exposure period in the frame period V1. The image V1 includes the pixel signals which are read out in the observation mode by the imaging device 110. An image V2 includes the pixel signals which are read out from the pixels 54 of six rows after the exposure period in the frame period V2. The image V2 includes the pixel signals which are read out in the measurement A mode by the imaging device 110. The sizes of an image V3 and an image V4 are the same as the size of the image V2.

Figure 5:
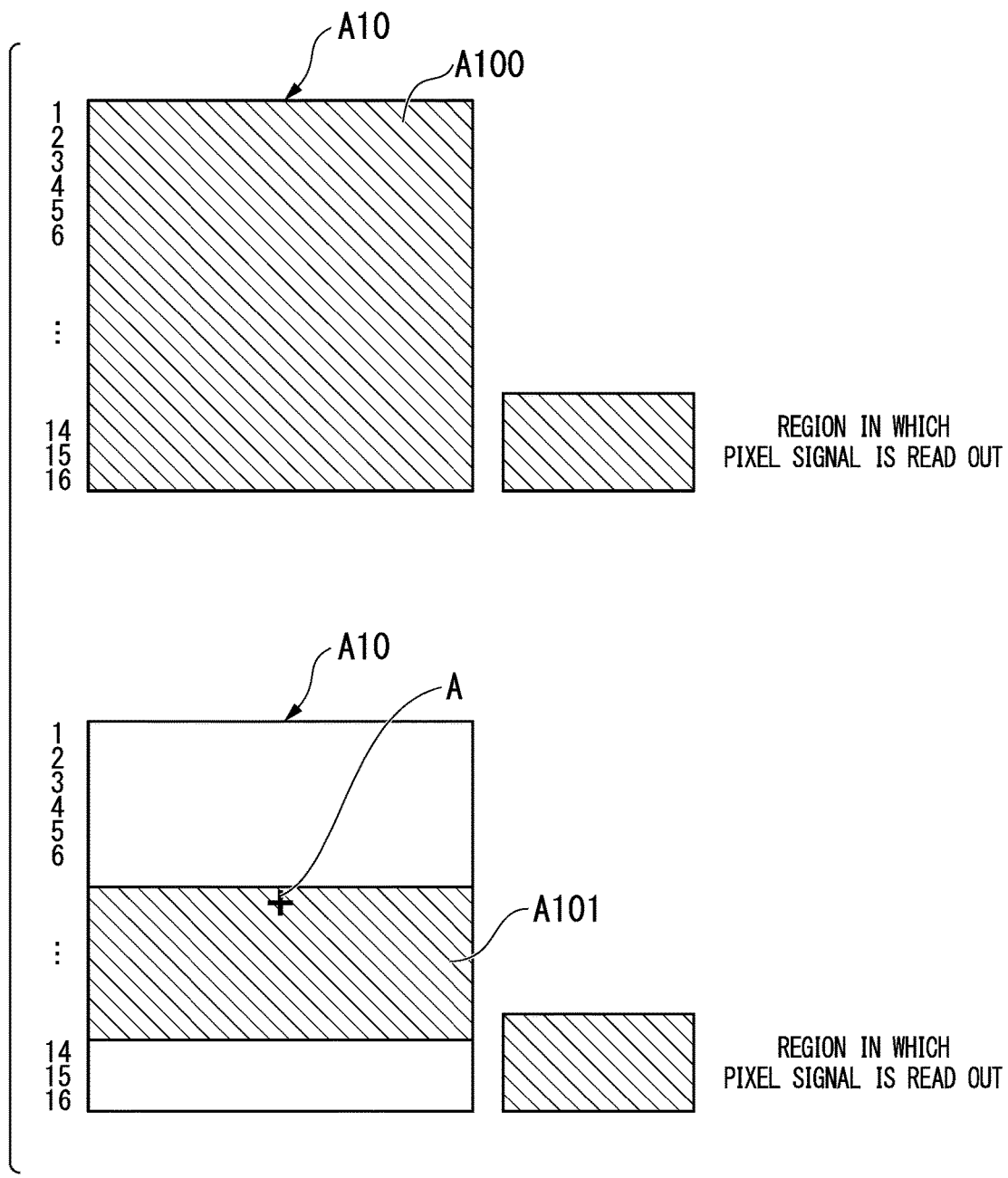
FIG. 5 is a diagram showing a region in which a pixel signal is read out in the first embodiment of the present invention.

FIG. 5 shows a region in which a pixel signal is read out in the imaging region A10. The pixels 54 in which the imaging device 110 reads out the pixel signals in the observation mode are disposed in a region A100. The region A100 includes the pixels 54 of the first row to the sixteenth row. The pixels 54 in which the imaging device 110 reads out the pixel signals in the measurement A mode are disposed in a region A101. The region A101 includes the pixels 54 of the eighth row to the thirteenth row. The pixel 54 corresponding to the measurement coordinates A is disposed in the eighth row.

The image V1 shown in FIG. 4 includes the pixel signals which are read out from the pixels 54 of the region A100 shown in FIG. 5. The image V1 includes the pixel signals which are read out from the pixels 54 of sixteen rows. The image V2, the image V3, and the image V4 shown in FIG. 4 include pixel signals which are read out from the pixels 54 of the region A101 shown in FIG. 5. The image V2, the image V3, and the image V4 includes the pixel signals which are read out from the pixels 54 of six rows.

A first size of the image is larger than a second size of the image. The first size is the size of an image based on the pixel signals which are read out in the observation mode by the imaging device 110. The second size is the size of an image based on the pixel signals which are read out in the measurement A mode by the imaging device 110. In the examples shown in FIGS. 4 and 5, the first size of the image is 16×16. In the examples shown in FIGS. 4 and 5, the second size of the image is 16×6.

After switching between imaging conditions, that is, imaging optical paths is started, the number of rows in which the imaging device 110 reads out the pixel signals decreases. Therefore, the time interval of imaging becomes shorter, and an interval at which the imaging device 110 outputs an image becomes shorter. The frame period in the measurement A mode is shorter than the frame period in the observation mode. The frame period in the measurement A mode is the same as the length of the switching period P10. In the example shown in FIG. 4, the frame period in the measurement A mode is six milliseconds. The frame period in the measurement A mode may be longer than the length of the switching period P10, and be shorter than in the frame period in the observation mode.

The imaging control unit 1501 controls a read-out position on the basis of the position of measurement coordinates. The read-out position is the position of a row in which the imaging device 110 reads out the pixel signals in the measurement A mode. In the example shown in FIG. 4, the imaging device 110 initially reads out the pixel signals from the pixels 54 disposed in a measurement row in the measurement A mode. The measurement row includes a pixel 54 corresponding to the measurement coordinates. In the example shown in FIG. 4, the pixel 54 corresponding to the measurement coordinates A is disposed in the eighth row. Therefore, the imaging device 110 initially reads out the pixel signals from the pixels 54 of the eighth row in the measurement A mode.

When the imaging device 110 reads out the pixel signals from the pixels 54 disposed in the measurement row in the measurement A mode, the optical path control unit 1500 causes the optical path switching unit 103 to switch imaging conditions. In the example shown in FIG. 4, after the imaging device 110 reads out the pixel signals from the pixels 54 of the eighth row in the measurement A mode, the imaging conditions are switched.

The first row number is larger than the second row number. The first row number is the number of rows in which the imaging device 110 reads out the pixel signals in the observation mode. The second row number is the number of rows in which the imaging device 110 reads out the pixel signals in the measurement A mode. In the examples shown in FIGS. 4 and 5, the first row number is sixteen. In the examples shown in FIGS. 4 and 5, the second row number is six.

The imaging control unit 1501 determines the size of the image on the basis of the length of the switching period P10 shown in FIG. 4. In a case where the measurement trigger is generated, the size of the image decreases. That is, the number of rows in which the imaging device 110 reads out the pixel signals decreases.

The imaging control unit 1501 controls a row number on the basis of an estimated time. The estimated time is a time period estimated in the switching between imaging optical paths by the optical path switching unit 103. The estimated time is a known time period required for the switching between imaging optical paths. The estimated time is the same as the length of the switching period P10 shown in FIG. 4. The row number is the number of rows in which the imaging device 110 reads out the pixel signals in the measurement A mode.

The control unit 150 causes the measurement unit 130 to use an image in at least two frame periods based on the pixel signals which are read out in the measurement A mode by the imaging device 110. The control unit 150 causes the measurement unit 130 to execute measurement in which the images in at least two frame periods are used.

In the measurement A mode shown in FIG. 4, the imaging device 110 outputs the image V2, the image V3, and the image V4. The exposure period of the pixels 54 of the eighth row in the frame period V2 does not overlap the switching period P10. The pixel signals generated in the pixels 54 of the eighth row in the frame period V2 are based on the first optical image corresponding to the first optical path.

The exposure period of the pixels 54 of the eighth row in the frame period V3 overlaps the switching period P10. The pixel signals generated in the pixels 54 of the eighth row in the frame period V3 are based on the first optical image corresponding to the first optical path and the second optical image corresponding to the second optical path. For this reason, the image V3 is not suitable for measurement.

The exposure period of the pixels 54 of the eighth row in the frame period V4 does not overlap the switching period P10. The pixel signals generated in the pixels 54 of the eighth row in the frame period V4 are based on the second optical image corresponding to the second optical path. The control unit 150 causes the measurement unit 130 to execute measurement in which the image V2 and the image V4 are used. The measurement unit 130 executes the measurement of a subject on the basis of the image V2 and the image V4. An interval between a first timing and a second timing is the same as the length of the switching period P10. The first timing is a timing at which the imaging device 110 acquires the image V2. The second timing is a timing at which the imaging device 110 acquires the image V4. The interval between the first timing and the second timing is six milliseconds.

The exposure periods of the pixels 54 of the ninth row to the thirteenth row in the frame period V2 overlap the switching period P10. In the image V2, the pixel signals of the pixels 54 of the eighth row can be used in measurement, but the pixel signals of the pixels 54 of the ninth row to the thirteenth row are not suitable for measurement. The measurement unit 130 performs measurement using the pixel signals of the pixels 54 of the eighth row in the image V2 and the pixel signals of the pixels 54 of the eighth row in the image V4.

The imaging device 110 reads out the pixel signals from the pixels 54 of at least one row including a measurement row in the measurement A mode. The measurement row includes a pixel 54 corresponding to the measurement coordinates. In the switching period P10, the imaging device 110 may not read out the pixel signals from the pixels 54 of at least one row out of the ninth row to the thirteenth row.

Rows in which the imaging device 110 reads out the pixel signals in the measurement A mode are not limited to the eighth row to the thirteenth row. The rows in which the imaging device 110 reads out the pixel signals in the measurement A mode only have to include the measurement row. For example, the imaging device 110 may read out the pixel signals of the pixels 54 of the third row to the eighth row in the measurement A mode. After the imaging device 110 reads out the pixel signals from the pixels 54 of the measurement row in the measurement A mode, the imaging conditions are switched.

Figure 6:
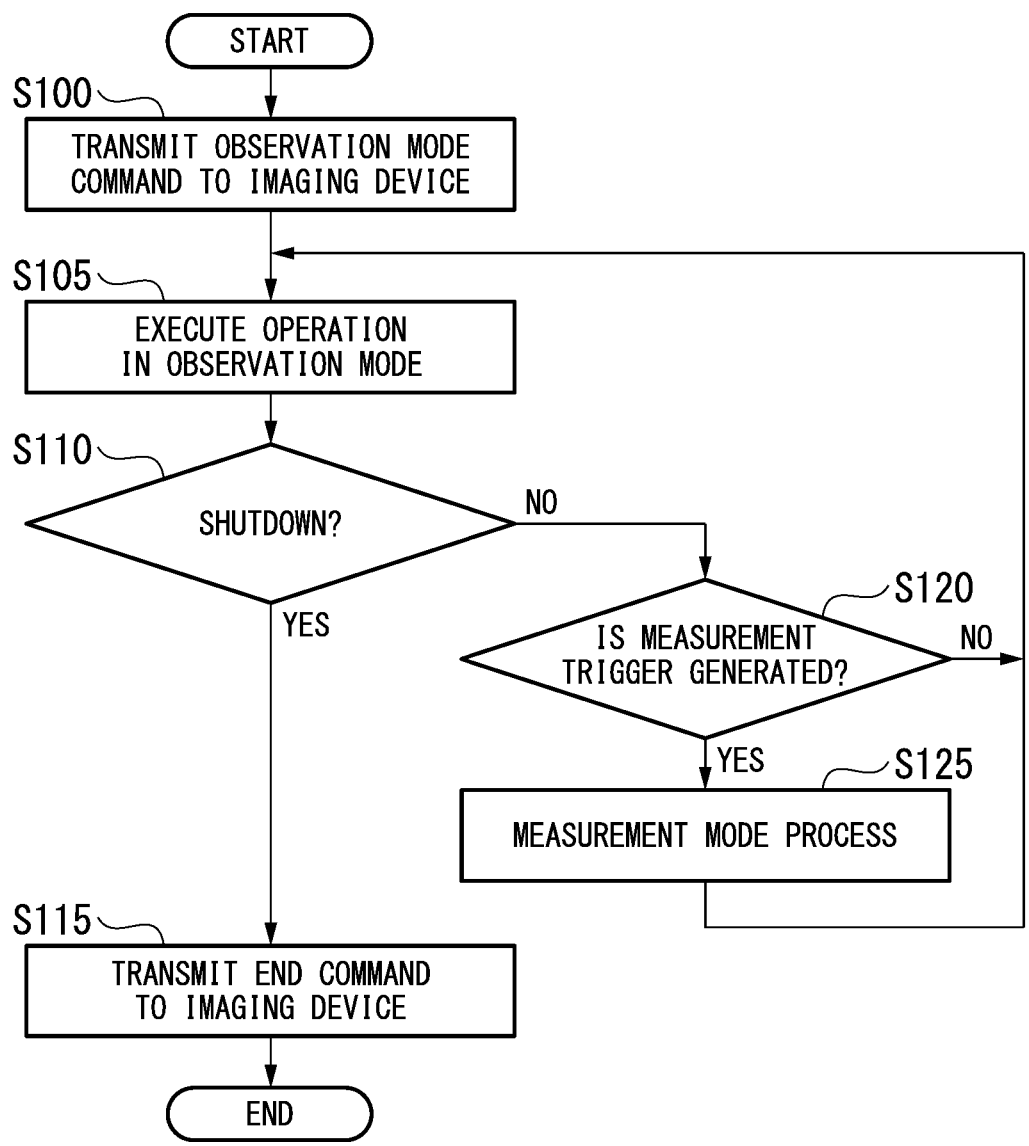
FIG. 6 is a flow chart showing a procedure of operations of the endoscope device according to the first embodiment of the present invention.

FIG. 6 shows a procedure of operations of the endoscope device 10. The operation of the endoscope device 10 will be described with reference to FIG. 6.

When the endoscope device 10 starts up, the endoscope device 10 operates in the observation mode. The imaging control unit 1501 transmits an observation mode command to the imaging device 110. Thereby, the imaging control unit 1501 brings the imaging device 110 into an operation in the observation mode (step S100).

After step S100, the imaging device 110 starts its operation in the observation mode on the basis of the observation mode command The image processing unit 120 starts image processing, and the display unit 140 starts displaying an image (step S105). When the endoscope device 10 starts up, the optical path switching unit 103 sets the first optical path as an imaging optical path. The imaging device 110 executes the operation in the frame period V1 shown in FIG. 4.

After step S105, the control unit 150 determines whether a power supply is turned off (step S110). For example, when turn-off of a power-supply switch which is not shown in FIG. 1 is detected, the control unit 150 determines that the power supply has been turned off.

In step S110, in a case where the control unit 150 determines that the power supply has been turned off, the imaging control unit 1501 transmits a shutdown command to the imaging device 110 (step S115). After step S115, the endoscope device 10 executes a shutdown process. Thereby, the imaging device 110 stops imaging, the image processing unit 120 stops the image processing, and the display unit 140 stops displaying an image.

In step S110, in a case where the control unit 150 determines that the power supply has not been turned off, the control unit 150 determines whether the measurement trigger is generated (step S120).

In step S120, in a case where the control unit 150 determines that the measurement trigger has not been generated, the process in step S105 is executed. Until the measurement trigger is generated, the same operation as the operation in the frame period V1 shown in FIG. 4 is continued.

In step S120, in a case where the control unit 150 determines that the measurement trigger has been generated, the control unit 150 executes a measurement mode process (step S125). After step S125, the process in step S105 is executed.

Figure 7:
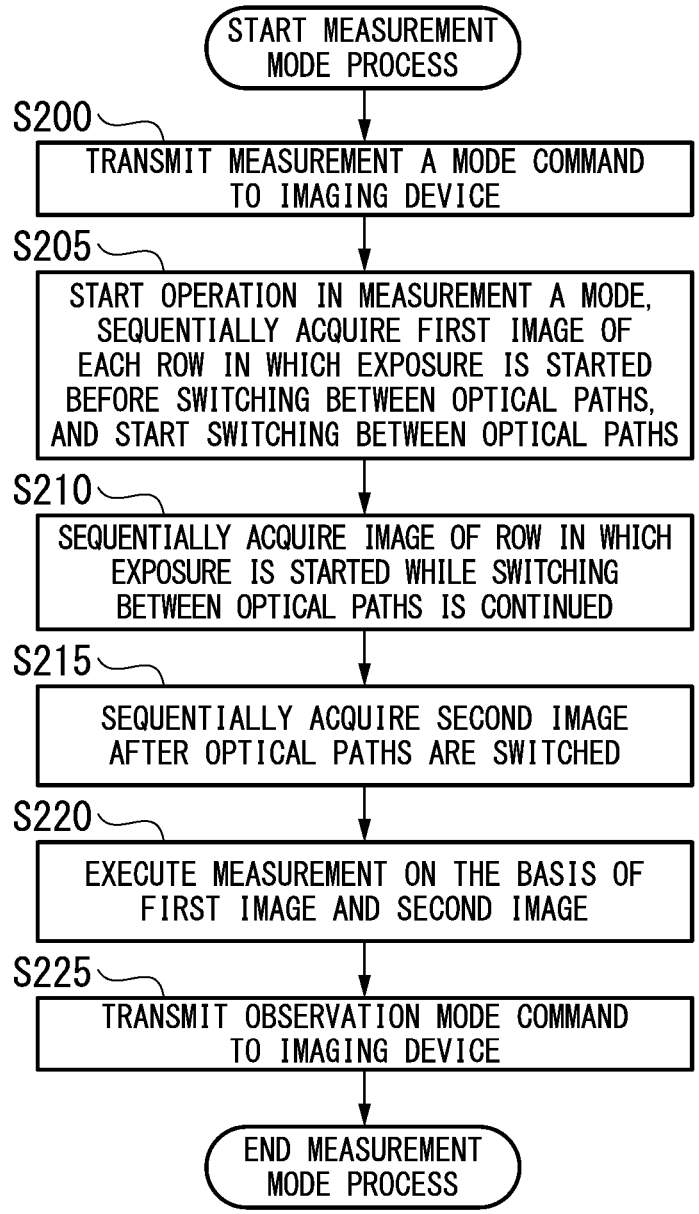
FIG. 7 is a flow chart showing a procedure of operations of the endoscope device according to the first embodiment of the present invention.

FIG. 7 shows the details of the measurement mode process in step S125. The operation of the endoscope device 10 in the measurement mode process will be described with reference to FIG. 7.

When the measurement trigger is generated, the endoscope device 10 operates in the measurement A mode. The imaging control unit 1501 transmits a measurement A mode command to the imaging device 110. Thereby, the imaging control unit 1501 brings the imaging device 110 into an operation in the measurement A mode (step S200).

After step S200, the imaging device 110 starts its operation in the measurement A mode on the basis of the measurement A mode command The imaging device 110 sequentially reads out the pixel signals of the pixels 54 of each row in which exposure is started before the switching between imaging optical paths. The pixel signals generated by exposure in the frame period V2 shown in FIG. 4 are read out. Thereby, the imaging device 110 sequentially acquires the first image based on the pixel signals of the pixels 54 of each row. The optical path control unit 1500 outputs the control signal to the optical path switching unit 103. Thereby, the optical path control unit 1500 causes the optical path switching unit 103 to start switching between imaging optical paths. The optical path switching unit 103 starts switching from the first optical path to the second optical path on the basis of the control signal from the optical path control unit 1500 (step S205). In step S205, switching between imaging optical paths is started simultaneously with the start of read-out of the pixel signal.

After step S205, the imaging device 110 sequentially reads out the pixel signals of the pixels 54 of a row in which exposure is started while switching between optical paths is continued. The pixel signals generated by exposure in the frame period V3 shown in FIG. 4 are read out. Thereby, the imaging device 110 sequentially acquires an image based on the pixel signals of the pixels 54 of each row (step S210). This image includes the pixel signals based on two optical images different from each other. For this reason, the image V3 shown in FIG. 4 is not suitable for measurement.

After step S210, the read-out of the pixel signal generated by exposure in the frame period V3 is completed, and switching between imaging optical paths is completed. The imaging device 110 sequentially reads out the pixel signals of the pixels 54 of a row in which exposure is started after the optical paths are switched. The pixel signals generated by exposure in the frame period V4 shown in FIG. 4 are read out. Thereby, the imaging device 110 sequentially acquires the second image based on the pixel signals of the pixels 54 of each row (step S215).

After step S215, the control unit 150 causes the measurement unit 130 to execute measurement in which the first image and the second image are used. The first image is the image V2 shown in FIG. 4. The second image is the image V4 shown in FIG. 4. The measurement unit 130 executes the measurement of a subject on the basis of the first image and the second image which are output from the image processing unit 120. The display unit 140 displays a measurement result (step S220).

After step S220, the imaging control unit 1501 transmits the observation mode command to the imaging device 110. Thereby, the imaging control unit 1501 brings the imaging device 110 into an operation in the observation mode (step S225). At this moment, the measurement mode process ends. After the measurement mode process ends, the process in step S105 is executed.

When the measurement mode process ends, the second optical path is set as an imaging optical path. In order for the endoscope device 10 to continue its operation after the measurement mode process ends, the following change may be considered. In processes executed after the measurement mode process ends, the first optical path in the processes shown in FIGS. 6 and 7 may be replaced with the second optical path. In the processes executed after the measurement mode process ends, the second optical path in the processes shown in FIG. 6 and FIG. 7 may be replaced with the first optical path. When the imaging device 110 operates in the observation mode, the second optical path is set as an imaging optical path. When the measurement trigger is generated, switching from the second optical path to the first optical path is executed.

Figure 34:
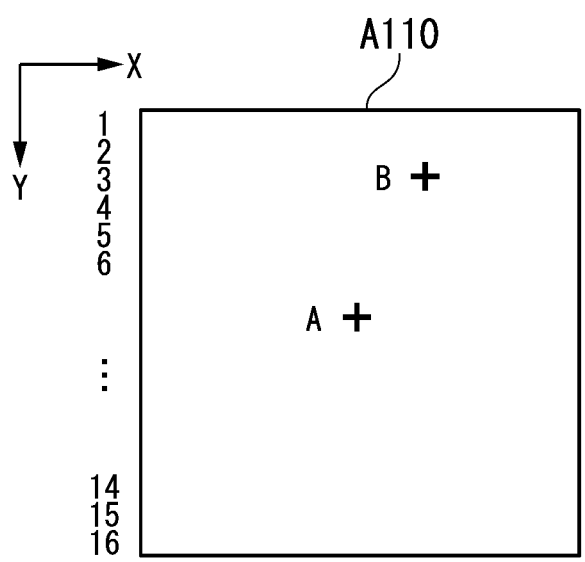
FIG. 34 is a diagram showing an imaging region of an imaging device according to a reference form of the present invention.
Figure 35:
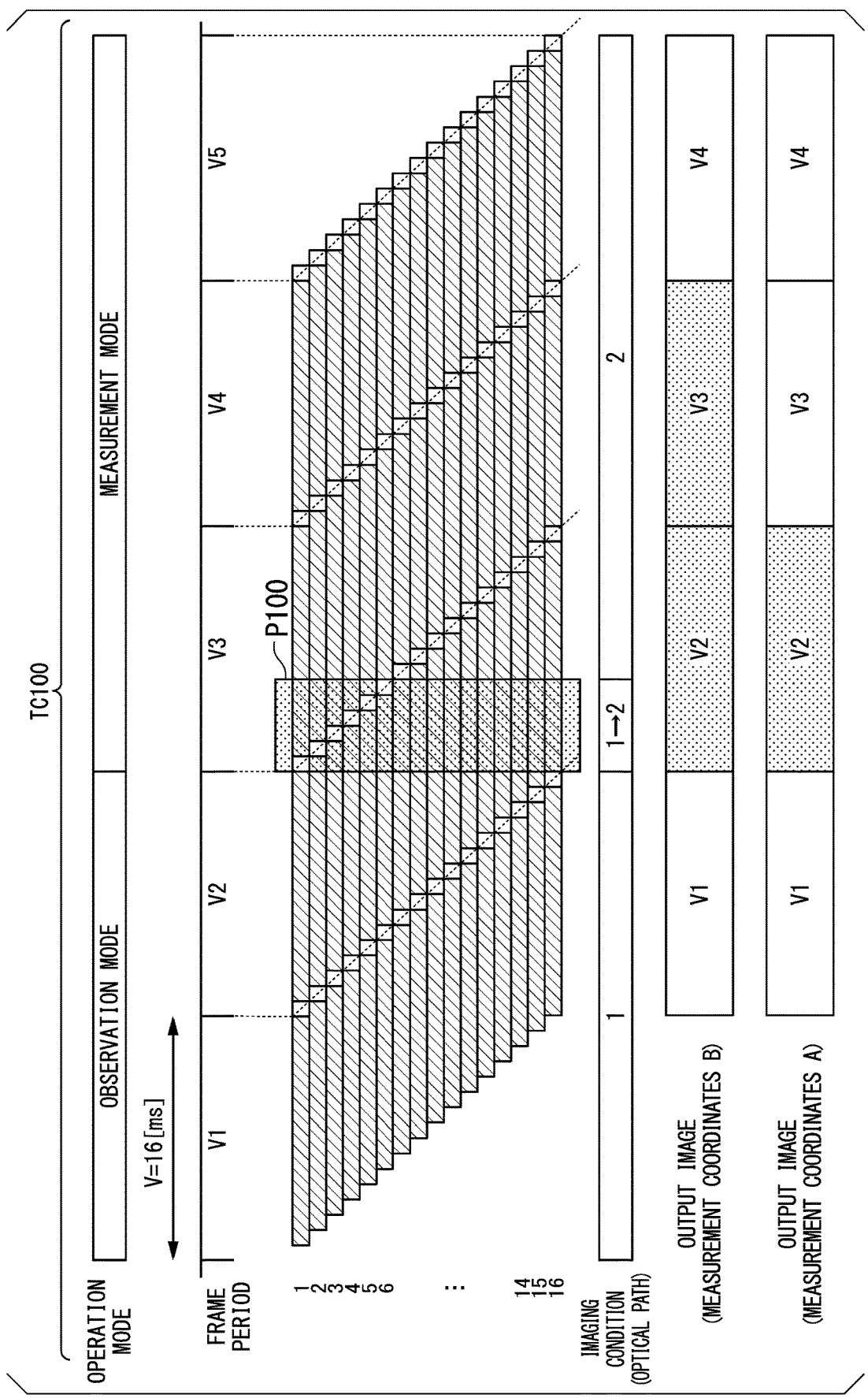
FIG. 35 is a timing chart showing an operation of the imaging device according to the reference form of the present invention.
Figure 36:
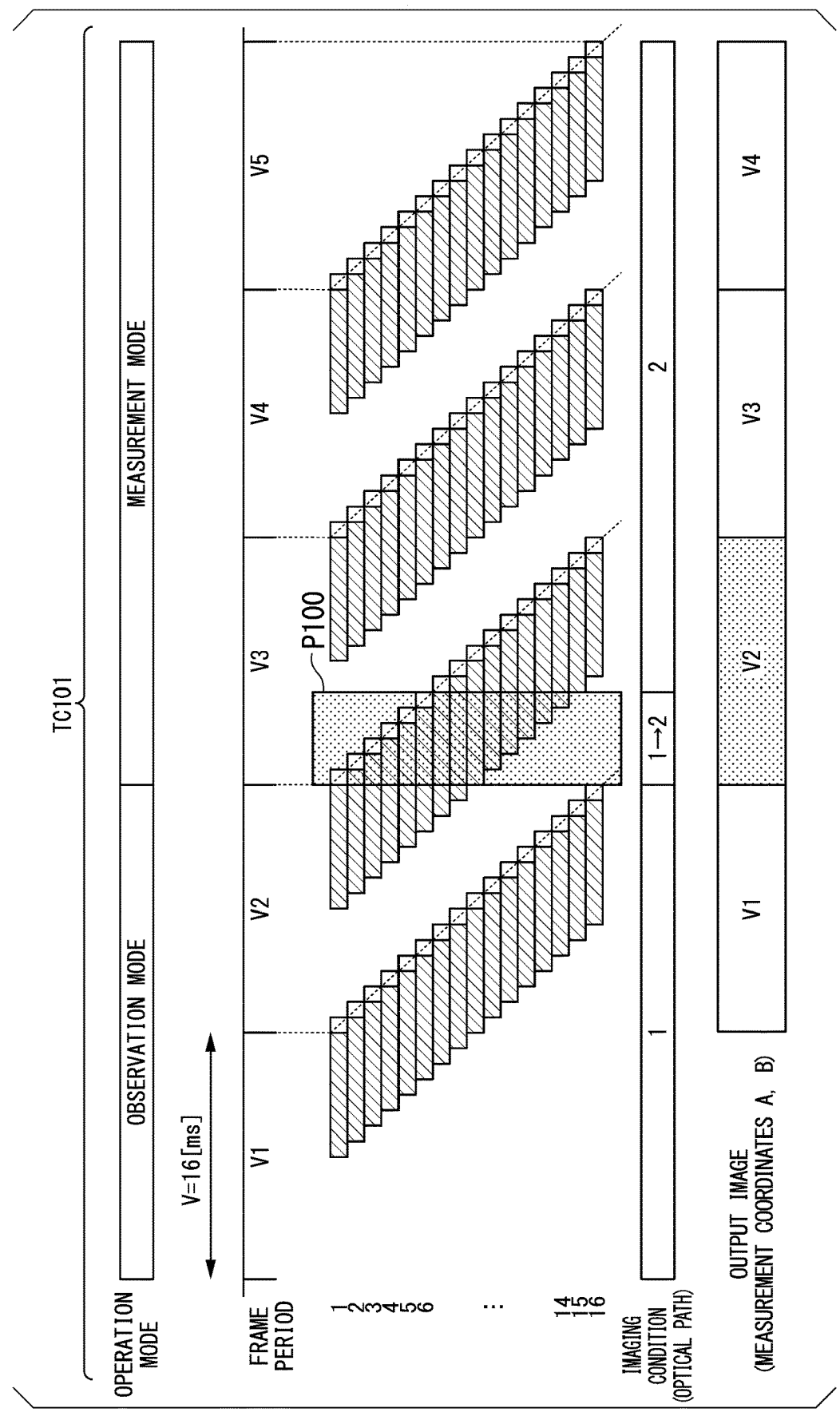
FIG. 36 is a timing chart showing an operation of the imaging device according to the reference form of the present invention.

The first embodiment of the present invention and reference forms of the present invention will be compared with each other with reference to FIGS. 34 to 36. The endoscope device 10 does not need to execute operations in the reference forms. Hereinafter, the operations of the endoscope device 10 in the reference forms will be described for the purpose of the comparison between the first embodiment and the reference forms.

FIG. 34 shows an imaging region A110 of the imaging device 110. Measurement coordinates A and measurement coordinates B are set in the imaging region A110. A pixel 54 located at the position of the measurement coordinates A is disposed in the eighth row of the imaging region A110. A pixel 54 located at the position of the measurement coordinates B is disposed in the third row of the imaging region A110.

A timing chart TC100 shown in FIG. 35 and a timing chart TC101 shown in FIG. 36 show the operations of the imaging device 110. The same portions as portions shown in FIG. 4 will not be described.

FIG. 35 shows an operation of the imaging device 110 in a case where an exposure period is relatively long. The imaging device 110 operates in the observation mode in the frame period V1. In the frame period V1, the imaging condition of the imaging device 110 is a first imaging condition. Therefore, the first optical path is set as an imaging optical path.

In the frame period V1, the exposure periods of the pixels 54 of the first row to the sixteenth row are sequentially started. Thereafter, in the frame period V2, the read-out periods of the pixels 54 of the first row to the sixteenth row are sequentially started, and the pixel signals of the pixels 54 of the first row to the sixteenth row are sequentially read out. The pixel signals generated in the exposure period of pixels 54 of each row in the frame period V1 are read out in the frame period V2.

In the frame period V2, the pixel signals of the pixels 54 of the first row to the sixteenth row are sequentially read out, and the exposure periods of the pixels 54 of the first row to the sixteenth row are sequentially started. The pixel signals generated in the exposure period of the pixels 54 of each row in the frame period V2 are read out in the frame period V3.

The read-out period of the pixels 54 of the sixteenth row in the frame period V2 ends. At this moment, the exposure period of the pixels 54 of the first row in the frame period V2 ends, and the read-out period of the pixels 54 of the first row in the frame period V3 is started. At this moment, the imaging device 110 starts its operation in the measurement mode. Switching between imaging conditions, that is, switching between imaging optical paths is started simultaneously with transition to the measurement mode. The optical path switching unit 103 starts switching from the first optical path to the second optical path.

In FIG. 35, a switching period P100 is shown. The length of the switching period P100 is the same as the length of the switching period P10 shown in FIG. 4. In the switching period P100, the imaging device 110 sequentially reads out the pixel signals of the pixels 54 of the first row to the sixth row.

When the read-out period of the pixels 54 of the sixth row in the frame period V3 ends, switching between imaging conditions, that is, switching between imaging optical paths is completed. The imaging optical path is the second optical path. The imaging device 110 sequentially starts the read-out periods of the pixels 54 of the seventh row to the sixteenth row, and sequentially reads out the pixel signals of the pixels 54 of the seventh row to the sixteenth row. An operation in which the imaging device 110 reads out the pixel signals in the frame period V3 is the same as the operation in which the imaging device 110 reads out the pixel signals in the frame period V2. The imaging device 110 continues the same operation as the operation for the frame period V1 in the frame period V3, the frame period V4, and the frame period V5.

The exposure periods of the pixels 54 of the first row to the sixteenth row in the frame period V1 do not overlap the switching period P100. The pixel signals generated in the pixels 54 of the first row to the sixteenth row in the frame period V1 are based on the first optical image corresponding to the first optical path.

The exposure period of the pixels 54 of the eighth row in the frame period V2 and the exposure period of the pixels 54 of the third row in the frame period V2 overlap the switching period P100. In the frame period V2, the pixel signals generated in the pixels 54 of the eighth row are based on the first optical image corresponding to the first optical path and the second optical image corresponding to the second optical path. In the frame period V2, the pixel signals generated in the pixels 54 of the third row are based on the first optical image and the second optical image. For this reason, the image V2 is not suitable for measurement in the measurement coordinates A and measurement in the measurement coordinates B.

The exposure period of the pixels 54 of the eighth row in the frame period V3 does not overlap the switching period P100. In the frame period V3, the pixel signals generated in the pixels 54 of the eighth row are based on the second optical image. The exposure period of the pixels 54 of the third row in the frame period V3 overlaps the switching period P100. In the frame period V3, the pixel signals generated in the pixels 54 of the third row are based on the first optical image and the second optical image. For this reason, the image V3 is not suitable for measurement in the measurement coordinates B.

The measurement unit 130 performs measurement in the measurement coordinates A using the pixel signals of the pixels 54 of the eighth row in the image V1 and the pixel signals of the pixels 54 of the eighth row in the image V3. An interval between a first timing and a second timing is sixteen milliseconds. The first timing is a timing at which the imaging device 110 acquires the image V1. The second timing is a timing at which the imaging device 110 acquires the image V3. The measurement unit 130 performs measurement in the measurement coordinates B using the pixel signals of the pixels 54 of the third row in the image V1 and the pixel signals of the pixels 54 of the third row in the image V4. An interval between the first timing and a third timing is 32 milliseconds. The third timing is a timing at which the imaging device 110 acquires the image V4.

FIG. 36 shows an operation of the imaging device 110 in a case where an exposure period is relatively short. In the timing chart TC101 shown in FIG. 36, the exposure period of the pixels 54 of each row is shorter than that in the timing chart TC100 shown in FIG. 35. An operation in which the imaging device 110 reads out the pixel signals is the same as the operation shown in FIG. 35.

The exposure periods of the pixels 54 of the first row to the sixteenth row in the frame period V1 do not overlap the switching period P100. The pixel signals generated in the pixels 54 of the first row to the sixteenth row in the frame period V1 are based on the first optical image corresponding to the first optical path.

The exposure period of the pixels 54 of the eighth row in the frame period V2 and the exposure period of the pixels 54 of the third row in the frame period V2 overlap the switching period P100. In the frame period V2, the pixel signals generated in the pixels 54 of the eighth row are based on the first optical image corresponding to the first optical path and the second optical image corresponding to the second optical path. In the frame period V2, the pixel signals generated in the pixels 54 of the third row are based on the first optical image and the second optical image. For this reason, the image V2 is not suitable for measurement in the measurement coordinates A and measurement in the measurement coordinates B.

The exposure period of the pixels 54 of the eighth row in frame period V3 and the exposure period of the pixels 54 of the third row in frame period V3 do not overlap the switching period P100. In the frame period V3, the pixel signals generated in the pixels 54 of the eighth row and the pixel signals generated in the pixels 54 of the third row are based on the second optical image.

The measurement unit 130 performs measurement in the measurement coordinates A and measurement in the measurement coordinates B using the pixel signals of the pixels 54 of the eighth row and the third row in the image V1 and the pixel signals of the pixels 54 of the eighth row and the third row in the image V3. An interval between a first timing and a second timing is sixteen milliseconds. The first timing is a timing at which the imaging device 110 acquires the image V1. The second timing is a timing at which the imaging device 110 acquires the image V3.

In the operations shown in FIGS. 35 and 36, an interval in which two images for measurement are acquired is sixteen milliseconds or more. For this reason, there is the possibility that a blur between two images is large. On the other hand, in the operation shown in FIG. 4, an interval in which two images for measurement are acquired is six milliseconds. The endoscope device 10 can shorten the time interval of imaging under a plurality of imaging conditions. Therefore, the interval in which two images for measurement are acquired becomes shorter. A blur between two images used in measurement is reduced, and a measurement error caused by the influence of the blur decreases. That is, the accuracy of measurement is improved.

In the endoscope device according to each aspect of the present invention, the image processing unit 120 and the display unit 140 are not essential.

A method of operating the endoscope device of each aspect of the present invention includes a first step, a second step, and a third step. Before an instruction for the measurement (measurement trigger) of a subject is generated, the imaging control unit 1501 brings the imaging device 110 into an operation in the first read-out mode (observation mode) in the first step (S100). In the first read-out mode, the imaging device 110 reads out the pixel signals from the pixels 54 in all or some of a plurality of rows in the first time. After the instruction for the measurement of a subject is generated, the imaging control unit 1501 brings the imaging device 110 into an operation in the second read-out mode (measurement A mode) in the second step (S200). In the second read-out mode, the imaging device 110 reads out the pixel signals from the pixels 54 in all or some of a plurality of rows in the second time. The second time is shorter than the first time. The imaging control unit 1501 causes the optical path switching unit 103 to switch imaging conditions (imaging optical paths) in the third step (S205) on the basis of the operation of the imaging device 110 in the second read-out mode.

First Modification Example of First Embodiment

A first modification example of the first embodiment of the present invention will be described using the endoscope device 10 shown in FIG. 1. In the endoscope device 10, an imaging optical path is switched from the first optical path to the second optical path. Thereafter, the imaging optical path is switched from the second optical path to the first optical path.

Figure 8:
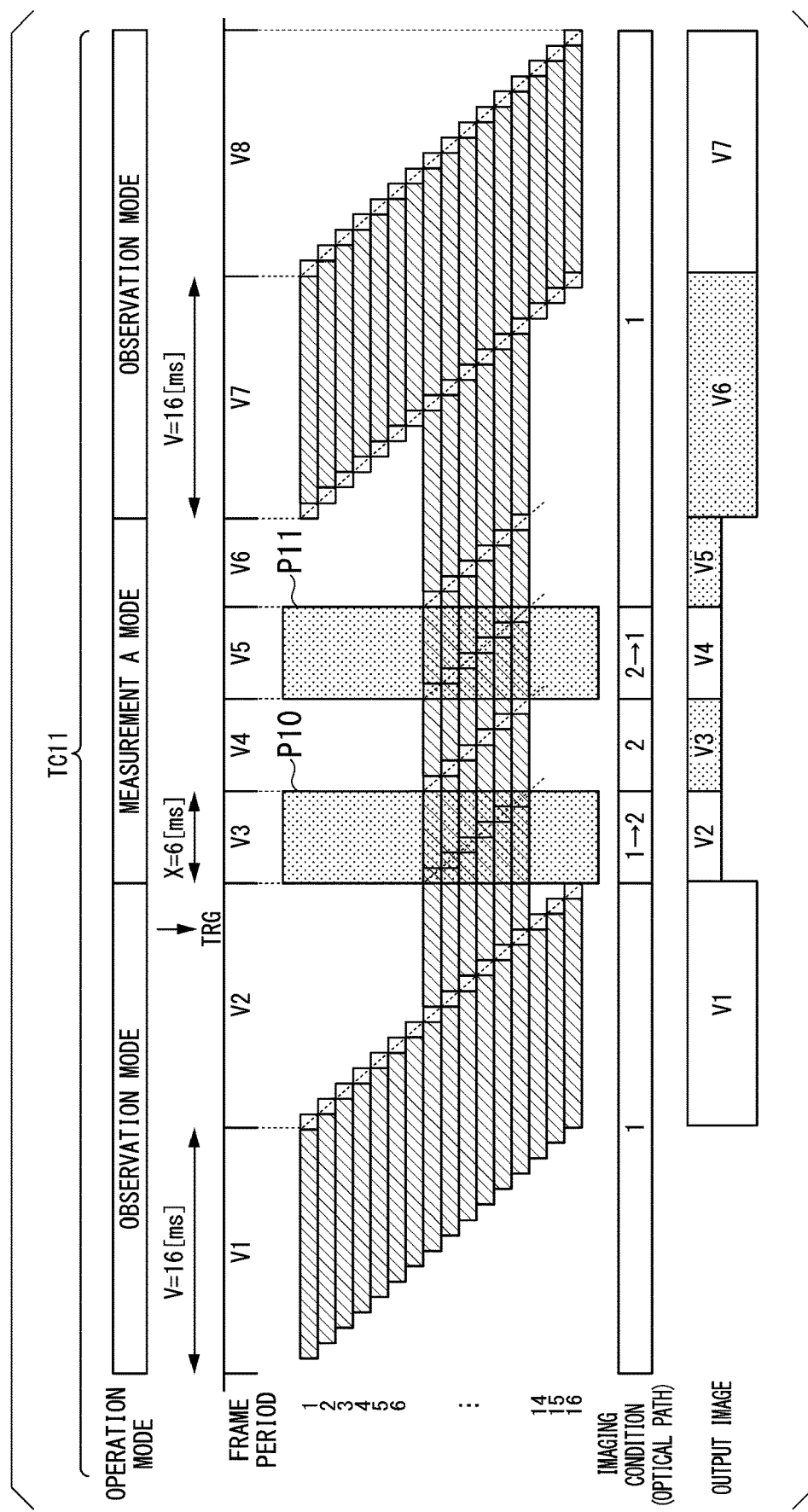
FIG. 8 is a timing chart showing an operation of an imaging device according to a first modification example of the first embodiment of the present invention.

FIG. 8 shows an operation of the imaging device 110. The operation of the imaging device 110 will be described with reference to FIG. 8. The same portions as portions shown in FIG. 4 will not be described.

A timing chart TC11 shows the operation of the imaging device 110. The operation of the imaging device 110 until the pixel signals are read out in the frame period V4 is the same as the operation shown in FIG. 4. The pixel signals generated in the exposure period of the pixels 54 of each row in the frame period V4 are read out in the frame period V5. The read-out period of the pixels 54 of the thirteenth row in the frame period V4 ends. At this moment, the exposure period of the pixels 54 of the eighth row in the frame period V4 ends, and the read-out period of the pixels 54 of the eighth row in the frame period V5 is started.

When the read-out period of the pixels 54 of the eighth row in the frame period V5 is started, switching between imaging conditions, that is, switching between imaging optical paths is started. The imaging control unit 1501 outputs a control signal for the switching between imaging optical paths to the optical path switching unit 103. Thereby, the optical path control unit 1500 causes the optical path switching unit 103 to switch imaging optical paths. The optical path switching unit 103 starts switching from the second optical path to the first optical path on the basis of the control signal from the imaging control unit 1501. When the frame period V5 is started, the optical path switching unit 103 starts switching between imaging optical paths.

In FIG. 8, a switching period P11 is shown. The length of the switching period P11 is the same as the length of the switching period P10. The imaging control unit 1501 causes the imaging device 110 to read out the pixel signals from the pixels 54 of six rows in the switching period P11. In the switching period P11, the imaging device 110 sequentially starts the read-out periods of the pixels 54 of the eighth row to the thirteenth row, and sequentially reads out the pixel signals of the pixels 54 of the eighth row to the thirteenth row. The pixels 54 of the eighth row to the thirteenth row are sequentially reset, and the exposure periods of the pixels 54 of the eighth row to the thirteenth row in the frame period V5 are sequentially started.

The pixel signals generated in the exposure period of the pixels 54 of each row in the frame period V5 are read out in a frame period V6. The read-out period of the pixels 54 of the thirteenth row in the frame period V5 ends. At this moment, the exposure period of the pixels 54 of the eighth row in the frame period V5 ends, and the read-out period of the pixels 54 of the eighth row in the frame period V6 is started. At this moment, switching between imaging conditions, that is, switching between imaging optical paths is completed. The imaging optical path is the first optical path. The imaging device 110 sequentially starts the read-out periods of the pixels 54 of the eighth row to the thirteenth row, and sequentially reads out the pixel signals of the pixels 54 of the eighth row to the thirteenth row. An operation in which the imaging device 110 reads out the pixel signals in the frame period V6 is the same as the operation in which the imaging device 110 reads out the pixel signals in the frame period V5.

When the read-out period of the pixels 54 of the thirteenth row in the frame period V6 ends, the imaging control unit 1501 brings the imaging device 110 into an operation in the observation mode. The imaging control unit 1501 outputs a command for switching the operation mode of the imaging device 110 from the measurement A mode to the observation mode to the imaging device 110. The imaging device 110 starts its operation in the observation mode on the basis of the command from the imaging control unit 1501. In the observation mode, the imaging device 110 sequentially scans sixteen rows, and sequentially reads out the pixel signals from the pixels 54 of each row. The imaging device 110 outputs the first image at the first frame rate. The first image includes the pixel signals which are read out from the pixels 54 of sixteen rows. The first frame rate is lower than the second frame rate in the measurement A mode.

The pixel signals generated in the exposure period of the pixels 54 of each row in the frame period V6 are read out in a frame period V7. The read-out period of the pixels 54 of the thirteenth row in the frame period V6 ends. At this moment, the exposure period of the pixels 54 of the first row in the frame period V7 ends, and the read-out period of the pixels 54 of the eighth row in the frame period V7 is started. The operation of the imaging device 110 in the frame period V7 and a frame period V8 is the same as the operation of the imaging device 110 in the frame period V1.

In FIG. 8, an image (output image) which is output from the imaging device 110 is schematically shown. An image V1 includes the pixel signals which are read out from the pixels 54 of sixteen rows after the exposure period in the frame period V1. The image V1 includes the pixel signals which are read out in the observation mode by the imaging device 110. An image V2 includes the pixel signals which are read out from the pixels 54 of six rows after the exposure period in the frame period V2. The image V2 includes the pixel signals which are read out in the measurement A mode by the imaging device 110. The sizes of an image V3, an image V4, and an image V5 are the same as the size of the image V2. An image V6 includes the pixel signals which are read out from the pixels 54 of sixteen rows after the exposure period in the frame period V6. The image V6 includes the pixel signals which are read out in the observation mode by the imaging device 110. The size of an image V7 is the same as the size of the image V6.

In the measurement A mode shown in FIG. 8, the imaging device 110 outputs the image V2, the image V3, the image V4, and the image V5. The exposure period of the pixels 54 of the eighth row in the frame period V2 does not overlap the switching period P10. The pixel signals generated in the pixels 54 of the eighth row in the frame period V2 are based on the first optical image corresponding to the first optical path.

The exposure period of the pixels 54 of the eighth row in the frame period V3 overlaps the switching period P10. The pixel signals generated in the pixels 54 of the eighth row in the frame period V3 are based on the first optical image corresponding to the first optical path and the second optical image corresponding to the second optical path. For this reason, the image V3 is not suitable for measurement.

The exposure period of the pixels 54 of the eighth row in the frame period V4 does not overlap the switching period P10. The pixel signals generated in the pixels 54 of the eighth row in the frame period V4 are based on the second optical image corresponding to the second optical path. The control unit 150 causes the measurement unit 130 to execute measurement in which the image V2 and the image V4 are used. The measurement unit 130 executes the measurement of a subject on the basis of the image V2 and the image V4.

The exposure period of the pixels 54 of the eighth row in the frame period V5 overlaps the switching period P11. The pixel signals generated in the pixels 54 of the eighth row in the frame period V5 are based on the first optical image and the second optical image. For this reason, the image V5 is not suitable for measurement.

Regarding the frame period V2 to the frame period V6, the exposure periods of the pixels 54 of the first row to the seventh row and the exposure periods of the pixels 54 of the fourteenth row to the sixteenth row are not shown in FIG. 8. In the pixels 54 of the first row to the seventh row and the pixels 54 of the fourteenth row to the sixteenth row, the exposure periods continues from the frame period V2 to the frame period V6. The exposure periods of the pixels 54 of the first row to the seventh row and the fourteenth row to the sixteenth row in the frame period V6 overlap the switching period P11. The pixel signals generated in the pixels 54 of the first row to the seventh row in the frame period V6 and the pixel signals generated in the pixels 54 of the fourteenth row to the sixteenth row are not signals acquired in an appropriate exposure state. For this reason, the image V6 is not suitable for display.

The exposure periods of the pixels 54 of the first row to the sixteenth row in the frame period V7 do not overlap the switching period P11. The pixel signals generated in the pixels 54 of the first row to the sixteenth row in the frame period V7 are based on the first optical image.

The control unit 150 causes the display unit 140 to display an image generated in the observation mode. The display unit 140 displays the image generated in the observation mode. Only any one of the first image based on the first optical image and the second image based on the second optical image is displayed in the observation mode before the measurement A mode and the observation mode after the measurement A mode. In the example shown in FIG. 8, the display unit 140 displays the first image. The display unit 140 displays the image V1 and the image V7, and does not display the image V6. In a case where an image displayed in the observation mode switches between the first image and the second image, composition is changed due to switching between images. For this reason, the visibility of the image is bad. An image displayed in the observation mode by the display unit 140 is fixed to any one of the first image and the second image. Therefore, the visibility of the image displayed in the observation mode is kept.

In a period in which an image generated in the measurement A mode is to be displayed, the control unit 150 may cause the display unit 140 to display the image generated in the observation mode. For example, in periods in which the image V2, the image V3, the image V4, and the image V5 shown in FIG. 8 are displayed, the display unit 140 continues to display the image V1.

The optical path control unit 1500 may cause the optical path switching unit 103 to repeat switching between the first optical path and the second optical path. That is, the optical path control unit 1500 may cause the optical path switching unit 103 to alternately set the first optical path and the second optical path as an imaging optical path. At this moment, the optical path switching unit 103 sets the first optical path as an imaging optical path multiple times, and sets the second optical path as an imaging optical path multiple times. The imaging device 110 outputs a plurality of first images based on the first optical image, and the imaging device 110 outputs a plurality of second images based on the second optical image. The measurement unit 130 may generate a third image by processing the plurality of first images. The measurement unit 130 may generate a fourth image by processing the plurality of second images. The measurement unit 130 may execute the measurement of a subject on the basis of the third image and the fourth image.

Figure 9:
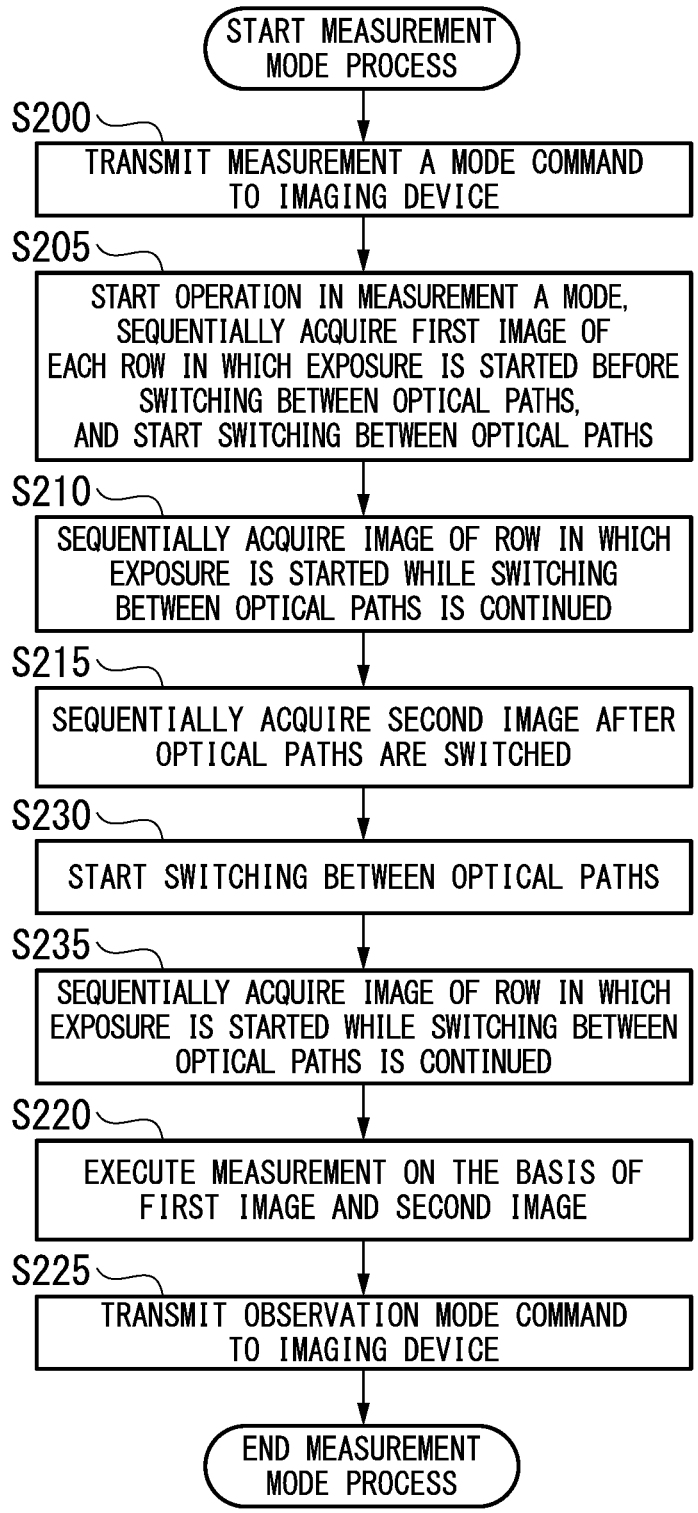
FIG. 9 is a flow chart showing a procedure of operations of an endoscope device according to the first modification example of the first embodiment of the present invention.

FIG. 9 shows the details of the measurement mode process. The operation of the endoscope device 10 in the measurement mode process will be described with reference to FIG. 9. The same process as the process shown in FIG. 7 will not be described.

After step S215, the optical path control unit 1500 outputs a control signal to the optical path switching unit 103. Thereby, the optical path control unit 1500 causes the optical path switching unit 103 to start switching between imaging optical paths. The optical path switching unit 103 starts switching from the second optical path to the first optical path on the basis of the control signal from the optical path control unit 1500 (step S230).

After step S230, the imaging device 110 sequentially reads out the pixel signals of the pixels 54 of a row in which exposure is started while switching between optical paths is continued. The pixel signals generated by exposure in the frame period V5 shown in FIG. 8 are read out. Thereby, the imaging device 110 sequentially acquires an image based on the pixel signals of the pixels 54 of each row (step S235). This image includes the pixel signals based on two optical images different from each other. For this reason, the image V5 shown in FIG. 8 is not suitable for measurement. After step S235, the process in step S220 is executed.

Second Modification Example of First Embodiment

A second modification example of the first embodiment of the present invention will be described using the endoscope device 10 shown in FIG. 1. The endoscope device 10 according to the first embodiment makes the size of an image generated in the measurement A mode smaller than the size of an image generated in the observation mode. An endoscope device 10 according to the second modification example of the first embodiment makes the length of a read-out period of one row in the measurement A mode shorter than the length of a read-out period of one row in the observation mode.

Figure 10:
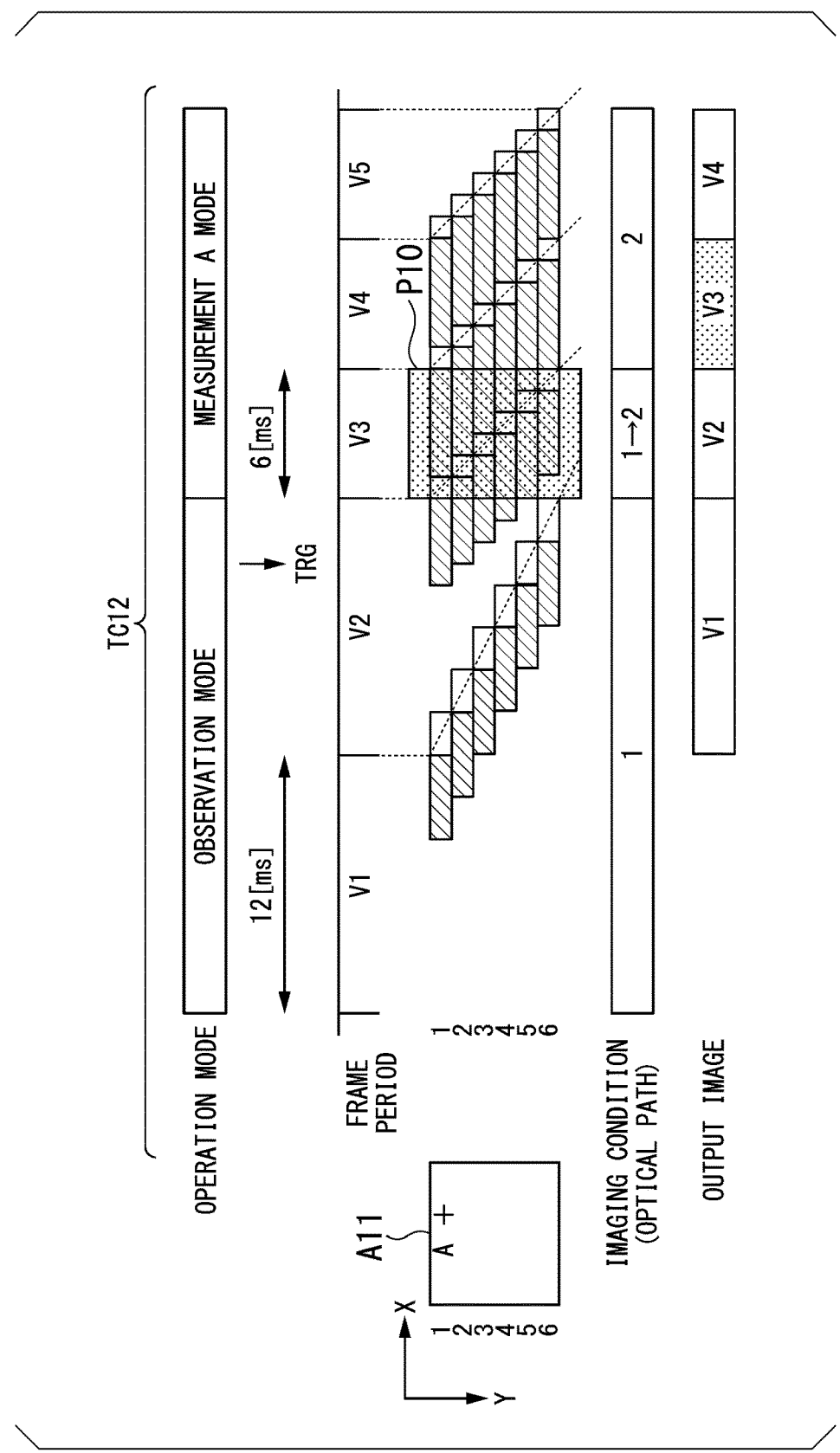
FIG. 10 is a timing chart showing an operation of an imaging device according to a second modification example of the first embodiment of the present invention.

FIG. 10 shows an operation of the imaging device 110. The operation of the imaging device 110 will be described with reference to FIG. 10. The same portions as portions shown in FIG. 4 will not be described.

In the example shown in FIG. 10, measurement coordinates A are set in the uppermost row of an imaging region A11. In the example shown in FIG. 10, the imaging region A11 has six rows. A pixel 54 located at the position of the measurement coordinates A is disposed in the first row of the imaging region A11.

A timing chart TC12 shows the operation of the imaging device 110. In the example shown in FIG. 10, the period of imaging in the observation mode, that is, the length of a frame period is twelve milliseconds. In an operation for each frame period in the observation mode, a time period (first time) required for read-out of the pixel signals of all the pixels 54 is twelve milliseconds.

A time period in which a pixel signal is read out from a pixel 54 in each row of a plurality of rows includes a blanking time. The blanking time is a time period from a timing at which read-out of a pixel signal is completed on one row to a timing at which read-out of a pixel signal is started in a row different from the one row. A blanking time when the imaging device 110 reads out the pixel signals in the measurement A mode is shorter than a blanking time when the imaging device 110 reads out the pixel signals in the observation mode.

Images which are output in the observation mode and the measurement A mode by the imaging device 110 include pixel signals which are read out from the pixels 54 of six rows. A time period in which the imaging device 110 reads out the pixel signals from the pixels 54 of one row in the frame period V3 is shorter than a time period in which the imaging device 110 reads out the pixel signals from the pixels 54 of one row in the frame period V2.

The read-out period of the pixels 54 of one row includes an effective time and a blanking time. The imaging device 110 reads out a pixel signal from the pixel 54 during an effective time. The imaging device 110 stops read-out of a pixel signal during a blanking time. An effective time for the read-out period in the frame period V2 and an effective time for the read-out period in the frame period V3 are the same as each other. A blanking time for the read-out period in the frame period V2 and a blanking time for the read-out period in the frame period V3 are different from each other.

In the switching period P10, the imaging device 110 sequentially starts the read-out periods of the pixels 54 of the first row to the sixth row, and sequentially reads out the pixel signals of the pixels 54 of the first row to the sixth row.

In the example shown in FIG. 10, the length of a frame period in the measurement A mode is six milliseconds. In the operation for each frame period in the measurement A mode, a time period (second time) required for read-out of the pixel signals of all the pixels 54 is six milliseconds.

After switching between imaging conditions, that is, imaging optical paths is started, a blanking time becomes shorter. Thereby, a frame rate is changed. Therefore, the time interval of imaging becomes shorter, and an interval in which the imaging device 110 outputs an image becomes shorter. The endoscope device 10 can shorten the time interval of imaging under a plurality of imaging conditions. Therefore, an interval in which two images for measurement are acquired becomes shorter. A blur between two images used in measurement is reduced, and a measurement error caused by the influence of the blur decreases. That is, the accuracy of measurement is improved.

Second Embodiment

Figure 11:
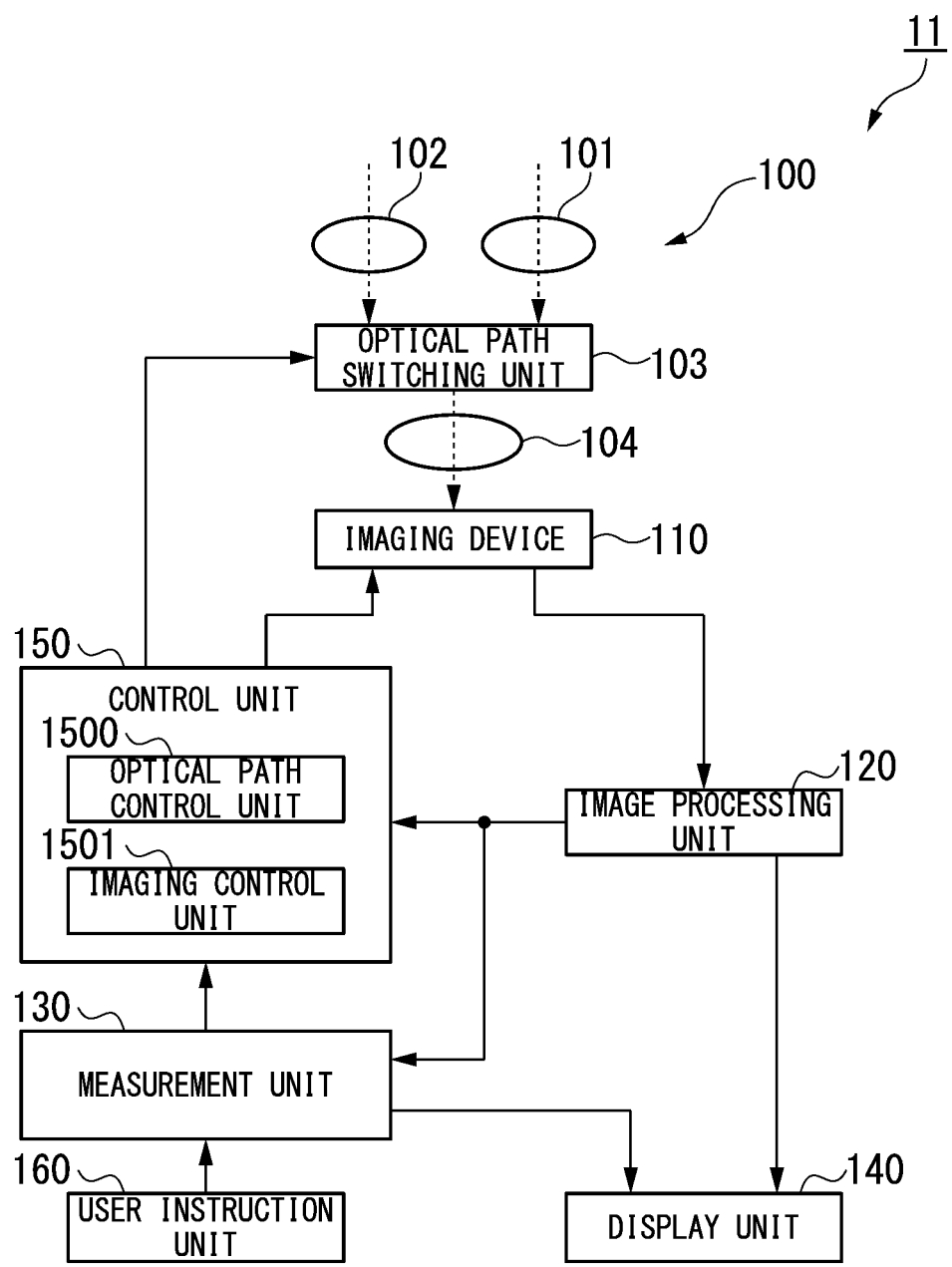
FIG. 11 is a block diagram showing a configuration of an endoscope device according to a second embodiment of the present invention.

FIG. 11 shows a configuration of an endoscope device 11 according to a second embodiment of the present invention. The same portions as portions shown in FIG. 1 will not be described. In the endoscope device 10 according to the first embodiment, the measurement coordinates are determined in advance. In the endoscope device 11 according to the second embodiment, a user indicates the measurement coordinates.

The endoscope device 11 includes a user instruction unit 160 in addition to the configuration of the endoscope device 10 shown in FIG. 1. The user instruction unit 160 outputs coordinate information indicating the measurement coordinates in accordance with a user's indication. The user instruction unit 160 is a user interface. The user interface includes at least one of a button, a switch, a key, a mouse, and the like. The display unit 140 and the user instruction unit 160 may be a touch panel. A user performs a touch using a finger, a click using a mouse, or the like with respect to a position of interest on an image displayed on the display unit 140. Thereby, a user performs pointing on an image using the user instruction unit 160. The user instruction unit 160 outputs coordinate information of a position indicated by a user to the measurement unit 130.

When the coordinate information is input from the user instruction unit 160 to the measurement unit 130, the measurement unit 130 generates a measurement trigger. The measurement unit 130 detects measurement coordinates on the basis of the coordinate information which is output from the user instruction unit 160. The measurement unit 130 outputs the measurement coordinates and the measurement trigger to the control unit 150.

Figure 12:
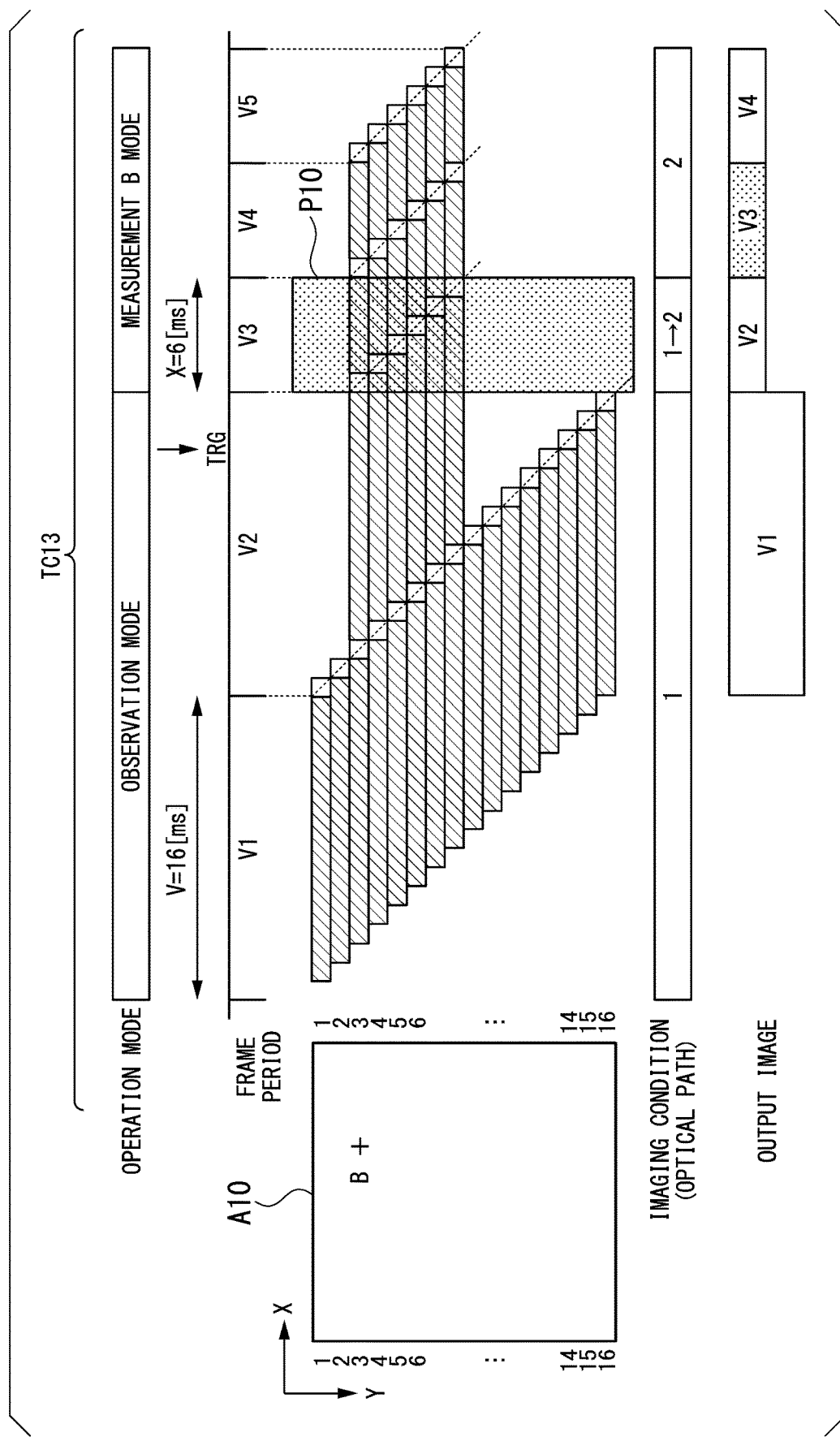
FIG. 12 is a timing chart showing an operation of an imaging device according to the second embodiment of the present invention.

FIG. 12 shows an operation of the imaging device 110. The operation of the imaging device 110 will be described with reference to FIG. 12. The same portions as portions shown in FIG. 4 will not be described.

In the example shown in FIG. 12, measurement coordinates B are set in the third row of the imaging region A10. A user indicates the measurement coordinates B by using the user instruction unit 160.

A timing chart TC13 shows the operation of the imaging device 110. When the read-out period of the pixels 54 of the sixteenth row in the frame period V2 ends, the imaging control unit 1501 brings the imaging device 110 into an operation in a measurement B mode (second read-out mode). The imaging control unit 1501 outputs a command for switching the operation mode of the imaging device 110 from the observation mode to the measurement B mode to the imaging device 110. The imaging device 110 starts its operation in the measurement B mode on the basis of the command from the imaging control unit 1501. In the measurement B mode, the imaging device 110 sequentially scans six rows, and sequentially reads out the pixel signals from the pixels 54 of each row.

The imaging control unit 1501 controls a read-out position on the basis of the position of the measurement coordinates B. In the example shown in FIG. 12, the pixel 54 corresponding to the measurement coordinates B is disposed in the third row. Therefore, the imaging device 110 initially reads out the pixel signals from the pixels 54 of the third row in the measurement B mode.

When the read-out period of the pixels 54 of the third row in the frame period V3 is started, switching between imaging conditions, that is, switching between imaging optical paths is started. The optical path switching unit 103 starts switching from the first optical path to the second optical path.

The imaging control unit 1501 causes the imaging device 110 to read out the pixel signals from the pixels 54 of six rows in the switching period P10. In the switching period P10, the imaging device 110 sequentially starts the read-out periods of the pixels 54 of the third row to the eighth row, and sequentially reads out the pixel signals of the pixels 54 of the third row to the eighth row. The pixels 54 of the third row to the eighth row are sequentially reset, and the exposure periods of the pixels 54 of the third row to the eighth row in the frame period V3 are sequentially started.

The pixel signals generated in the exposure period of the pixels 54 of each row in the frame period V3 are read out in the frame period V4. The read-out period of the pixels 54 of the eighth row in the frame period V3 ends. At this moment, the exposure period of the pixels 54 of the third row in the frame period V3 ends, and the read-out period of the pixels 54 of the third row in the frame period V4 is started. At this moment, switching between imaging conditions, that is, switching between imaging optical paths is completed. The imaging optical path is the second optical path. The imaging device 110 sequentially starts the read-out periods of the pixels 54 of the third row to the eighth row, and sequentially reads out the pixel signals of the pixels 54 of the third row to the eighth row. An operation in which the imaging device 110 reads out the pixel signals in the frame period V4 is the same as the operation in which the imaging device 110 reads out the pixel signals in the frame period V3. The imaging device 110 continues the same operation as the operation for the frame period V3 in the frame period V4 and the frame period V5.

Figure 13:
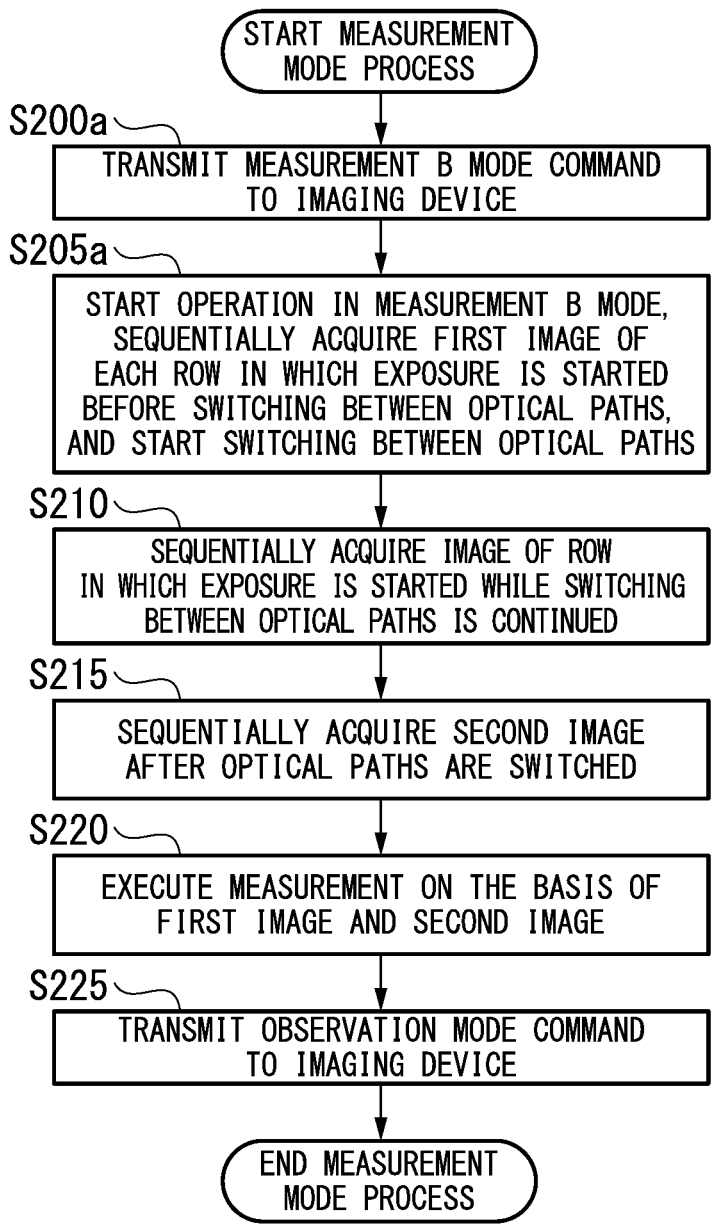
FIG. 13 is a flow chart showing a procedure of operations of the endoscope device according to the second embodiment of the present invention.

FIG. 13 shows the details of the measurement mode process. The operation of the endoscope device 11 in the measurement mode process will be described with reference to FIG. 13. The same process as the process shown in FIG. 7 will not be described.

The imaging control unit 1501 transmits a measurement B mode command to the imaging device 110. Thereby, the imaging control unit 1501 brings the imaging device 110 into an operation in the measurement B mode (step S200a).

After step S200a, the imaging device 110 starts its operation in the measurement B mode on the basis of the measurement B mode command. The imaging device 110 sequentially reads out the pixel signals of the pixels 54 of each row in which exposure is started before the switching between imaging optical paths. The pixel signals generated by exposure in the frame period V2 shown in FIG. 12 are read out. Thereby, the imaging device 110 sequentially acquires a first image based on the pixel signals of the pixels 54 of each row. The optical path control unit 1500 outputs a control signal to the optical path switching unit 103. Thereby, the optical path control unit 1500 causes the optical path switching unit 103 to start switching between imaging optical paths. The optical path switching unit 103 starts switching from the first optical path to the second optical path on the basis of the control signal from the optical path control unit 1500 (step S205a). In step S205a, switching between imaging optical paths is started simultaneously with the start of read-out of the pixel signal. After step S205a, the process in step S210 is executed.

In third to tenth embodiments, measurement coordinates may be set on the basis of the coordinate information which is output by the user instruction unit 160.

The endoscope device 11 can shorten the time interval of imaging under a plurality of imaging conditions. Therefore, an interval in which two images for measurement are acquired becomes shorter. A blur between two images used in measurement is reduced, and a measurement error caused by the influence of the blur decreases. That is, the accuracy of measurement is improved. The endoscope device 11 can acquire a measurement result in the measurement coordinates indicated by a user.

Third Embodiment

A third embodiment of the present invention will be described using the endoscope device 10 shown in FIG. 1. In the timing chart TC10 shown in FIG. 4, the measurement unit 130 performs measurement using the image V2 and the image V4. The length of an exposure period for the image V2 and the length of an exposure period for the image V4 are different from each other. For this reason, the brightness of the image V2 and the brightness of the image V4 are different from each other. Since the two images are different from each other in brightness, there is the possibility of the accuracy of measurement decreasing. The endoscope device 10 according to the third embodiment uniforms the brightnesses of the two images used in measurement.

The imaging control unit 1501 has a function of automatic exposure (AE), and controls the brightness of an image. Generally, a user uses an endoscope, to thereby observe a position distant from the endoscope and a position close to the endoscope. In a case where the endoscope device 10 acquires the image of a subject close to the endoscope, the exposure time of the imaging device 110 of the endoscope device 10 is made shorter. In a case where the endoscope device 10 acquires the image of a subject distant from the endoscope, the exposure time of the imaging device 110 of the endoscope device 10 is made longer. In a case where the brightness of an image is insufficient even when the exposure time increases, a gain of the imaging device 110 of the endoscope device 10 is raised. In a case where a gain is raised, noise in an image increases. For this reason, the visibility of an image decreases. It is preferable to suppress a gain in order to maintain the visibility of an image.

The image processing unit 120 determines the brightness of an image. The image processing unit 120 outputs brightness information indicating the brightness of an image to the control unit 150. The imaging control unit 1501 calculates an exposure time and a gain on the basis of the brightness information. The imaging control unit 1501 sets the calculated exposure time and gain in the imaging device 110.

The control unit 150 equalizes the brightnesses of images of at least two frame periods used in the measurement of a subject by the measurement unit 130. Specifically, the measurement unit 130 executes the measurement of a subject on the basis of a first image and a second image. The first image is generated on the basis of the pixel signals of the pixels 54 exposed in a first exposure period. The second image is generated on the basis of the pixel signals of the pixels 54 exposed in a second exposure period. The first exposure period includes a timing at which an instruction for the measurement of a subject is generated. The second exposure period is started after the optical path switching unit 103 completes switching between imaging conditions (imaging optical paths). The imaging control unit 1501 equalizes the length of the first exposure period with the length of the second exposure period on the basis of the length of the second exposure period determined in advance.

Figure 14:
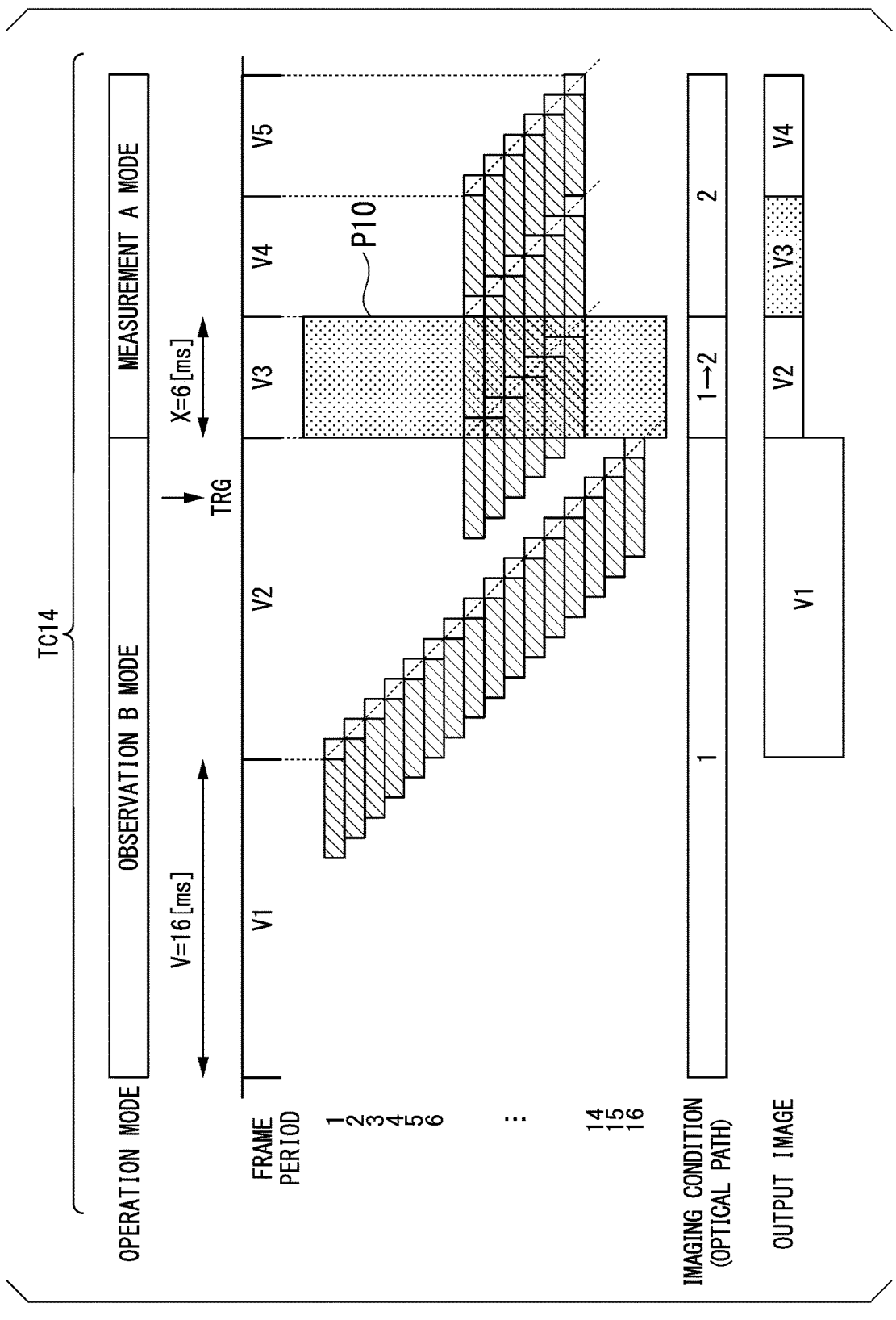
FIG. 14 is a timing chart showing an operation of an imaging device according to a third embodiment of the present invention.

FIG. 14 shows an operation of the imaging device 110. The operation of the imaging device 110 will be described with reference to FIG. 14. The same portions as portions shown in FIG. 4 will not be described.

A timing chart TC14 shows the operation of the imaging device 110. The switching period P10 includes a read-out period and an exposure period. The length of the switching period P10 is already-known. Before the imaging device 110 operates in the observation mode, the imaging control unit 1501 determines the length of the exposure period (second exposure period) in the measurement A mode. When the imaging device 110 operates in the observation mode, the imaging control unit 1501 determines the maximum value of the length of the exposure period (first exposure period) in the observation mode on the basis of the length of the exposure period in the measurement A mode. The imaging control unit 1501 sets the determined maximum value in the imaging device 110. The length of the exposure period which is set through a function of automatic exposure in the observation mode by the imaging device 110 is the same as or shorter than the set maximum value. In a case where the brightness of an image in the observation mode is insufficient, the imaging control unit 1501 adjusts a gain in the imaging device 110 in order to make an image bright.

In the example shown in FIG. 14, the imaging device 110 operates in the observation B mode instead of the observation mode in the first embodiment. The imaging control unit 1501 sets the maximum value of the length of the exposure period in the observation B mode to be the same as the length of the exposure period in the measurement A mode.

After the measurement trigger is generated, the read-out period of the pixels 54 of the sixteenth row in the frame period V2 ends. At this moment, the imaging device 110 starts its operation in the measurement A mode. The length of the exposure period in the measurement A mode is a length determined in advance.

Figure 15:
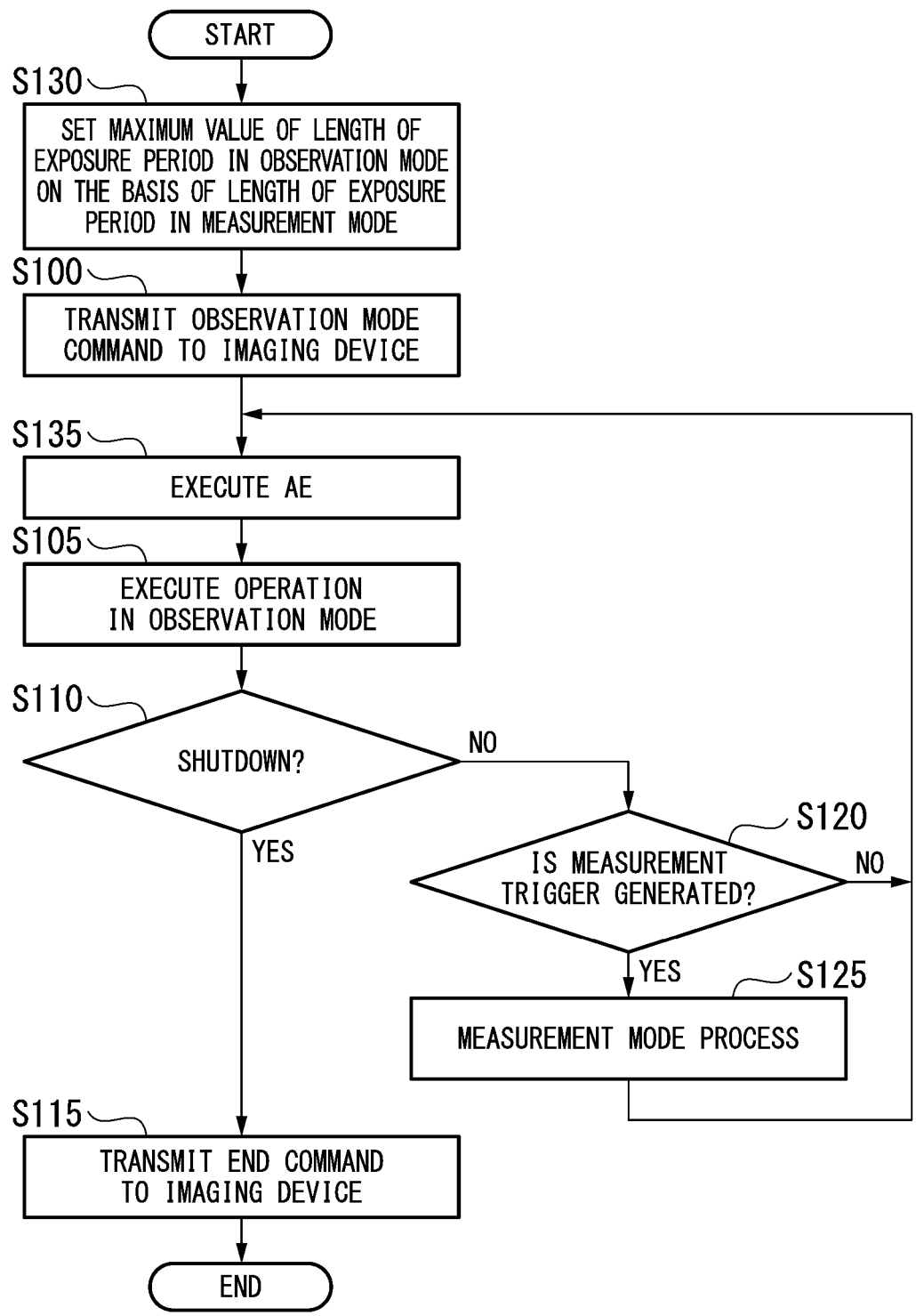
FIG. 15 is a flow chart showing a procedure of operations of an endoscope device according to the third embodiment of the present invention.

FIG. 15 shows a procedure of operations of the endoscope device 10. The operation of the endoscope device 10 will be described with reference to FIG. 15. The same process as the process shown in FIG. 6 will not be described.

When the endoscope device 10 starts up, the endoscope device 10 operates in the observation B mode. The imaging control unit 1501 sets the maximum value of the length of the exposure period in the observation B mode in the imaging device 110 on the basis of the length of the exposure period in the measurement A mode (step S130). After step S130, the process in step S100 is executed.

After step S100, the imaging control unit 1501 executes automatic exposure. The length of the exposure period which is set in the observation B mode is the same as or shorter than the maximum value which is set in step S130 (step S135). After step S135, the process in step S105 is executed.

In the timing chart TC14 shown in FIG. 14, the length of the exposure period for the image V2 and the length of the exposure period for the image V4 are the same as each other. For this reason, the brightness of the image V2 and the brightness of the image V4 are the same as each other. Since the two images are the same as each other in brightness, the accuracy of measurement is improved.

Fourth Embodiment

A fourth embodiment of the present invention will be described using the endoscope device 10 shown in FIG. 1. An endoscope device 10 according to the fourth embodiment uniforms the brightnesses of two images used in measurement by using a method different from the method in the third embodiment.

The measurement unit 130 executes the measurement of a subject on the basis of a first image and a second image. The first image is generated on the basis of the pixel signals of the pixels 54 exposed in a first exposure period. The second image is generated on the basis of the pixel signals of the pixels 54 exposed in a second exposure period. The first exposure period includes a timing at which an instruction for the measurement of a subject is generated. The second exposure period is started after the optical path switching unit 103 completes switching between imaging conditions (imaging optical paths). The imaging control unit 1501 equalizes the length of the second exposure period with the length of the first exposure period on the basis of the length of the first exposure period.

Figure 16:
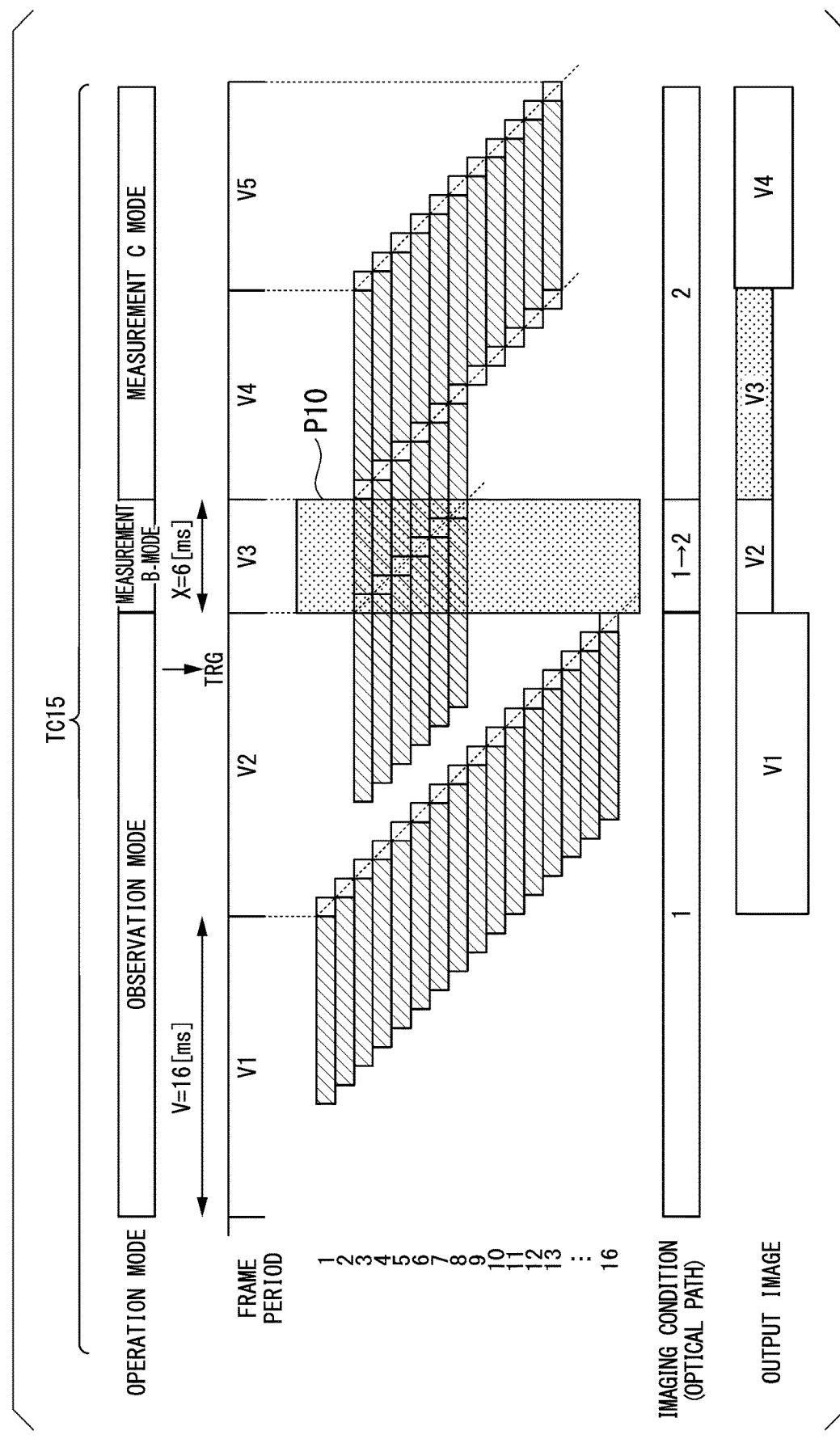
FIG. 16 is a timing chart showing an operation of an imaging device according to a fourth embodiment of the present invention.

FIG. 16 shows an operation of the imaging device 110. The operation of the imaging device 110 will be described with reference to FIG. 16. The same portions as portions shown in FIG. 12 will not be described.

A timing chart TC15 shows the operation of the imaging device 110. When the read-out period of the pixels 54 of the third row in the frame period V3 is started, switching between imaging conditions, that is, switching between imaging optical paths is started. After the optical path switching unit 103 starts switching between imaging optical paths, the imaging control unit 1501 determines the length of the exposure period (second exposure period) in a measurement C mode. The length of the exposure period in the measurement C mode is the same as the length of the exposure period (first exposure period) in the frame period V2 in which the measurement trigger is generated.

When the read-out period of the pixels 54 of the eighth row in the frame period V3 ends, switching between imaging conditions, that is, switching between imaging optical paths is completed. The imaging optical path is the second optical path. At this moment, the imaging control unit 1501 brings the imaging device 110 into an operation in the measurement C mode (second read-out mode). The imaging control unit 1501 outputs a command for switching the operation mode of the imaging device 110 from the measurement B mode to the measurement C mode to the imaging device 110. The imaging control unit 1501 sets the length of the exposure period in the measurement C mode to be the same as the length of the exposure period in the frame period V2. The imaging device 110 starts its operation in the measurement C mode on the basis of the command from the imaging control unit 1501.

The imaging control unit 1501 determines a row number on the basis of the length of the exposure period in the measurement C mode. The row number is the number of rows in which the imaging device 110 reads out the pixel signals in the measurement C mode. In the example shown in FIG. 16, the total of the lengths of ten read-out periods is the same as the length of the exposure period in the measurement C mode. When the imaging device 110 starts its operation in the measurement C mode, the read-out period of the pixels 54 of the third row in the frame period V4 is started. When the read-out period of the pixels 54 of the third row in the frame period V4 ends, the exposure period of the pixels 54 of the third row in the frame period V4 is started. In the exposure period in the frame period V4, the pixel signals of the pixels 54 of eleven rows including the third row to the thirteenth row are read out. In the measurement C mode, the imaging device 110 sequentially scans eleven rows including the third row to the thirteenth row, and sequentially reads out the pixel signals from the pixels 54 of each row.

The pixel signals generated in the exposure period of the pixels 54 of each row in the frame period V4 are read out in the frame period V5. The read-out period of the pixels 54 of the thirteenth row in the frame period V4 ends. At this moment, the exposure period of the pixels 54 of the third row in the frame period V4 ends, and the read-out period of the pixels 54 of the third row in the frame period V5 is started. The imaging device 110 sequentially starts the read-out periods of the pixels 54 of the third row to the thirteenth row, and the pixel signals of the pixels 54 of the third row to the thirteenth row are sequentially read out. An operation in which the imaging device 110 reads out the pixel signals in the frame period V5 is the same as the operation in which the imaging device 110 reads out the pixel signals in the frame period V4. The imaging device 110 continues the same operation as the operation for the frame period V4 in the frame period V5.

After the optical path switching unit 103 ends the switching between imaging optical paths, the imaging control unit 1501 brings the imaging device 110 into an operation in the measurement C mode. In the measurement C mode, the imaging device 110 reads out the pixel signals from the pixels 54 of eleven rows at a third time. The third time is shorter than the first time. The first time is a time period required for the imaging device 110 to read out the pixel signals from the pixels 54 of sixteen rows in the observation mode. In the example shown in FIG. 16, the third time is longer than the second time. The second time is a time period required for the imaging device 110 to read out the pixel signals from six pixels 54 in the measurement B mode. The third time may be the same as or shorter than the second time. That is, the imaging device 110 may read out the pixel signals from the pixels 54 of one to six rows including the third row in the measurement C mode.

The measurement unit 130 executes the measurement of a subject on the basis of the image V2 and the image V4. An interval between a first timing and a second timing is the same as the lengths of the read-out periods of eleven rows in the measurement C mode. The first timing is a timing at which the imaging device 110 acquires the image V2. The second timing is a timing at which the imaging device 110 acquires the image V4.

In the timing chart TC15 shown in FIG. 16 and the timing chart TC100 shown in FIG. 35, intervals in which two images for measurement are acquired are compared with each other. The interval in the timing chart TC15 is smaller than the interval in the timing chart TC100.

Figure 17:
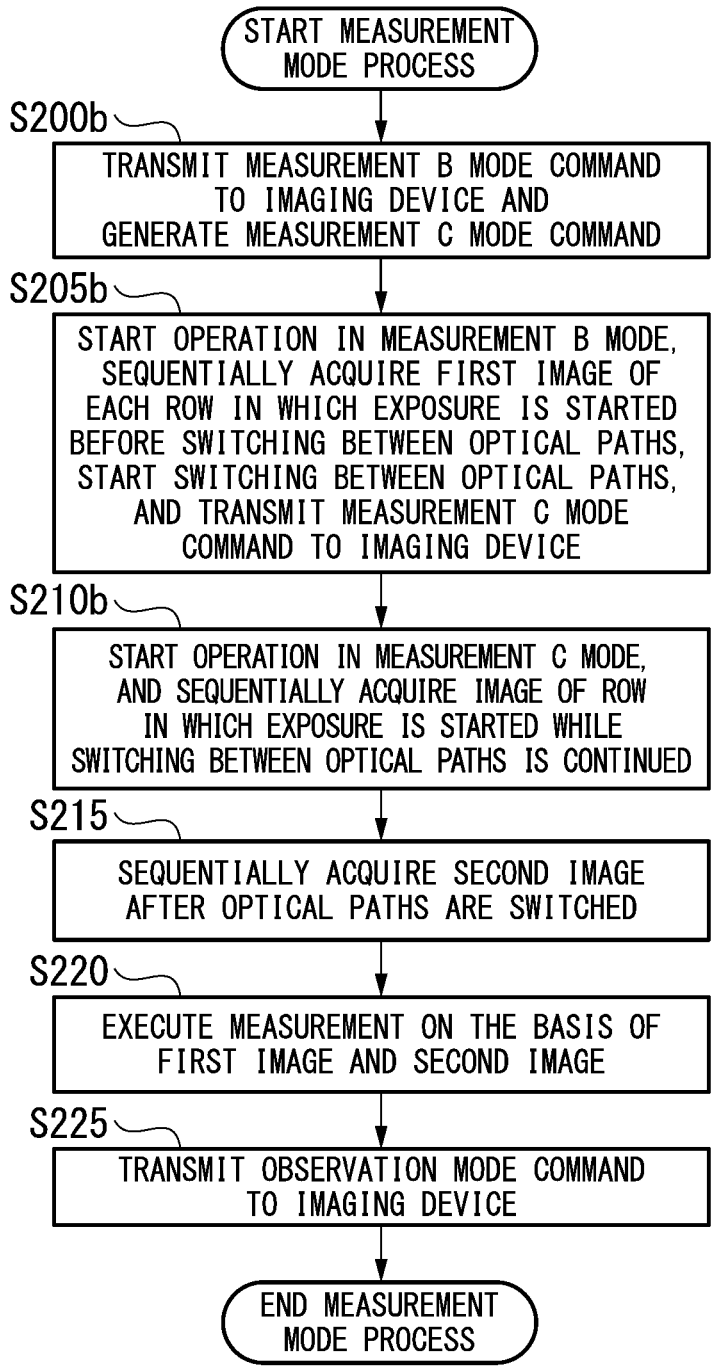
FIG. 17 is a flow chart showing a procedure of operations of an endoscope device according to the fourth embodiment of the present invention.

FIG. 17 shows the details of the measurement mode process. The operation of the endoscope device 10 in the measurement mode process will be described with reference to FIG. 17. The same process as the process shown in FIG. 13 will not be described.

The imaging control unit 1501 transmits the measurement B mode command to the imaging device 110. Thereby, the imaging control unit 1501 brings the imaging device 110 into an operation in the measurement B mode. The imaging control unit 1501 generates a measurement C mode command The measurement C mode command includes information of the exposure period in the observation mode (step S200*b*).

After step S200*b*, the imaging device 110 starts its operation in the measurement B mode on the basis of the measurement B mode command. The imaging device 110 sequentially reads out the pixel signals of the pixels 54 of each row in which exposure is started before the switching between imaging optical paths. The pixel signals generated by exposure in the frame period V2 shown in FIG. 16 are read out. Thereby, the imaging device 110 sequentially acquires the first image based on the pixel signals of the pixels 54 of each row. The optical path control unit 1500 outputs a control signal to the optical path switching unit 103. Thereby, the optical path control unit 1500 causes the optical path switching unit 103 to start switching between imaging optical paths. The optical path switching unit 103 starts switching from the first optical path to the second optical path on the basis of the control signal from the optical path control unit 1500. The imaging control unit 1501 transmits the measurement C mode command to the imaging device 110. Thereby, the imaging control unit 1501 brings the imaging device 110 into an operation in the measurement C mode (step S205*b*).

After step S205*b*, the imaging device 110 starts its operation in the measurement C mode on the basis of the measurement C mode command. The imaging device 110 sequentially reads out the pixel signals of the pixels 54 of a row in which exposure is started while the switching between optical paths is continued. The pixel signals generated by exposure in the frame period V3 shown in FIG. 16 are read out. Thereby, the imaging device 110 sequentially acquires an image based on the pixel signals of the pixels 54 of each row (step S210*b*). After step S210*b*, the process in step S215 is executed.

In the timing chart TC15 shown in FIG. 16, the length of the exposure period for the image V2 and the length of the exposure period for the image V4 are the same as each other. For this reason, the brightness of the image V2 and the brightness of the image V4 are the same as each other. Since the two images are the same as each other in brightness, the accuracy of measurement is improved.

Fifth Embodiment

Figure 18:
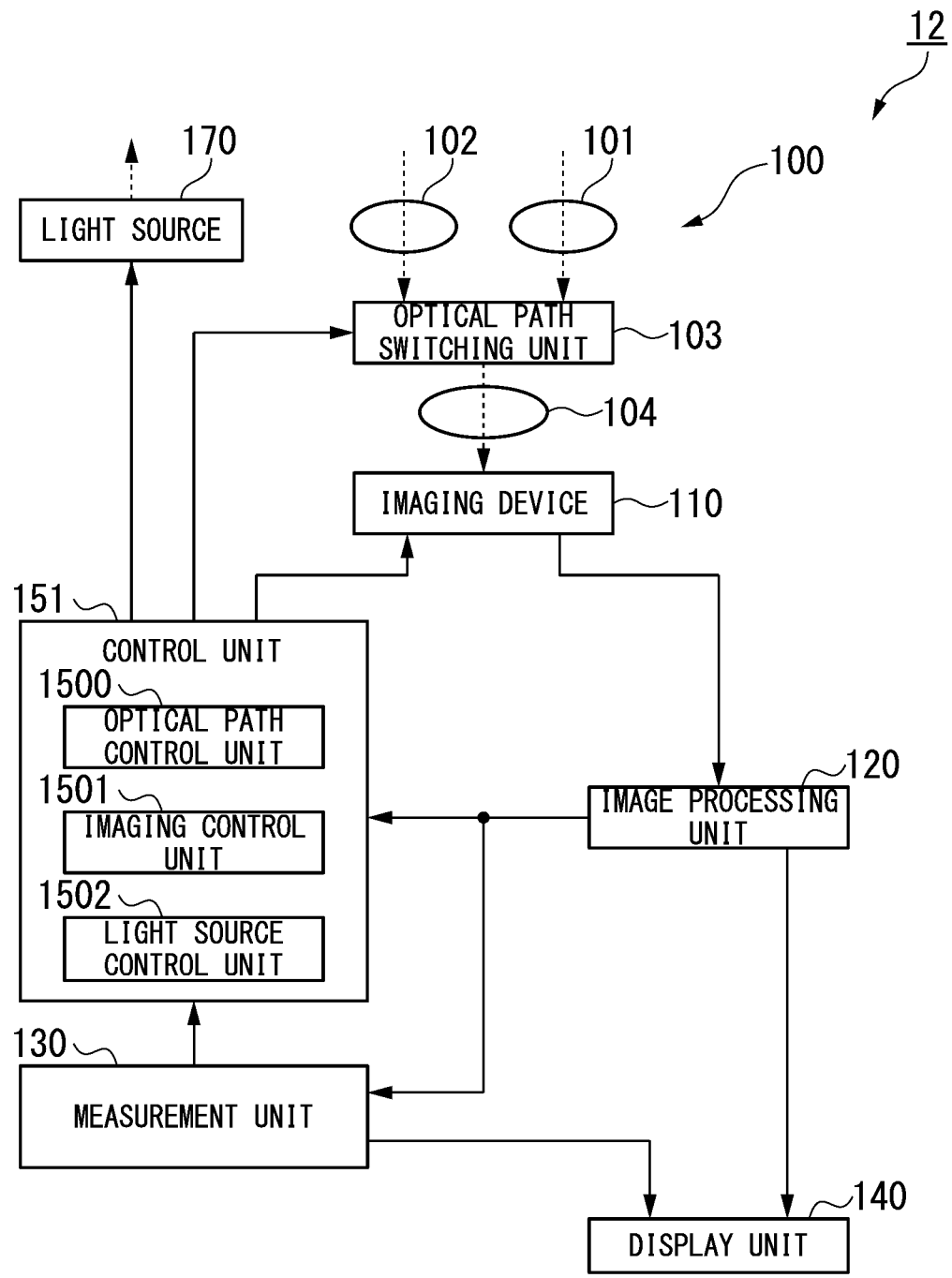
FIG. 18 is a block diagram showing a configuration of an endoscope device according to a fifth embodiment of the present invention.

FIG. 18 shows a configuration of an endoscope device 12 according to a fifth embodiment of the present invention. The same portions as portions shown in FIG. 1 will not be described. The endoscope device 12 according to the fifth embodiment uniforms the brightnesses of two images used in measurement by using a method which is different from the method in the third embodiment and is different from the method in the fourth embodiment.

The endoscope device 12 includes a light source 170 that generates illumination light with which a subject is irradiated, in addition to the configuration of the endoscope device 10 shown in FIG. 1. The light source 170 is a light-emitting element such as a light-emitting diode (LED) and a laser diode (LD). The endoscope device 12 includes a control unit 151 instead of the control unit 150 shown in FIG. 1. The control unit 151 includes a light source control unit 1502 in addition to the optical path control unit 1500 shown in FIG. 1 and the imaging control unit 1501 shown in FIG. 1. The light source control unit 1502 controls the light source 170.

The light source control unit 1502 controls the amount of light emitted from the light source 170 by controlling a current flowing in the light source 170. In a case where a current flowing in the light source 170 becomes larger, the light source 170 becomes brighter. That is, the amount of the illumination light with which a subject is irradiated becomes larger. In a case where a current flowing in the light source 170 becomes smaller, the light source 170 becomes darker. That is, the amount of the illumination light with which a subject is irradiated becomes smaller.

The image processing unit 120 determines the brightness of the image which is output from the imaging device 110. The image processing unit 120 outputs brightness information indicating the brightness of the image to the control unit 150. The light source control unit 1502 calculates the current value of the light source 170 on the basis of the brightness information. The light source control unit 1502 sets the calculated current value in the light source 170.

The measurement unit 130 executes the measurement of a subject on the basis of a first image and a second image. The first image is generated on the basis of the pixel signals of the pixels 54 exposed in a first exposure period. The second image is generated on the basis of the pixel signals of pixels 54 exposed in a second exposure period. The first exposure period includes a timing at which an instruction for the measurement of a subject is generated. The second exposure period is started after the optical path switching unit 103 completes switching between imaging conditions (imaging optical paths). The light source control unit 1502 controls the amount of light of the light source 170 in the second exposure period on the basis of the brightness of the first image.

Figure 19:
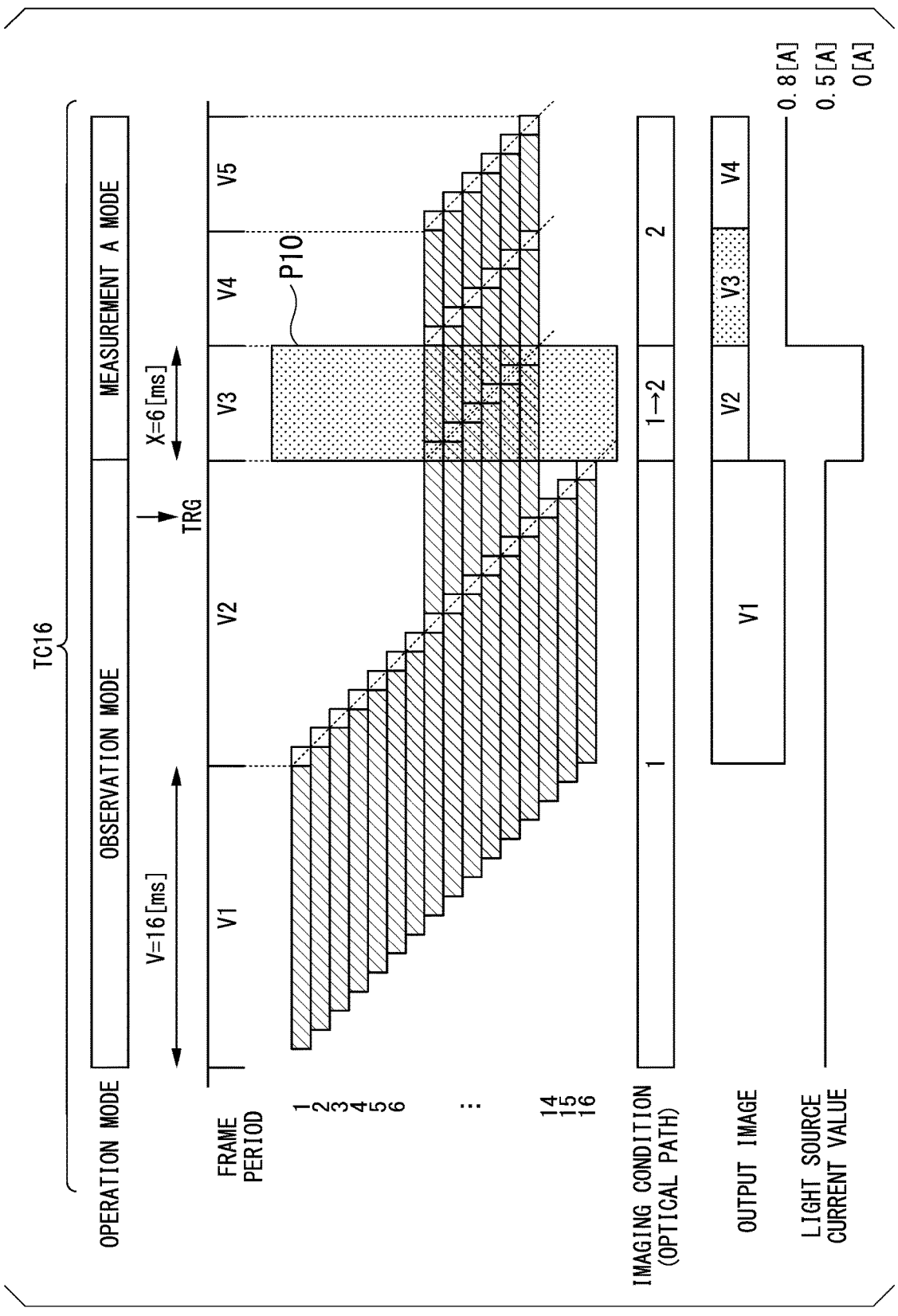
FIG. 19 is a timing chart showing an operation of an imaging device according to the fifth embodiment of the present invention.

FIG. 19 shows an operation of the imaging device 110. The operation of the imaging device 110 will be described with reference to FIG. 19. The same portions as portions shown in FIG. 4 will not be described.

A timing chart TC16 shows the operation of the imaging device 110. When the imaging device 110 operates in the observation mode, the light source control unit 1502 sets a current flowing in the light source 170 to 0.5 [A]. The light source 170 generates illumination light. When the read-out period of the pixels 54 of the eighth row in the frame period V3 is started, switching between imaging conditions, that is, switching between imaging optical paths is started. At this moment, the light source control unit 1502 sets a current flowing in the light source 170 to 0 [A]. That is, the light source control unit 1502 turns off the light source 170. While the switching between imaging optical paths is performed, the light source 170 stops the generation of the illumination light. Thereby, power consumption is reduced. While the switching between imaging optical paths is performed, the light source 170 may generate illumination light.

When the switching between imaging optical paths is started, the light source control unit 1502 calculates the current value of the light source 170 on the basis of the brightness information. The brightness information indicates the brightness of the image based on the pixel signals of the pixels 54 of the eighth row in the frame period V3. The pixel signals which are read out for the read-out period in the frame period V3 constitutes the image V2. The light source control unit 1502 calculates the current value of the light source 170 in order to equalize the brightness of the image V2 with the brightness of the image V4.

When the read-out period of the pixels 54 of the thirteenth row in the frame period V3 ends, switching between imaging conditions, that is, switching between imaging optical paths is completed. At this moment, the light source control unit 1502 sets a current flowing in the light source 170 to 0.8 [A]. The light source 170 starts the generation of the illumination light. The brightness of the image V2 and the brightness of the image V4 become the same as each other. The current value of the light source 170 is not limited to the above value.

Figure 20:
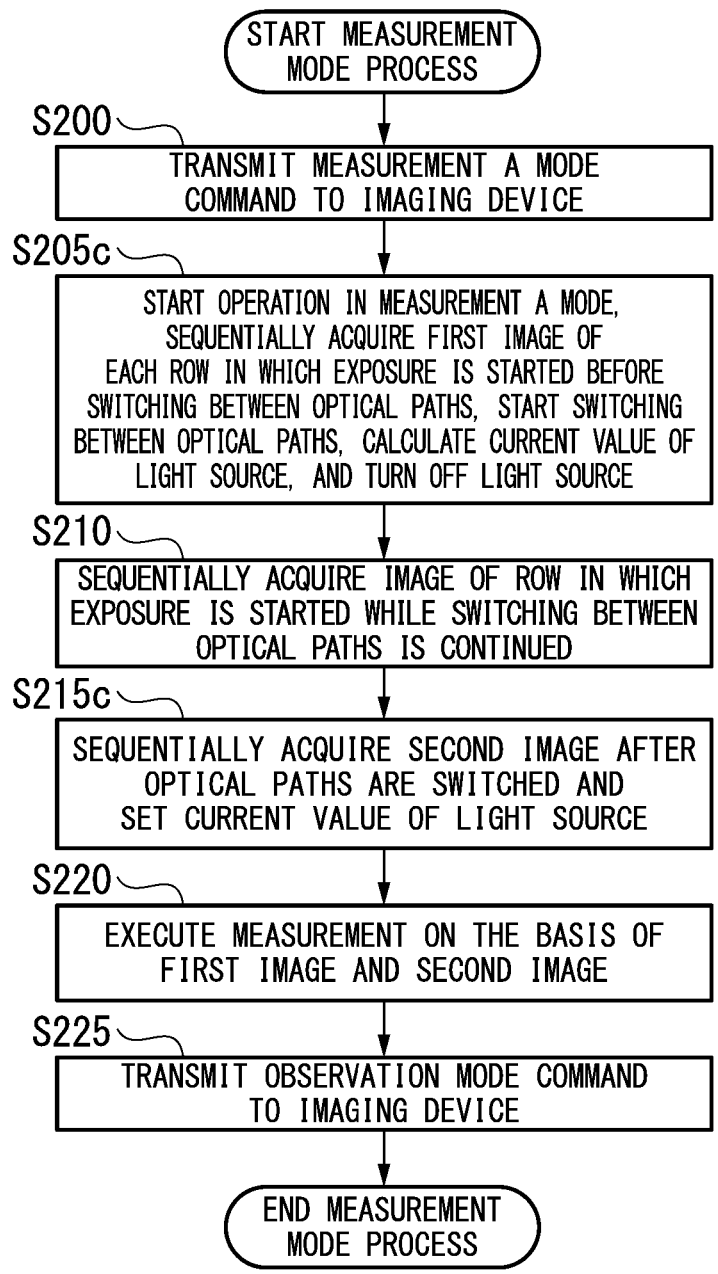
FIG. 20 is a flow chart showing a procedure of operations of the endoscope device according to the fifth embodiment of the present invention.

FIG. 20 shows the details of the measurement mode process. The operation of the endoscope device 12 in the measurement mode process will be described with reference to FIG. 20. The same process as the process shown in FIG. 7 will not be described.

After step S200, the imaging device 110 starts its operation in the measurement A mode on the basis of the measurement A mode command The imaging device 110 sequentially reads out the pixel signals of the pixels 54 of each row in which exposure is started before the switching between imaging optical paths. The pixel signals generated by exposure in the frame period V2 shown in FIG. 19 are read out. Thereby, the imaging device 110 sequentially acquires the first image based on the pixel signals of the pixels 54 of each row. The optical path control unit 1500 outputs a control signal to the optical path switching unit 103. Thereby, the optical path control unit 1500 causes the optical path switching unit 103 to start switching between imaging optical paths. The optical path switching unit 103 starts switching from the first optical path to the second optical path on the basis of the control signal from the optical path control unit 1500. The light source control unit 1502 calculates the current value of the light source 170 on the basis of the brightness information. The light source control unit 1502 turns off the light source 170 (step S205c). After step S205c, the process in step S210 is executed.

After step S210, the read-out of the pixel signal generated by exposure in the frame period V3 is completed, and switching between imaging optical paths is completed. The imaging device 110 sequentially reads out the pixel signals of the pixels 54 of a row in which exposure is started after the optical paths are switched. The pixel signals generated by exposure in the frame period V4 shown in FIG. 19 are read out. Thereby, the imaging device 110 sequentially acquires the second image based on the pixel signals of the pixels 54 of each row. When the switching between imaging optical paths is completed, the light source control unit 1502 sets the current value of the light source 170. The current value of the light source 170 is set to a value calculated in step S205c (step S215c). After step S215c, the process in step S220 is executed.

In the timing chart TC16 shown in FIG. 19, the brightness of the image V2 and the brightness of the image V4 are the same as each other. Since the two images are the same as each other in brightness, the accuracy of measurement is improved.

Sixth Embodiment

A sixth embodiment of the present invention will be described using the endoscope device 10 shown in FIG. 1. The endoscope device 10 according to the first embodiment controls the number of rows in which the imaging device 110 reads out the pixel signals in the second read-out mode. An endoscope device 10 according to the sixth embodiment controls the number of columns in which the imaging device 110 reads out the pixel signals in the second read-out mode in addition to the number of rows.

The imaging control unit 1501 controls the column number on the basis of the position of measurement coordinates. The column number is the number of columns in which the imaging device 110 reads out the pixel signals in the second read-out mode. The imaging device 110 reads out the pixel signals from the pixels 54 arranged in columns to be measured in the second read-out mode. The column to be measured includes the pixel 54 corresponding to the measurement coordinates.

The first column number is larger than the second column number. The first column number is the number of columns in which the imaging device 110 reads out the pixel signals in the first read-out mode. The second column number is the number of columns in which the imaging device 110 reads out the pixel signals in the second read-out mode.

Figure 21:
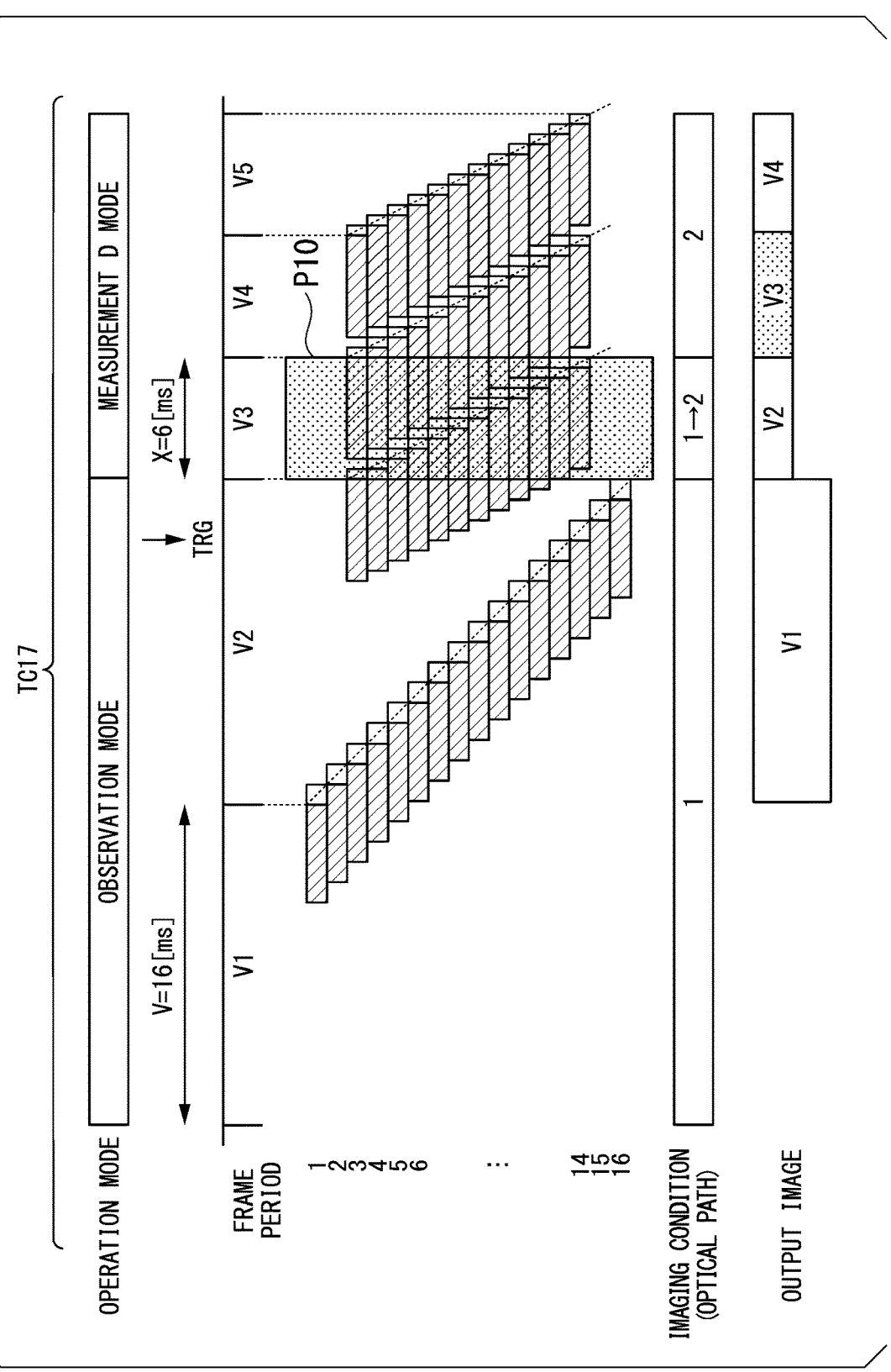
FIG. 21 is a timing chart showing an operation of an imaging device according to a sixth embodiment of the present invention.

FIG. 21 shows an operation of the imaging device 110. The operation of the imaging device 110 will be described with reference to FIG. 21. The same portions as portions shown in FIG. 12 will not be described.

A timing chart TC17 shows the operation of the imaging device 110. When the read-out period of the pixels 54 of the sixteenth row in the frame period V2 ends, the imaging control unit 1501 brings the imaging device 110 into an operation in a measurement D mode (second read-out mode). The imaging control unit 1501 outputs a command for switching the operation mode of the imaging device 110 from the observation mode to the measurement D mode to the imaging device 110. The imaging device 110 starts its operation in the measurement D mode on the basis of the command from the imaging control unit 1501. In the measurement D mode, the imaging device 110 sequentially scans six rows, and sequentially reads out the pixel signals from the pixels 54 of each row.

Figure 22:
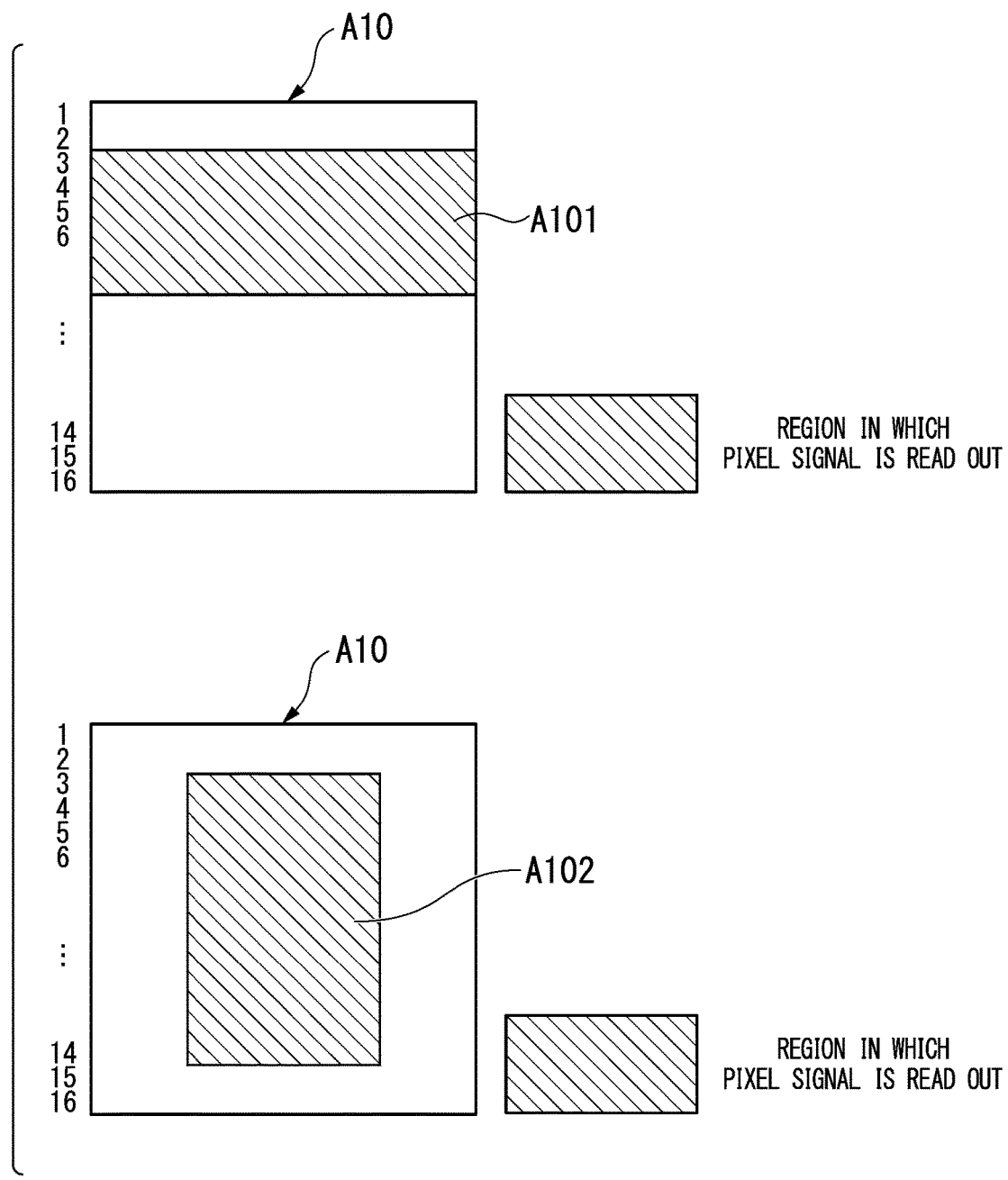
FIG. 22 is a diagram showing a region in which a pixel signal is read out in the sixth embodiment of the present invention and a region in which a pixel signal is read out in the second embodiment of the present invention.

Regions of pixels 54 in which the imaging device 110 reads out the pixel signals for the read-out period of the frame period V3 are different from each other in FIGS. 12 and 21. FIG. 22 shows a region in which a pixel signal is read out in the imaging region A10. The pixel 54 in which the imaging device 110 reads out the pixel signals in the measurement B mode of the timing chart TC13 shown in FIG. 12 is disposed in the region A101. The region A101 includes the pixels 54 of the third row to the eighth row. In each row, pixel signals are read out from the pixels 54 of all the columns The pixel 54 in which the imaging device 110 reads out the pixel signals in the measurement D mode of the timing chart TC17 shown in FIG. 21 is disposed in a region A102. The region A102 includes the pixels 54 of the third row to the fourteenth row. In each row, pixel signals are read out from the pixels 54 of some columns Pixel signals are not read out from the pixels 54 of a plurality of columns including the leftmost column of the region A102. Pixel signals are not read out from the pixels 54 of a plurality of columns including the rightmost column of the region A102.

In each row, the number of columns in which the imaging device 110 reads out the pixel signals decreases. Therefore, the read-out period of each row becomes shorter. In the timing chart TC17 shown in FIG. 21, in the switching period P10, the imaging device 110 sequentially scans twelve rows, and sequentially reads out the pixel signals from the pixels 54 of some columns in each row.

The length of the read-out period of each frame period is a product of the length of the read-out period of one row and the row number. In a case where the number of columns of the pixels 54 in the imaging region is large, and pixel signals are read out from the pixels 54 of all the columns in each row, the read-out period of each row is long. In a case where the read-out period of each row is long, it is difficult to equalize the length of the read-out period of each frame period with the length of the switch period P10. The length of the read-out period of each frame period may be longer than the length of the switching period P10. In that case, an interval between the timing of acquisition of the image V2 and the timing of acquisition of the image V4 becomes longer than the length of the switching period P10.

An example in which the length of the switching period P10 is 7 [ms] and the length of the read-out period of each row is 2 [ms] will be described below. In a case where pixel signals are read out from the pixels 54 of four rows, the length of the read-out period of one frame period is 8 [ms]. At this moment, the length of the read-out period of one frame period is different from the length of the switching period P10. On the other hand, in a case where the number of columns in which the imaging device 110 reads out the pixel signals is half the number of columns in the imaging region A10, the length of the read-out period of each row is 1 [ms]. In a case where pixel signals are read out from the pixels 54 of seven rows, the length of the read-out period of one frame period is 7 [ms]. Therefore, it is possible to equalize the length of the read-out period of one frame period with the length of the switch period P10.

In the measurement D mode shown in FIG. 21, the length of the read-out period of each frame period is the same as the length of the switching period P10. In the timing chart TC17 shown in FIG. 21, the read-out period of each row is short. Therefore, it is easy to equalize the length of the read-out period of each frame period with the length of the switch period P10.

The pixel signals generated in the exposure period of the pixels 54 of each row in the frame period V3 are read out in the frame period V4. The read-out period of the pixels 54 of the fourteenth row in the frame period V3 ends. At this moment, the exposure period of the pixels 54 of the third row in the frame period V3 ends, and the read-out period of the pixels 54 of the third row in the frame period V4 is started. At this moment, switching between imaging conditions, that is, switching between imaging optical paths is completed. The imaging optical path is the second optical path. The imaging device 110 sequentially starts the read-out periods of the pixels 54 of the third row to the fourteenth row, and sequentially reads out the pixel signals of the pixels 54 of the third row to the fourteenth row. An operation in which the imaging device 110 reads out the pixel signals in the frame period V4 is the same as the operation in which the imaging device 110 reads out the pixel signals in the frame period V3. The imaging device 110 continues the same operation as the operation for the frame period V3 in the frame period V4 and the frame period V5.

In the timing chart TC17 shown in FIG. 21, an interval in which two images for measurement are acquired becomes shorter. A blur between two images used in measurement is reduced, and a measurement error caused by the influence of the blur decreases. That is, the accuracy of measurement is improved.

Seventh Embodiment

Figures 23, 24:
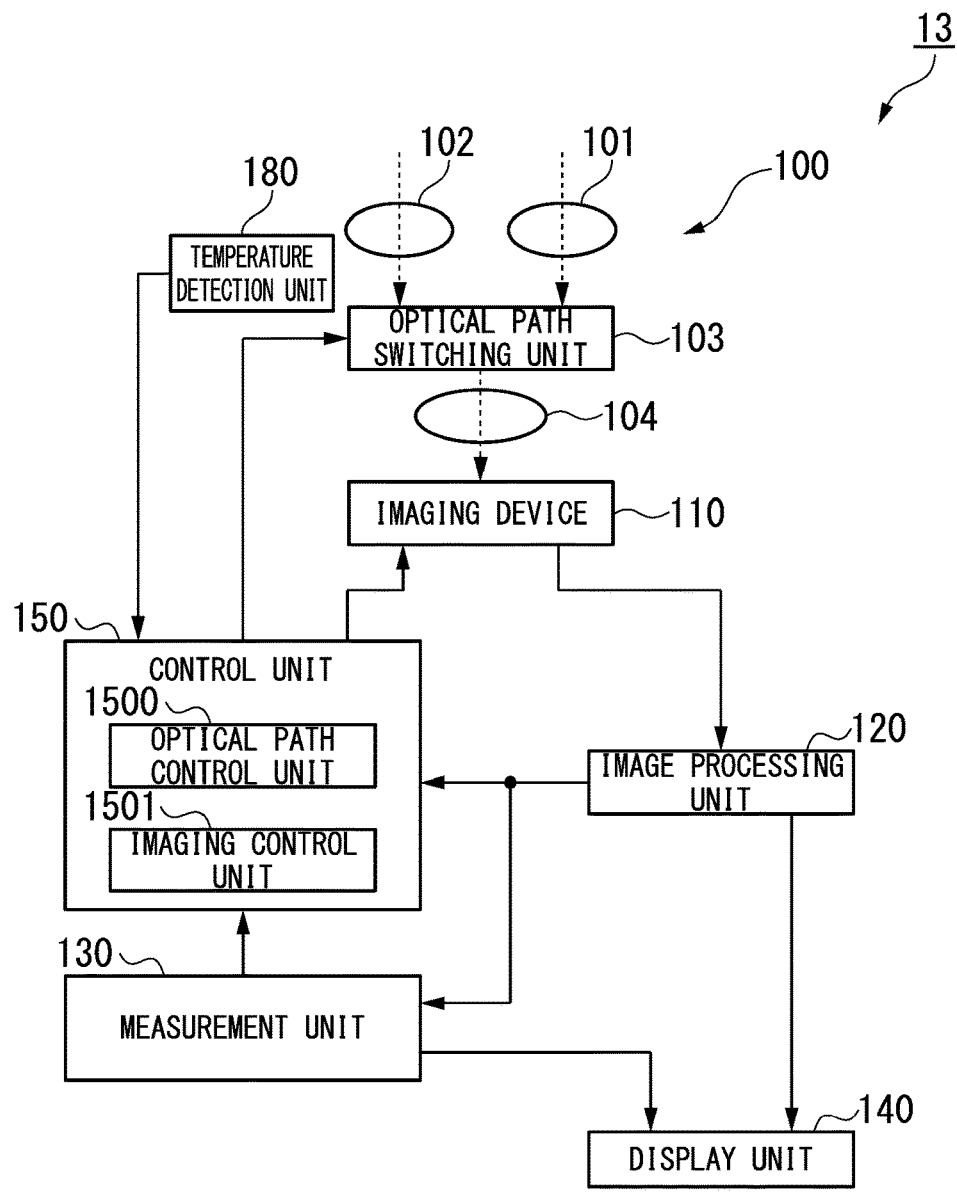
FIG. 23 is a block diagram showing a configuration of an endoscope device according to a seventh embodiment of the present invention.
FIG. 24 is a diagram showing content of a table indicating a relationship between a temperature and an optical path switching time in the seventh embodiment of the present invention.

FIG. 23 shows a configuration of an endoscope device 13 according to a seventh embodiment of the present invention. The same portions as portions shown in FIG. 1 will not be described. In the endoscope device 10 according to the first embodiment, a time period required for the switching between imaging optical paths is fixed. In the endoscope device 13 according to the seventh embodiment, a time period required for the switching between imaging optical paths varies according to a temperature.

The endoscope device 13 includes a temperature detection unit 180 in addition to the configuration of the endoscope device 10 shown in FIG. 1. The temperature detection unit 180 detects the temperature of the optical path switching unit 103. For example, the temperature detection unit 180 is disposed in the vicinity of the optical path switching unit 103.

The imaging control unit 1501 controls a row number on the basis of an estimated time. The estimated time is a time period estimated in the switching between imaging conditions (imaging optical paths) by the optical path switching unit 103. The estimated time is a time period required for the switching between imaging optical paths. The row number is the number of rows in which the imaging device 110 reads out the pixel signals in the second read-out mode. The imaging control unit 1501 controls the row number on the basis of a temperature detected by the temperature detection unit 180.

The movement of the optical path switching unit 103 has a feature dependent on a temperature. Therefore, a time period required for the switching between imaging optical paths is dependent on a temperature. For example, a table indicating a relationship between a temperature and an optical path switching time is stored in a read only memory (ROM). The optical path switching time is a time period required for the switching between imaging optical paths, and is the above estimated time. The optical path control unit 1500 determines the optical path switching time on the basis of temperature information and the table.

FIG. 24 shows content of a table indicating a relationship between a temperature and an optical path switching time. In the example shown in FIG. 24, an optical path switching time is associated with each of three temperatures. An optical path switching time associated with temperature t1 is four milliseconds. An optical path switching time associated with temperature t2 is five milliseconds. An optical path switching time associated with temperature t3 is six milliseconds. For example, in a case where the temperature information indicates the temperature t3, the optical path control unit 1500 determines an optical path switching time to be six milliseconds. The imaging control unit 1501 controls the row number on the basis of an optical path switching time determined by the optical path control unit 1500. The content of the table indicating a relationship between a temperature and an optical path switching time is not limited to the content shown in FIG. 24. The optical path control unit 1500 may calculate an optical path switching time on the basis of a function indicating a relationship between a temperature and an optical path switching time. The imaging control unit 1501 may calculate an optical path switching time.

Figure 25:
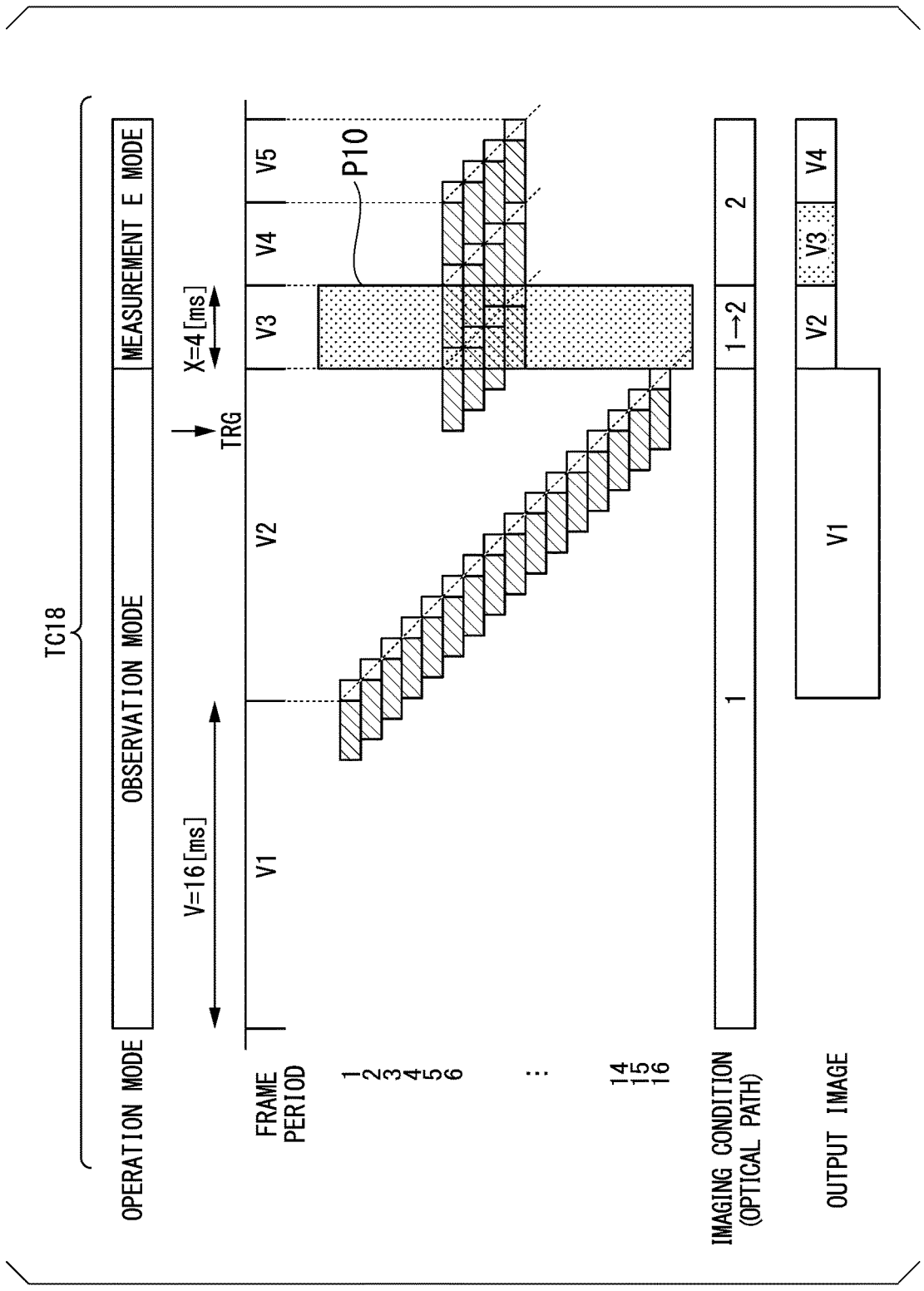
FIG. 25 is a timing chart showing an operation of an imaging device according to the seventh embodiment of the present invention.

FIG. 25 shows an operation of the imaging device 110. The operation of the imaging device 110 will be described with reference to FIG. 25. The same portions as portions shown in FIG. 4 will not be described.

A timing chart TC18 shows the operation of the imaging device 110. When the read-out period of the pixels 54 of the sixteenth row in the frame period V2 ends, the imaging control unit 1501 brings the imaging device 110 into an operation in a measurement E mode (second read-out mode). The imaging control unit 1501 outputs a command for switching the operation mode of the imaging device 110 from the observation mode to the measurement E mode to the imaging device 110. The imaging device 110 starts its operation in the measurement E mode on the basis of the command from the imaging control unit 1501.

The optical path control unit 1500 determines an optical path switching time. The imaging control unit 1501 determines the number of rows in which the imaging device 110 reads out the pixel signals on the basis of the optical path switching time. For example, in a case where the temperature is t1, the optical path switching time is four milliseconds. The imaging control unit 1501 determines the row number to be four. In the measurement E mode, the imaging control unit 1501 causes the imaging device 110 to read out the pixel signals from the pixels 54 of four rows. In the measurement E mode, the imaging device 110 sequentially scans four rows, and sequentially reads out the pixel signals from the pixels 54 of each row.

Figure 26:
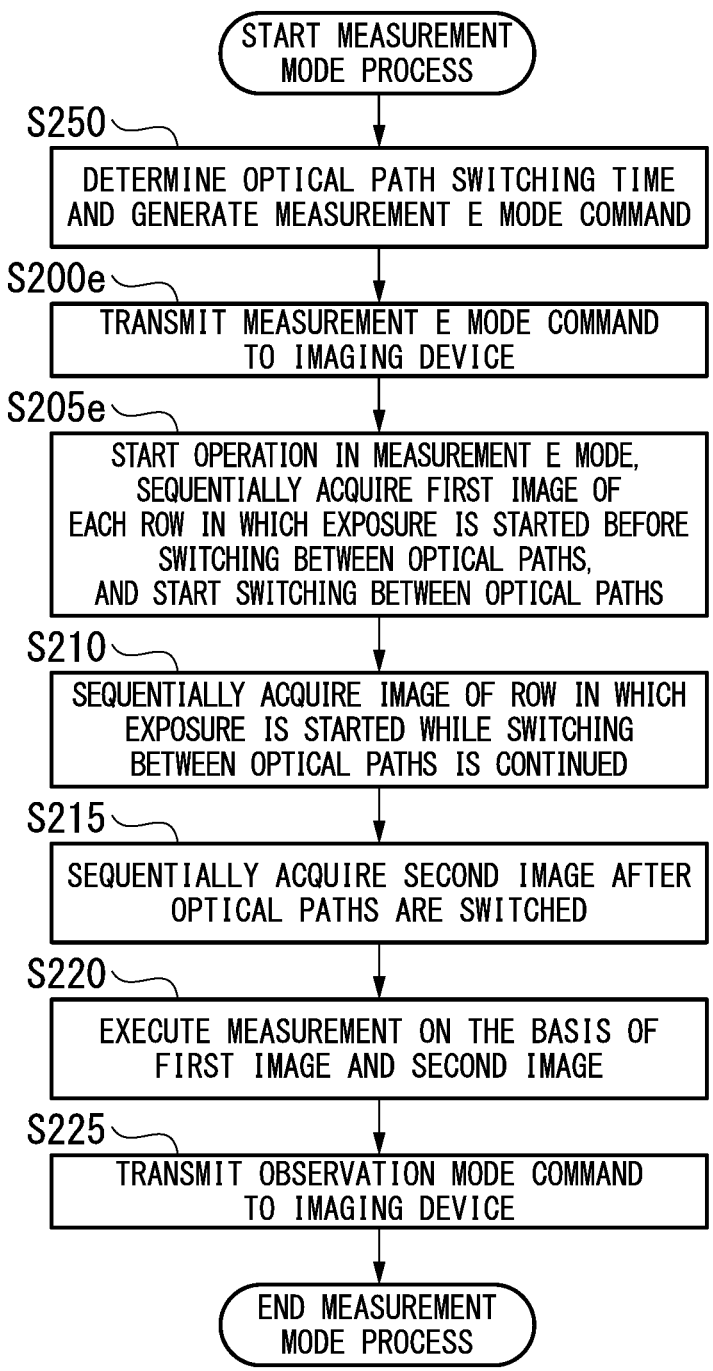
FIG. 26 is a flow chart showing a procedure of operations of the endoscope device according to the seventh embodiment of the present invention.

FIG. 26 shows the details of the measurement mode process. The operation of the endoscope device 13 in the measurement mode process will be described with reference to FIG. 26. The same process as the process shown in FIG. 7 will not be described.

The optical path control unit 1500 determines an optical path switching time. The imaging control unit 1501 determines the number of rows in which the imaging device 110 reads out the pixel signals on the basis of the optical path switching time. The imaging control unit 1501 generates a measurement E mode command. The measurement E mode command includes information indicating the number of rows in which the imaging device 110 reads out the pixel signals (step S250).

After step S250, the imaging control unit 1501 transmits the measurement E mode command to the imaging device 110. Thereby, the imaging control unit 1501 brings the imaging device 110 into an operation in the measurement E mode (step S200e).

After step S200e, the imaging device 110 starts its operation in the measurement E mode on the basis of the measurement E mode command. The imaging device 110 sequentially reads out the pixel signals of the pixels 54 of each row in which exposure is started before the switching between imaging optical paths. The pixel signals generated by exposure in the frame period V2 shown in FIG. 25 are read out. Thereby, the imaging device 110 sequentially acquires the first image based on the pixel signals of the pixels 54 of each row. The optical path control unit 1500 outputs a control signal to the optical path switching unit 103. Thereby, the optical path control unit 1500 causes the optical path switching unit 103 to start switching between imaging optical paths. The optical path switching unit 103 starts switching from the first optical path to the second optical path on the basis of the control signal from the optical path control unit 1500 (step S205e). After step S205e, the process in step S210 is executed.

The endoscope device 13 can shorten the time interval of imaging under a plurality of imaging conditions on the basis of the temperature of the optical path switching unit 103. Therefore, an interval in which two images for measurement are acquired becomes shorter. A blur between two images used in measurement is reduced, and a measurement error caused by the influence of the blur decreases. That is, the accuracy of measurement is improved.

Eighth Embodiment

An eighth embodiment of the present invention will be described using the endoscope device 10 shown in FIG. 1. In the endoscope device 10, the imaging optical path is switched from the first optical path to the second optical path. Thereafter, the imaging optical path is switched from the second optical path to the first optical path.

A plurality of imaging conditions include a first imaging condition and a second imaging condition. The first imaging condition and the second imaging condition are different from each other. The imaging control unit 1501 controls the third row number on the basis of a first estimated time. The first estimated time is a time period estimated in the switching between imaging conditions from the first imaging condition to the second imaging condition by the optical path control unit 1500. The third row number is the number of rows in which the imaging device 110 reads out the pixel signals in the second read-out mode. The imaging control unit 1501 controls the fourth row number on the basis of a second estimated time. The second estimated time is a time period estimated in the switching between imaging conditions from the second imaging condition to the first imaging condition by the optical path control unit 1500. The fourth row number is the number of rows in which the imaging device 110 reads out the pixel signals in the second read-out mode. The first estimated time and the second estimated time are known time periods required for the switching between imaging optical paths. For example, the first estimated time and the second estimated time are different from each other. The third row number and the fourth row number are different from each other. The first estimated time and the second estimated time may be the same as each other. The third row number and the fourth row number may be the same as each other.

The measurement unit 130 executes the measurement of a subject on the basis of a first image and a second image.

The first image is generated on the basis of the pixel signals of the pixels 54 exposed in any one of the first exposure period and the third exposure period. The second image is generated on the basis of the pixel signals of the pixels 54 exposed in the second exposure period. The first exposure period includes a timing at which an instruction for the measurement of a subject is generated. The second exposure period is started after the optical path switching unit 103 completes first switching. The first switching is switching between imaging conditions (imaging optical paths) from the first imaging condition to the second imaging condition. The second exposure period ends before the optical path switching unit 103 starts second switching. The second switching is switching between imaging conditions (imaging optical paths) from the second imaging condition to the first imaging condition. The third exposure period is started after the optical path switching unit 103 completes the second switching.

In a case where a time period required for the second switching is shorter than a time period required for the first switching, the first image is generated on the basis of the pixel signals of the pixels 54 exposed in the third exposure period. In a case where a time period required for the first switching is shorter than a time period required for the second switching, the first image is generated on the basis of the pixel signals of the pixels 54 exposed in the first exposure period.

Figure 27:
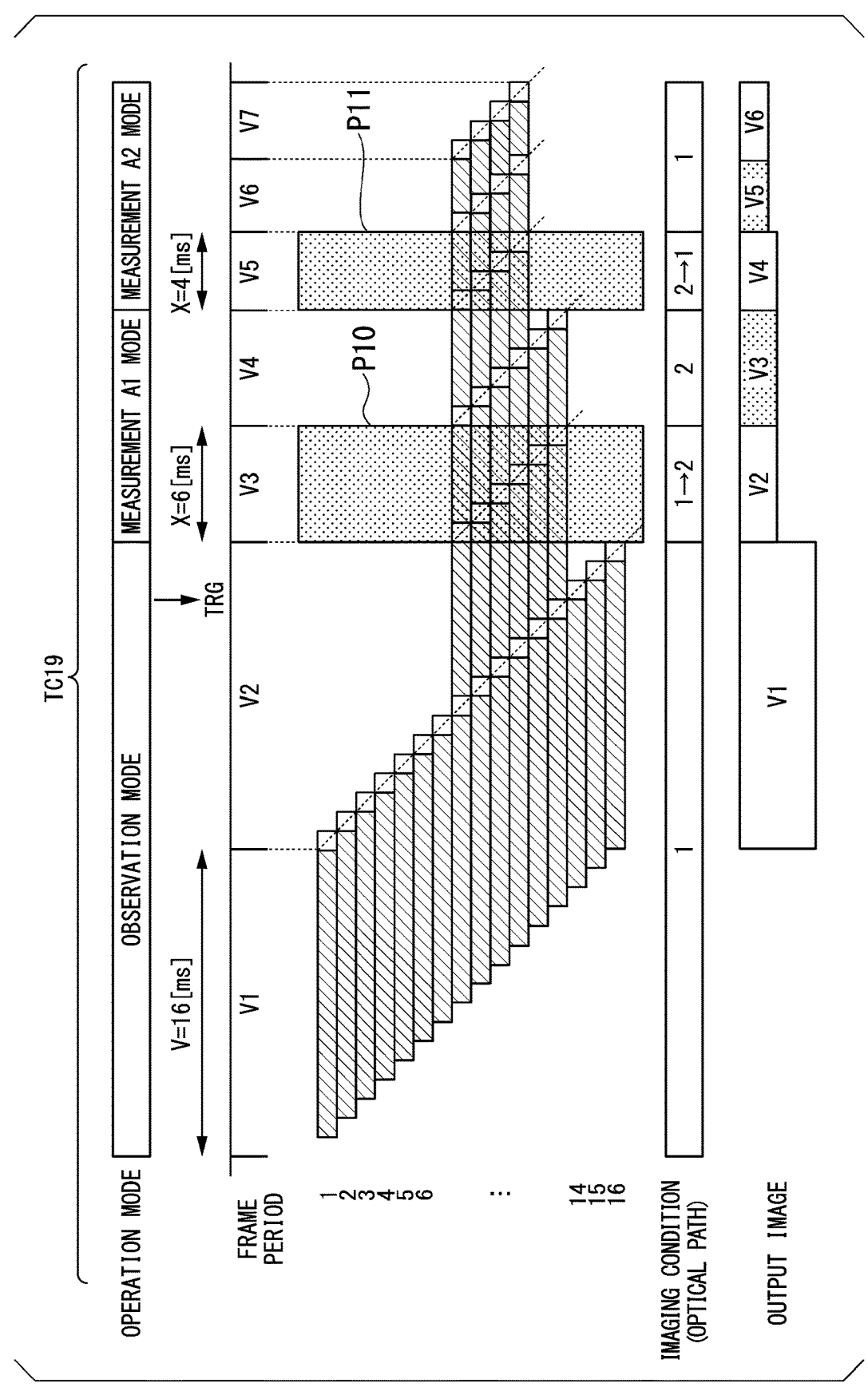
FIG. 27 is a timing chart showing an operation of an imaging device according to an eighth embodiment of the present invention.

FIG. 27 shows an operation of the imaging device 110. The operation of the imaging device 110 will be described with reference to FIG. 27. The same portions as portions shown in FIG. 8 will not be described.

A timing chart TC19 shows the operation of the imaging device 110. The imaging optical path is switched from the first optical path to the second optical path. After the imaging optical path is switched from the first optical path to the second optical path, the imaging optical path is switched from the second optical path to the first optical path. A time period required for switching from the first optical path to the second optical path and a time period required for switching from the second optical path to the first optical path are different from each other. For example, the time period required for switching from the first optical path to the second optical path is six milliseconds. The time period required for switching the second optical path to the first optical path is four milliseconds.

For example, a table indicating a relationship between an imaging optical path and an optical path switching time is stored in a read only memory (ROM). The imaging optical path is at least one of a current first imaging optical path and a second imaging optical path which is set subsequently to the first imaging optical path. The optical path control unit 1500 determines an optical path switching time on the basis of the table.

When the read-out period of the pixels 54 of the sixteenth row in the frame period V2 ends, the imaging control unit 1501 brings imaging device 110 into an operation in a measurement A1 mode (second read-out mode). The imaging control unit 1501 outputs a command for switching the operation mode of the imaging device 110 from the observation mode to the measurement A1 mode to the imaging device 110. The imaging device 110 starts its operation in the measurement A1 mode on the basis of the command from the imaging control unit 1501.

The optical path control unit 1500 determines an optical path switching time. The imaging control unit 1501 determines the number of rows in which the imaging device 110 reads out the pixel signals on the basis of the optical path switching time. Since the current imaging optical path is the first optical path (first imaging condition), the optical path switching time (first estimated time) is six milliseconds. The imaging control unit 1501 determines the row number (third row number) to be six. In the measurement A1 mode, the imaging control unit 1501 causes the imaging device 110 to read out the pixel signals from the pixels 54 of six rows. In the measurement A1 mode, the imaging device 110 sequentially scans six rows, and sequentially reads out the pixel signals from the pixels 54 of each row.

When the read-out period of the pixels 54 of the thirteenth row in the frame period V4 ends, the imaging control unit 1501 brings the imaging device 110 into an operation in a measurement A2 mode (second read-out mode). The imaging control unit 1501 outputs a command for switching the operation mode of the imaging device 110 from the measurement A1 mode to the measurement A2 mode to the imaging device 110. The imaging device 110 starts its operation in the measurement A2 mode on the basis of the command from the imaging control unit 1501.

The optical path control unit 1500 determines an optical path switching time. The imaging control unit 1501 determines the number of rows in which the imaging device 110 reads out the pixel signals on the basis of the optical path switching time. Since the current imaging optical path is the second optical path (second imaging condition), the optical path switching time (second estimated time) is four milliseconds. The imaging control unit 1501 determines the row number (fourth row number) to be four. In the measurement A2 mode, the imaging control unit 1501 causes the imaging device 110 to read out the pixel signals from the pixels 54 of four rows. In the measurement A2 mode, the imaging device 110 sequentially scans four rows, and sequentially reads out the pixel signals from the pixels 54 of each row.

The image V2 includes the pixel signals which are read out from the pixels 54 of six rows after the exposure period (first exposure period) in the frame period V2. The image V2 includes the pixel signals which are read out in the measurement A1 mode by the imaging device 110. The size of the image V3 is the same as the size of the image V2. The image V4 includes the pixel signals which are read out from the pixels 54 of four rows after the exposure period (second exposure period) in the frame period V4. The image V4 includes the pixel signals which are read out in the measurement A2 mode by the imaging device 110. The sizes of the image V5 and the image V6 are the same as the size of the image V4.

In the measurement A1 mode shown in FIG. 27, the imaging device 110 outputs the image V2 and the image V3. The exposure period of the pixels 54 of the eighth row in the frame period V2 does not overlap the switching period P10. The pixel signals generated in the pixels 54 of the eighth row in the frame period V2 are based on the first optical image corresponding to the first optical path.

The exposure period of the pixels 54 of the eighth row in the frame period V3 overlaps the switching period P10. The pixel signals generated in the pixels 54 of the eighth row in the frame period V3 are based on the first optical image corresponding to the first optical path and the second optical image corresponding to the second optical path. For this reason, the image V3 is not suitable for measurement.

The exposure period of the pixels 54 of the eighth row in the frame period V4 does not overlap the switching period P10. The pixel signals generated in the pixels 54 of the eighth row in the frame period V4 are based on the second optical image corresponding to the second optical path.

The exposure period of the pixels 54 of the eighth row in the frame period V5 overlaps the switching period P11. The pixel signals generated in the pixels 54 of the eighth row in the frame period V5 are based on the first optical image and the second optical image. For this reason, the image V5 is not suitable for measurement.

The exposure period (third exposure period) of the pixels 54 of the eighth row in the frame period V6 does not overlap the switching period P11. The pixel signals generated in the pixels 54 of the eighth row in the frame period V6 are based on the first optical image corresponding to the first optical path.

The image V2 which is a first image, the image V4 which is a second image, and the image V6 which is a first image can be used in measurement. A first interval is larger than a second interval. The first interval is an interval between a timing of acquisition of the image V2 and a timing of acquisition of the image V4. The second interval is an interval between a timing of acquisition of the image V4 and a timing of acquisition of the image V6. The control unit 150 causes the measurement unit 130 to execute measurement in which the image V4 and the image V6 are used. The measurement unit 130 executes the measurement of a subject on the basis of the image V4 and the image V6.

The exposure periods of the pixels 54 of the ninth row to the eleventh row in the frame period V4 overlap the switching period P11. In the image V4, the pixel signals of the pixels 54 of the eighth row can be used in measurement, but the pixel signals of the pixels 54 of the ninth row to the eleventh row are not suitable for measurement. The measurement unit 130 performs measurement using the pixel signals of the pixels 54 of the eighth row in the image V4 and the pixel signals of the pixels 54 of the eighth row in the image V6.

Figure 28:
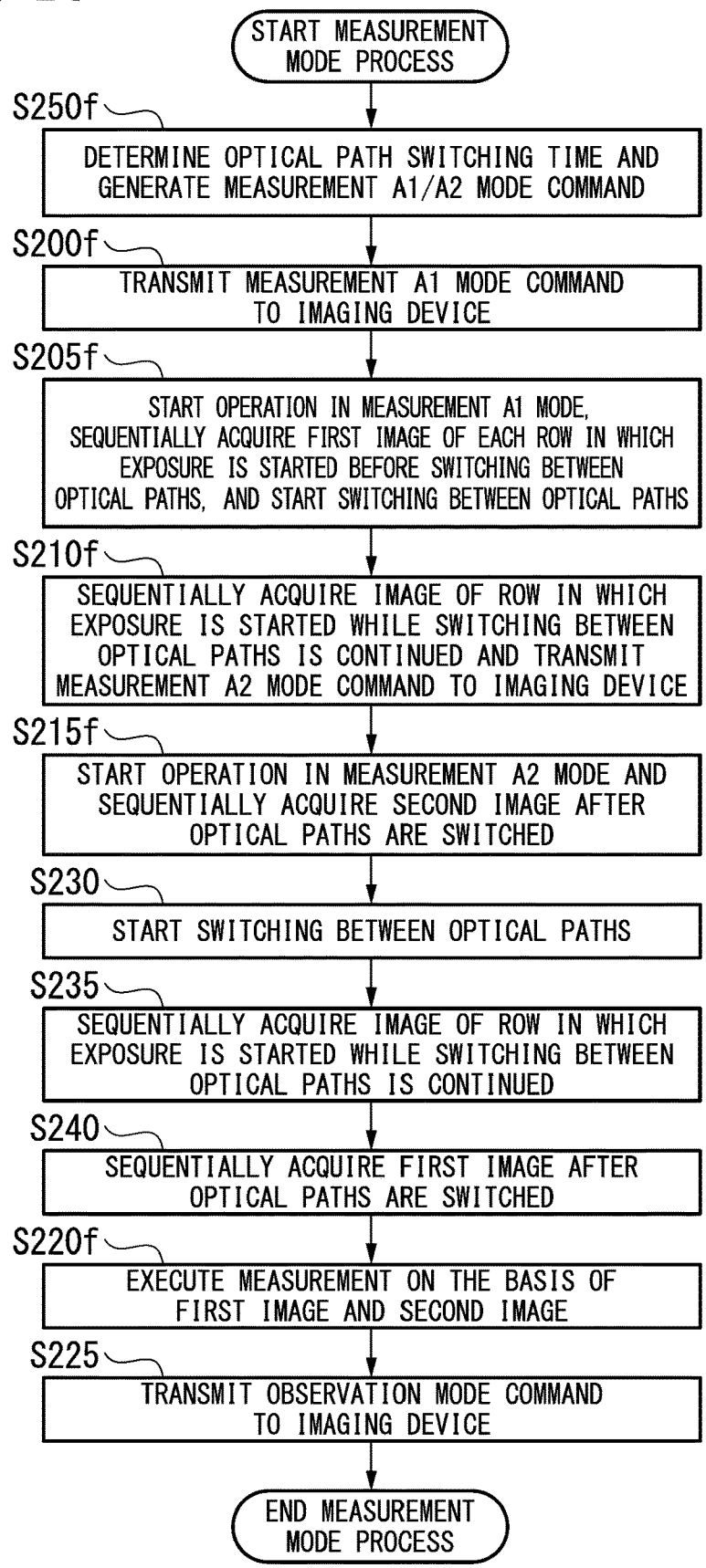
FIG. 28 is a flow chart showing a procedure of operations of the endoscope device according to the eighth embodiment of the present invention.

FIG. 28 shows the details of the measurement mode process. The operation of the endoscope device 10 in the measurement mode process will be described with reference to FIG. 28. The same process as the process shown in FIG. 9 will not be described.

The optical path control unit 1500 determines a first optical path switching time required for switching from the first optical path to the second optical path. The optical path control unit 1500 determines a second optical path switching time required for switching from the second optical path to the first optical path. The imaging control unit 1501 determines the number of rows in which the imaging device 110 reads out the pixel signals on the basis of the first optical path switching time. The imaging control unit 1501 determines the number of rows in which the imaging device 110 reads out the pixel signals on the basis of the second optical path switching time. The imaging control unit 1501 generates a measurement A1 mode command The measurement A1 mode command includes information indicating the number of rows in which the imaging device 110 reads out the pixel signals in the measurement A1 mode. The imaging control unit 1501 generates a measurement A2 mode command The measurement A2 mode command includes information indicating the number of rows in which the imaging device 110 reads out the pixel signals in the measurement A2 mode (step S250f).

After step S250f, the imaging control unit 1501 transmits the measurement A1 mode command to the imaging device 110. Thereby, the imaging control unit 1501 brings the imaging device 110 into an operation in the measurement A1 mode (step S200f).

After step S200f, the imaging device 110 starts its operation in the measurement A1 mode on the basis of the measurement A1 mode command The imaging device 110 sequentially reads out the pixel signals of the pixels 54 of each row in which exposure is started before the switching between imaging optical paths. The pixel signals generated by exposure in the frame period V2 shown in FIG. 27 are read out. Thereby, the imaging device 110 sequentially acquires the first image based on the pixel signals of the pixels 54 of each row. The optical path control unit 1500 outputs a control signal to the optical path switching unit 103. Thereby, the optical path control unit 1500 causes the optical path switching unit 103 to start switching between imaging optical paths. The optical path switching unit 103 starts switching from the first optical path to the second optical path on the basis of the control signal from the optical path control unit 1500 (step S205f).

After step S205f, the imaging device 110 sequentially reads out the pixel signals of the pixels 54 of a row in which exposure is started while the switching between optical paths is continued. The pixel signals generated by exposure in the frame period V3 shown in FIG. 27 are read out. Thereby, the imaging device 110 sequentially acquires an image based on the pixel signals of the pixels 54 of each row. The imaging control unit 1501 transmits the measurement A2 mode command to the imaging device 110. Thereby, the imaging control unit 1501 brings the imaging device 110 into an operation in the measurement A2 mode (step S210f).

After step S210f, the imaging device 110 starts its operation in the measurement A2 mode on the basis of the measurement A2 mode command After step S210f, the read-out of the pixel signal generated by exposure in the frame period V3 is completed, and the switching between imaging optical paths is completed. The imaging device 110 sequentially reads out the pixel signals of the pixels 54 of a row in which exposure is started after the optical paths are switched. The pixel signals generated by exposure in the frame period V4 shown in FIG. 27 are read out. Thereby, the imaging device 110 sequentially acquires a second image based on the pixel signals of the pixels 54 of each row (step S215f). After step S215f, the process in step S230 is executed.

After step S235, the read-out of the pixel signal generated by exposure in the frame period V5 is completed, and the switching between imaging optical paths is completed. The imaging device 110 sequentially reads out the pixel signals of the pixels 54 of a row in which exposure is started after the optical paths are switched. The pixel signals generated by exposure in the frame period V6 shown in FIG. 27 are read out. Thereby, the imaging device 110 sequentially acquires a first image based on the pixel signals of the pixels 54 of each row (step S240).

After step S240, the control unit 150 causes the measurement unit 130 to execute measurement in which the first image and the second image are used. The first image is the image V6 shown in FIG. 27. The second image is the image V4 shown in FIG. 27. The measurement unit 130 executes the measurement of a subject on the basis of the first image and the second image which are output from the image processing unit 120. The display unit 140 displays a measurement result (step S220f). After step S220f, the process in step S225 is executed.

The endoscope device 13 according to the seventh embodiment may execute the same operation as the operation shown in FIG. 27. The number of rows in which the imaging device 110 reads out the pixel signals in the switching period P10 and the number of rows in which the imaging device 110 reads out the pixel signals in the switching period P11 may be determined on the basis of the temperature of the optical path switching unit 103.

The endoscope device 10 can shorten the time interval of imaging under a plurality of imaging conditions. Therefore, an interval in which two images for measurement are acquired becomes shorter. A blur between two images used in measurement is reduced, and a measurement error caused by the influence of the blur decreases. That is, the accuracy of measurement is improved.

Ninth Embodiment

A ninth embodiment of the present invention will be described using the endoscope device 10 shown in FIG. 1. The endoscope device 10 performs measurement using the pixel signals generated in the pixels 54 of a plurality of rows.

The measurement unit 130 executes the measurement of a subject on the basis of the pixel signals of a measurement row in an image. The measurement row includes at least two rows which are continuous. Any one of the at least two rows includes the pixel 54 corresponding to measurement coordinates. When the imaging device 110 reads out the pixel signals from the pixels 54 disposed in the measurement row in the second read-out mode, the imaging control unit 1501 causes the optical path switching unit 103 to switch imaging conditions (imaging optical paths).

Figure 29:
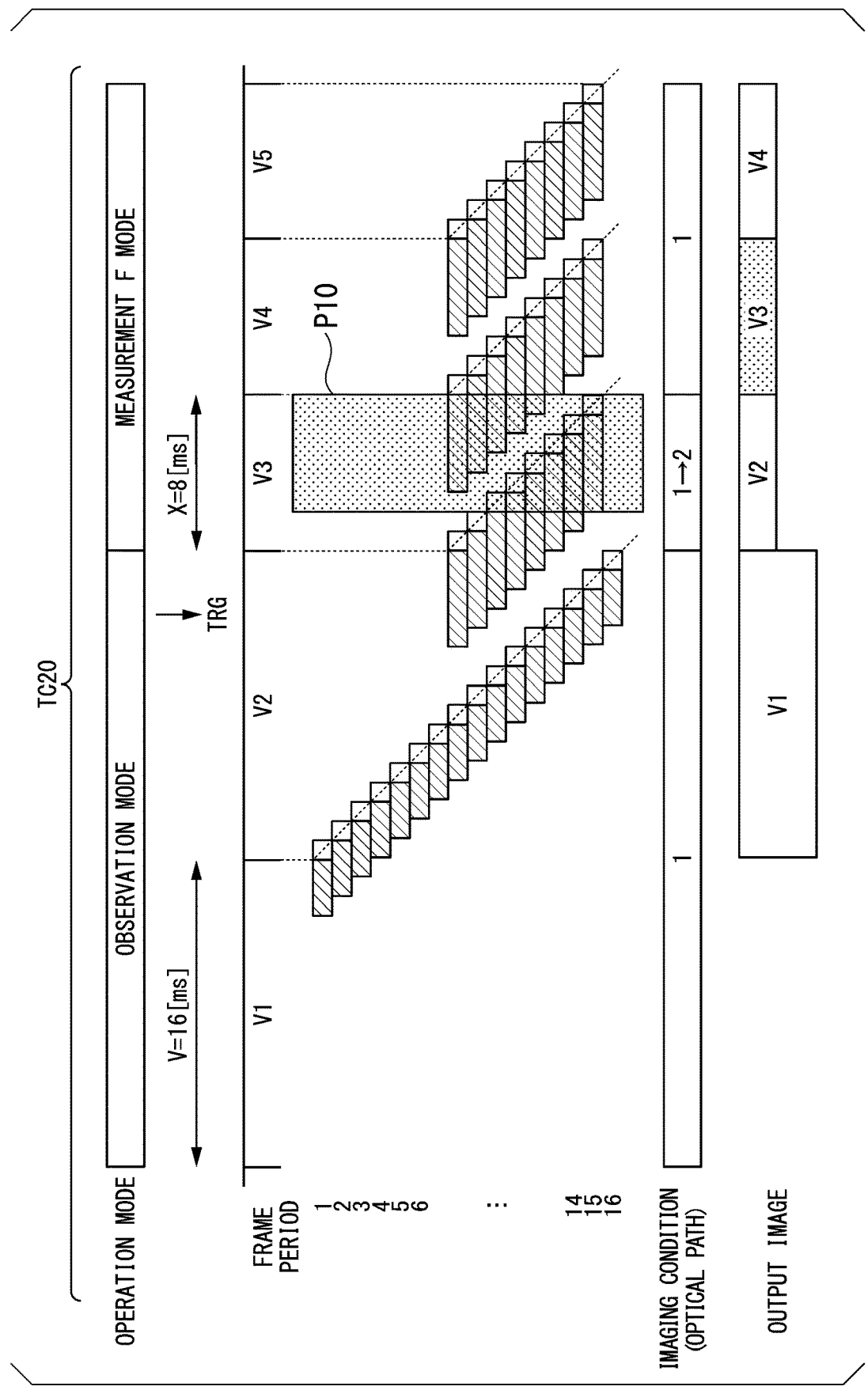
FIG. 29 is a timing chart showing an operation of an imaging device according to a ninth embodiment of the present invention.

FIG. 29 shows an operation of the imaging device 110. The operation of the imaging device 110 will be described with reference to FIG. 29. The same portions as portions shown in FIG. 4 will not be described.

A timing chart TC20 shows the operation of the imaging device 110. In the example shown in FIG. 29, the measurement row is the eighth row to the tenth row. When the read-out period of the pixels 54 of the sixteenth row in the frame period V2 ends the, imaging control unit 1501 brings the imaging device 110 into an operation in a measurement F mode (second read-out mode). The imaging control unit 1501 outputs a command for switching the operation mode of the imaging device 110 from the observation mode to the measurement F mode to the imaging device 110. The imaging device 110 starts its operation in the measurement F mode on the basis of the command from the imaging control unit 1501. In the measurement F mode, the imaging device 110 sequentially scans eight rows, and sequentially reads out the pixel signals from the pixels 54 of each row.

In the frame period V3, the imaging device 110 sequentially starts the read-out periods of the pixels 54 of the eighth row to the fifteenth row, and sequentially reads out the pixel signals of the pixels 54 of the eighth row to the fifteenth row. The pixels 54 of the eighth row to the fifteenth row are sequentially reset, and the exposure periods of the pixels 54 of the eighth row to the fifteenth row in the frame period V3 are sequentially started.

When the read-out period of the pixels 54 of the tenth row in the frame period V3 is started, switching between imaging conditions, that is, switching between imaging optical paths is started. The imaging control unit 1501 outputs a control signal for the switching between imaging optical paths to the optical path switching unit 103. Thereby, the optical path control unit 1500 causes the optical path switching unit 103 to switch imaging optical paths. The optical path switching unit 103 starts switching from the first optical path to the second optical path on the basis of the control signal from the imaging control unit 1501. The frame period V3 subsequent to the frame period V2 in which a measurement trigger is generated is started. When a predetermined time period has elapsed from the start of the frame period V3, the optical path switching unit 103 starts the switching between imaging optical paths.

The pixel signals generated in the exposure period of the pixels 54 of each row in the frame period V3 are read out in the frame period V4. The read-out period of the pixels 54 of the fifteenth row in the frame period V3 ends. At this moment, the exposure period of the pixels 54 of the eighth row in the frame period V3 ends, and the read-out period of the pixels 54 of the eighth row in the frame period V4 is started. At this moment, switching between imaging conditions, that is, switching between imaging optical paths is completed. The imaging optical path is a second optical path. The imaging device 110 sequentially starts the read-out periods of the pixels 54 of the eighth row to the fifteenth row, and sequentially reads out the pixel signals of the pixels 54 of the eighth row to the fifteenth row. An operation in which the imaging device 110 reads out the pixel signals in the frame period V4 is the same as the operation in which the imaging device 110 reads out the pixel signals in the frame period V3. The imaging device 110 continues the same operation as the operation for the frame period V3 in the frame period V4 and the frame period V5.

The measurement unit 130 executes the measurement of a subject on the basis of the image V2 and the image V4. The exposure periods of the pixels 54 of the eighth row to the tenth row in the frame period V2 do not overlap the switching period P10. The measurement unit 130 performs measurement using the pixel signals of the pixels 54 of the eighth row to the tenth row in the image V2 and the pixel signals of the pixels 54 of the eighth row to the tenth row in the image V4. The measurement unit 130 may perform measurement using the pixel signals of the pixels 54 of the eighth row and the ninth row in the image V2 and the pixel signals of the pixels 54 of the eighth row and the ninth row in the image V4.

The measurement unit 130 performs measurement using the pixel signals of the pixels 54 of a plurality of rows which are continuous. The measurement unit 130 compares two luminance profiles in units of blocks including a plurality of rows. That is, the measurement unit 130 executes block matching. Therefore, the accuracy of measurement is improved.

The measurement unit 130 may use only the pixel signals of the pixels 54 of some columns in each row. Some of the columns include a column in which the pixel 54 corresponding to the measurement coordinates is arranged.

The imaging device 110 multiplies a pixel signal by a gain in a case where a subject is dark, to thereby amplify the pixel signal. Generally, in a case where a gain becomes higher, the signal to noise (SN) ratio of a pixel becomes lower. For this reason, the accuracy of measurement decreases. In a case where the size of block matching becomes larger, a processing time increases. However, the accuracy of measurement is improved. The measurement unit 130 may control the size of block matching on the basis of a gain.

In first to eighth and tenth embodiments, the measurement unit 130 may perform measurement using the pixel signals of the pixels 54 of a plurality of rows which are continuous.

Tenth Embodiment

Figure 30:
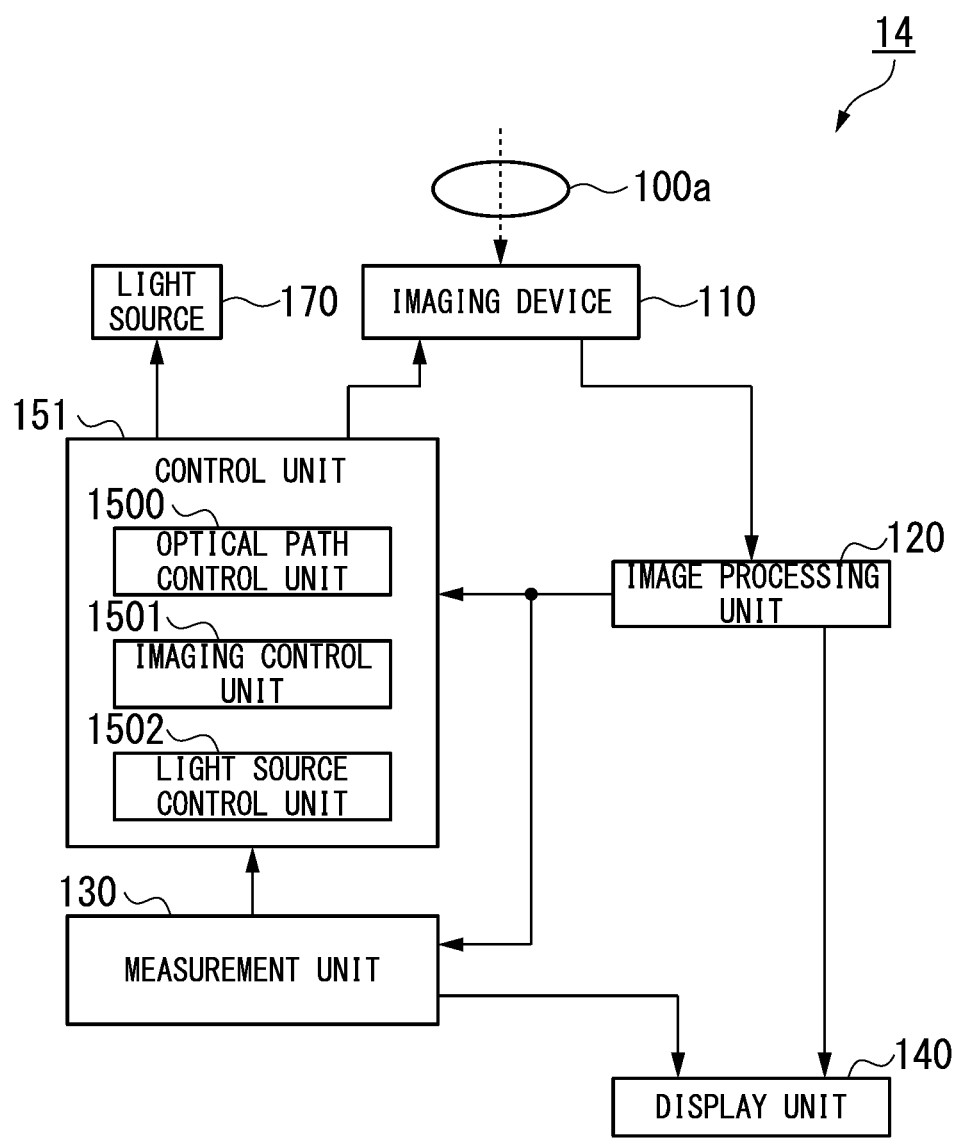
FIG. 30 is a block diagram showing a configuration of an endoscope device according to a tenth embodiment of the present invention.

FIG. 30 shows a configuration of an endoscope device 14 according to a tenth embodiment of the present invention. The same portions as portions shown in FIG. 18 will not be described. An imaging condition in the endoscope device 14 according to the tenth embodiment is different from the imaging conditions in the first to ninth embodiments.

The endoscope device 14 includes an optical system 100a instead of the optical system 100 shown in FIG. 18. The optical system 100a forms a subject image based on light reflected from a subject in the imaging region of the imaging device 110. The optical system 100a does not include the first optical system 101, the second optical system 102, and the optical path switching unit 103 which are shown in FIG. 1.

An imaging condition switching unit of the tenth embodiment includes the light source 170. The light source 170 generates white light and pattern light. The pattern light has a spatial structure in which a bright portion and a dark portion are included. The white light does not have a spatial structure in which the bright portion and the dark portion are included. The light source control unit 1502 causes the light source 170 to switch the state of the light source 170 from a first state to a second state. The first state is a state in which a subject is irradiated with the white light. The second state is a state in which a subject is irradiated with the pattern light. When the light source 170 is in the first state, the imaging device 110 operates in the first read-out mode. When the light source 170 is in the second state, the imaging device 110 operates in the second read-out mode.

A plurality of imaging conditions includes a first imaging condition, a second imaging condition, a third imaging condition, and a fourth imaging condition. The first imaging condition, the second imaging condition, the third imaging condition, and the fourth imaging condition are different from each other. When the first imaging condition is set, the light source 170 is in the first state. When any one of the second imaging condition, the third imaging condition, and the fourth imaging condition is set, the light source 170 is in the second state. The phase of the pattern light under the second imaging condition, the phase of the pattern light under the third imaging condition, and the phase of the pattern light under the fourth imaging condition are different from each other. The imaging device 110 outputs a first image, a second image, a third image, and a fourth image. When the first imaging condition is set, the imaging device 110 outputs the first image. When the second imaging condition is set, the imaging device 110 outputs the second image. When the third imaging condition is set, the imaging device 110 outputs the third image. When the fourth imaging condition is set, the imaging device 110 outputs the fourth image. The measurement unit 130 executes the measurement of a subject on the basis of the second image, the third image, and the fourth image.

For example, the light source 170 has an LED array. In the LED array, a plurality of LEDs are arranged in a matrix. The light source control unit 1502 causes the light source 170 to turn on all the LEDs of the LED array in the observation mode (first read-out mode). The light source control unit 1502 causes the light source 170 to turn on some LEDs of the LED array in a measurement G mode (second read-out mode). In the measurement G mode, the light source 170 generates illumination light having a spatial stripe pattern. In the stripe pattern, an elongated bright portion and an elongated dark portion are lined up alternately. The light source control unit 1502 controls the position of an LED to be turned on and the position of an LED to be turned off in the LED array, to thereby shift the phase of the stripe pattern. The light source 170 may include an LD and a phase shift mechanism.

Figure 31:
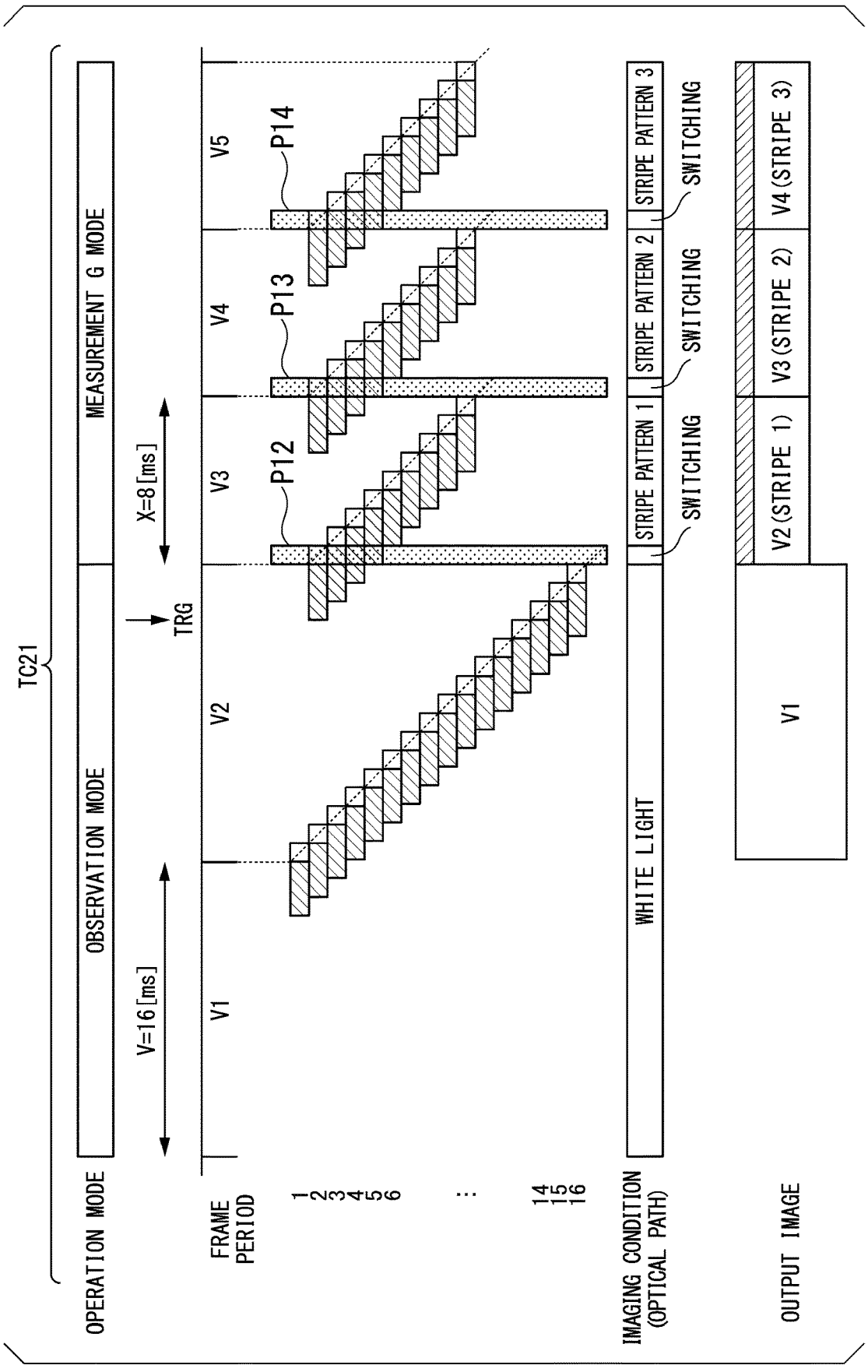
FIG. 31 is a timing chart showing an operation of an imaging device according to the tenth embodiment of the present invention.

FIG. 31 shows an operation of the imaging device 110. The operation of the imaging device 110 will be described with reference to FIG. 31. The same portions as portions shown in FIG. 4 will not be described.

A timing chart TC21 shows the operation of the imaging device 110. The imaging device 110 operates in the observation mode in the frame period V1. In the frame period V1 and the frame period V2, the imaging condition of the imaging device 110 is the first imaging condition. Therefore, the light source 170 is in the first state, and generates the white light.

In the example shown in FIG. 31, measurement coordinates are set in the sixth row of the imaging region. When the read-out period of the pixels 54 of the sixteenth row in the frame period V2 ends, the imaging control unit 1501 brings the imaging device 110 into an operation in the measurement G mode (second read-out mode). The imaging control unit 1501 outputs a command for switching the operation mode of the imaging device 110 from the observation mode to the measurement G mode to the imaging device 110. The imaging device 110 starts its operation in the measurement G mode on the basis of the command from the imaging control unit 1501. In the measurement G mode, the imaging device 110 sequentially scans nine rows, and sequentially reads out the pixel signals from the pixels 54 of each row.

The imaging control unit 1501 controls a read-out position on the basis of the position of the measurement coordinates. In the example shown in FIG. 31, the pixel 54 corresponding to the measurement coordinates is disposed in the sixth row. The imaging control unit 1501 equalizes a period in which imaging conditions are switched with a period except a predetermined period. The predetermined period includes the exposure period of a measurement row and the read-out period of the measurement row. The measurement row includes a pixel 54 corresponding to the measurement coordinates.

When the read-out period of the pixels 54 of the sixteenth row in the frame period V2 ends, the read-out period of the pixels 54 of the second row in the frame period V3 is started. At this moment, switching between imaging conditions, that is, switching between the states of the light source 170 is started. The light source control unit 1502 starts switching from the first state to the second state.

The imaging control unit 1501 causes the imaging device 110 to read out the pixel signals from the pixels 54 of the second row in a switching period P12. When the read-out period of the pixels 54 of the second row in the frame period V3 ends, switching between imaging conditions, that is, switching between the states of the light source 170 is completed. At this moment, the light source 170 is in the second state, and generates pattern light of a stripe pattern 1. Thereafter, the imaging device 110 sequentially starts the read-out periods of the pixels 54 of the third row to the tenth row, and sequentially reads out the pixel signals of the pixels 54 of the third row to the tenth row.

The length of the switching period P12 is shorter than the length of the exposure period of the measurement row. Before the exposure period of the pixels 54 of the measurement row is started, the switching between imaging conditions is completed. In the example shown in FIG. 31, when the switching between imaging conditions is completed, the exposure period of the pixels 54 of the sixth row in the frame period V3 is started.

The imaging device 110 may read out the pixel signals of the pixels 54 of the first row to the tenth row in the measurement G mode. In that case, the switching period P12 may be the same as the read-out period of the pixels 54 of the first row. The imaging device 110 may not read out the pixel signals of the pixels 54 of rows below the measurement row in the measurement G mode. That is, the imaging device 110 may not read out the pixel signals from the pixels 54 of at least one row of the seventh row to the tenth row. The switching period P12 may be the same as the read-out period of the pixels 54 of any one row of the sixth row to the tenth row.

When the read-out period of the pixels 54 of the tenth row in the frame period V3 ends, the read-out period of the pixels 54 of the second row in the frame period V4 is started. At this moment, switching between imaging conditions, that is, switching between the states of the light source 170 is started. The light source control unit 1502 starts switching between the phases of stripe patterns generated by the light source 170.

The imaging control unit 1501 causes the imaging device 110 to read out the pixel signals from the pixels 54 of the second row in a switching period P13. When the read-out period of the pixels 54 of the second row in the frame period V4 ends, switching between imaging conditions, that is, switching between the states of the light source 170 is completed. At this moment, the light source 170 is in the second state, and generates pattern light of a stripe pattern 2. The stripe pattern 2 has a phase different from the phase of the stripe pattern 1. Thereafter, the imaging device 110 sequentially starts the read-out periods of the pixels 54 of the third row to the tenth row, and sequentially reads out the pixel signals of the pixels 54 of the third row to the tenth row.

When the read-out period of the pixels 54 of the tenth row in the frame period V4 ends, the read-out period of the pixels 54 of the second row in the frame period V5 is started. At this moment, switching between imaging conditions, that is, switching between the states of the light source 170 is started. The light source control unit 1502 starts switching between the phases of stripe patterns generated by the light source 170.

The imaging control unit 1501 causes the imaging device 110 to read out a pixel signal from the pixels 54 of the second row in a switching period P14. When the read-out period of the pixels 54 of the second row in the frame period V5 ends, switching between imaging conditions, that is, switching between the states of the light source 170 is completed. At this moment, the light source 170 is in the second state, and generates pattern light of a stripe pattern 3. The stripe pattern 3 has a phase different from both the phase of the stripe pattern 1 and the phase of the stripe pattern 2. Thereafter, the imaging device 110 sequentially starts the read-out periods of the pixels 54 of the third row to the tenth row, and sequentially reads out the pixel signals of the pixels 54 of the third row to the tenth row.

In the measurement G mode, pixel signals are not read out from the pixels 54 of the first row and the eleventh row to the sixteenth row. After the imaging device 110 starts its operation in the measurement G mode, the imaging control unit 1501 causes the imaging device 110 to stop reading out the pixel signals from the pixels 54 of rows other than rows to be read out. The rows to be read out are the second row to the tenth row. In FIG. 31, the exposure periods of the pixels 54 of rows other than the rows to be read out are not shown.

In FIG. 31, an image (output image) which is output from the imaging device 110 is schematically shown. An image V1 includes the pixel signals which are read out from the pixels 54 of sixteen rows after the exposure period in the frame period V1. The image V1 includes the pixel signals which are read out in the observation mode by the imaging device 110. An image V2 (stripe 1) includes the pixel signals which are read out from the pixels 54 of nine rows after the exposure period in the frame period V2. The image V2 (stripe 1) includes the pixel signals which are read out in the measurement G mode by the imaging device 110. The sizes of an image V3 (stripe 2) and an image V4 (stripe 3) are the same as the size of the image V2 (stripe 1).

The control unit 150 causes the measurement unit 130 to execute measurement in which the image V2 (stripe 1), the image V3 (stripe 2), and the image V4 (stripe 3) are used. The measurement unit 130 executes the measurement of a subject on the basis of the image V2 (stripe 1), the image V3 (stripe 2), and the image V4 (stripe 3). Measurement based on three images having phases different from each other is a known technique. The imaging device 110 may output more than three images in the measurement G mode. The more than three images have phases different from each other. The measurement unit 130 may execute measurement on the basis of the more than three images.

An interval between a first timing and a second timing is eight milliseconds. The first timing is a timing at which the imaging device 110 acquires the image V2 (stripe 1). The second timing is a timing at which the imaging device 110 acquires the image V3 (stripe 2). The imaging device 110 acquires an image every eight milliseconds in the measurement G mode.

In the frame period V2, the pixels 54 of the second row to the fourth row are irradiated with the white light. The exposure periods of the pixels 54 of the second row to the fifth row in the frame period V2 overlap the switching period P12. In the image V2 (stripe 1), the pixel signals of the pixels 54 of the sixth row to the tenth row can be used in measurement, the pixel signals of the pixels 54 of the second row to the fifth row are not suitable for measurement. Similarly, in the image V3 (stripe 2) and the image V4 (stripe 3), the pixel signals of the pixels 54 of the sixth row to the tenth row can be used in measurement, but the pixel signals of the pixels 54 of the second row to the fifth row are not suitable for measurement.

The imaging device 110 reads out the pixel signals from the pixels 54 of at least one row including the measurement row in the measurement G mode. The measurement row includes a pixel 54 corresponding to the measurement coordinates. The imaging device 110 may not read out the pixel signals from the pixels 54 of at least one row of the seventh row to the tenth row in the measurement G mode.

Rows in which the imaging device 110 reads out the pixel signals in the measurement G mode are not limited to the second row to the tenth row. The rows in which the imaging device 110 reads out the pixel signals in the measurement G mode only have to include the measurement row.

The lengths of the switching period P12, the switching period P13, and the switching period P14 are based on the response time of the light source 170. In a case where the response of the light source 170 is rapid, the switching period P12, the switching period P13, and the switching period P14 may be shorter than the read-out period of one row.

When the imaging device 110 operates in the measurement G mode, the light source control unit 1502 may set the amount of light of the light source 170 to be larger than the amount of light in the observation mode. That is, the light source control unit 1502 may turn on the light source 170 to be brighter than in the observation mode. Thereby, an image acquired in the measurement G mode increases in brightness.

Figure 32:
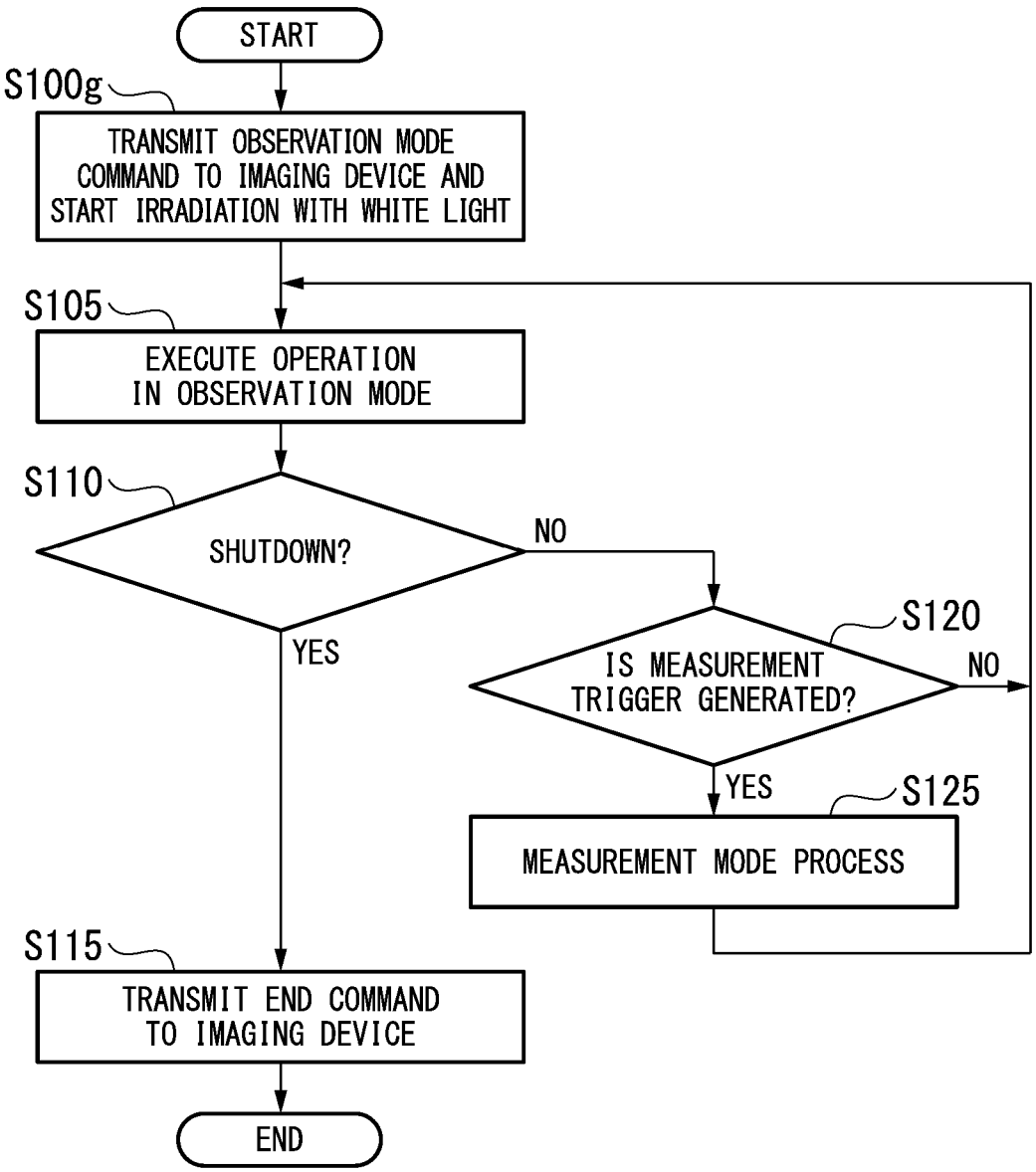
FIG. 32 is a flow chart showing a procedure of operations of the endoscope device according to the tenth embodiment of the present invention.

FIG. 32 shows a procedure of operations of the endoscope device 14. The operation of the endoscope device 14 will be described with reference to FIG. 32. The same process as the process shown in FIG. 6 will not be described.

When the endoscope device 14 starts up, the endoscope device 14 operates in the observation mode. The imaging control unit 1501 transmits the observation mode command to the imaging device 110. Thereby, the imaging control unit 1501 brings the imaging device 110 into an operation in the observation mode. The light source control unit 1502 causes the light source 170 to start irradiation with the white light (step S100g). After step S100g, the process in step S105 is executed.

Figure 33:
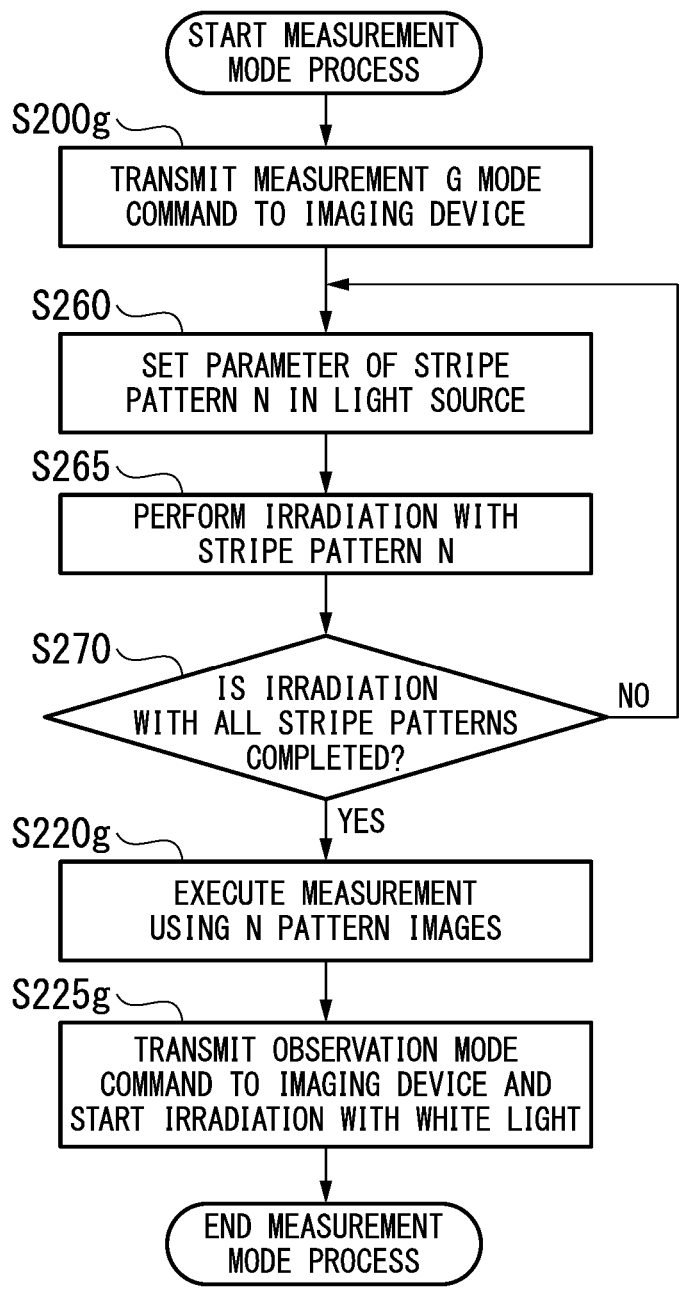
FIG. 33 is a flow chart showing a procedure of operations of the endoscope device according to the tenth embodiment of the present invention.

FIG. 33 shows the details of the measurement mode process. The operation of the endoscope device 14 in the measurement mode process will be described with reference to FIG. 33. The same process as the process shown in FIG. 7 will not be described.

The imaging control unit 1501 transmits a measurement G mode command to the imaging device 110. Thereby, the imaging control unit 1501 brings the imaging device 110 into an operation in the measurement G mode (step S200g).

After step S200g, the imaging device 110 starts its operation in the measurement G mode on the basis of the measurement G mode command The light source control unit 1502 sets parameters of a stripe pattern n in the light source 170 (step S260). The number n is a natural number. For example, the number n is any one of 1 to 3.

After step S260, the light source control unit 1502 causes the light source 170 to perform irradiation with pattern light of the stripe pattern n. The light source 170 generates the pattern light of the stripe pattern n, and irradiates a subject with the generated pattern light (step S265).

After step S265, the control unit 150 determines whether irradiation with all the stripe patterns has been completed (step S270). In step S270, in a case where the control unit 150 determined that the irradiation with the stripe patterns is not completed, the process in step S260 is executed.

In step S270, in a case where the control unit 150 determined that the irradiation with all the stripe patterns has been completed, the control unit 150 causes the measurement unit 130 to execute measurement in which an image corresponding to each of n stripe patterns is used. The measurement unit 130 executes the measurement of a subject on the basis of the images which are output from the image processing unit 120. The display unit 140 displays a measurement result (step S220g).

After step S220g, the imaging control unit 1501 transmits the observation mode command to the imaging device 110. Thereby, the imaging control unit 1501 brings the imaging device 110 into an operation in the observation mode. The light source control unit 1502 causes the light source 170 to start irradiation with the white light (step S225g). At this moment, the measurement mode process ends. After the measurement mode process ends, the process in step S105 is executed.

The operation shown in FIG. 31, an interval in which three images for measurement are acquired is eight milliseconds. The endoscope device 14 can shorten the time interval of imaging under a plurality of imaging conditions. Therefore, an interval in which three images for measurement are acquired becomes shorter. A blur between three images used in measurement is reduced, and a measurement error caused by the influence of the blur decreases. That is, the accuracy of measurement is improved.

Addition

According to an aspect of the present invention, there is provided a method of operating an endoscope device including a first step, a second step, and a third step. The endoscope device including an imaging device, an imaging condition switching unit, a measurement unit, and a control unit. The imaging device includes a plurality of pixels arranged in a matrix. The imaging device generates a pixel signal of each pixel based on an optical image of a subject in each frame period of a plurality of frame periods. The imaging device outputs an image in each frame period of the plurality of frame periods. The imaging device continuously scans all or some of a plurality of rows in an array of the plurality of pixels, for each row, in each frame period of the plurality of frame periods. The imaging device reads out the pixel signals from the pixels in all or some of the plurality of rows. The image is generated on the basis of the pixel signals generated in at least some of the plurality of pixels. The imaging condition switching unit switches between a plurality of imaging conditions so that the imaging device captures an image of the subject. The measurement unit executes measurement of the subject in measurement coordinates within the image on the basis of the images for at least two frame periods. The imaging device reads out the pixel signals from the pixels in all or some of the plurality of rows in a first time in a first read-out mode. The imaging device reads out the pixel signals from the pixels in all or some of the plurality of rows in a second time in a second read-out mode. The second time is shorter than the first time. The control unit brings the imaging device into an operation in the first read-out mode in the first step before an instruction for the measurement of the subject is generated. The control unit brings the imaging device into an operation in the second read-out mode in the second step after the instruction for the measurement of the subject is generated. The control unit causes the imaging condition switching unit to switch the imaging conditions in the third step on the basis of an operation of the imaging device in the second read-out mode. The imaging device operates in the second read-out mode while the imaging condition switching unit switches the imaging conditions.

According to an aspect of the present invention, there is provided a program for causing a processor of an endoscope device to execute a first step, a second step, and a third step. The endoscope device includes the imaging device, the imaging condition switching unit, the measurement unit, and the processor. The imaging device reads out the pixel signals from the pixels in all or some of the plurality of rows in a first time in a first read-out mode. The imaging device reads out the pixel signals from the pixels in all or some of the plurality of rows in a second time in a second read-out mode. The second time is shorter than the first time. The processor brings the imaging device into an operation in the first read-out mode in the first step before an instruction for the measurement of the subject is generated. The processor brings the imaging device into an operation in the second read-out mode in the second step after the instruction for the measurement of the subject is generated. The processor causes the imaging condition switching unit to switch the imaging conditions in the third step on the basis of an operation of the imaging device in the second read-out mode. The imaging device operates in the second read-out mode while the imaging condition switching unit switches the imaging conditions.

According to an aspect of the present invention, there is provided a computer readable non-transitory recording medium having a program recorded therein, the program causing a processor of an endoscope device to execute a first step, a second step, and a third step. The endoscope device includes the imaging device, the imaging condition switching unit, the measurement unit, and the processor. The imaging device reads out the pixel signals from the pixels in all or some of the plurality of rows in a first time in a first read-out mode. The imaging device reads out the pixel signals from the pixels in all or some of the plurality of rows in a second time in a second read-out mode. The second time is shorter than the first time. The processor brings the imaging device into an operation in the first read-out mode in the first step before an instruction for the measurement of the subject is generated. The processor brings the imaging device into an operation in the second read-out mode in the second step after the instruction for the measurement of the subject is generated. The processor causes the imaging condition switching unit to switch the imaging conditions in the third step on the basis of an operation of the imaging device in the second read-out mode. The imaging device operates in the second read-out mode while the imaging condition switching unit switches the imaging conditions.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:
1. An endoscope device comprising:
an imaging device that includes a plurality of pixels arranged in a matrix, generates a pixel signal of each pixel based on an optical image of a subject in each frame period of a plurality of frame periods, outputs an image in each frame period of the plurality of frame periods, continuously scans all or some of a plurality of rows in an array of the plurality of pixels, for each row, in each frame period of the plurality of frame periods, and reads out the pixel signals from the pixels in all or some of the plurality of rows, the image being generated on the basis of the pixel signals generated in at least some of the plurality of pixels;
an imaging condition switching unit that switches between a plurality of imaging conditions so that the imaging device captures an image of the subject;
a measurement unit that executes measurement of the subject in measurement coordinates within the image on the basis of the images for at least two frame periods; and
a control unit,
wherein the imaging device reads out the pixel signals from the pixels in all or some of the plurality of rows in a first time in a first read-out mode,
the imaging device reads out the pixel signals from the pixels in all or some of the plurality of rows in a second time in a second read-out mode, the second time being shorter than the first time,
the control unit brings the imaging device into an operation in the first read-out mode before an instruction for the measurement of the subject is generated,
the control unit brings the imaging device into an operation in the second read-out mode after the instruction for the measurement of the subject is generated,
the control unit causes the imaging condition switching unit to switch the imaging conditions on the basis of an operation of the imaging device in the second read-out mode, and
the imaging device operates in the second read-out mode while the imaging condition switching unit switches the imaging conditions.

2. The endoscope device according to claim 1,
wherein a first size of the image is larger than a second size of the image,
the first size is a size of the image based on the pixel signals which are read out in the first read-out mode by the imaging device, and
the second size is a size of the image based on the pixel signals which are read out in the second read-out mode by the imaging device.

3. The endoscope device according to claim 2,
wherein the control unit controls a read-out position on the basis of a position of the measurement coordinates, and
the read-out position is a position of a row in which the imaging device reads out the pixel signals in the second read-out mode.

4. The endoscope device according to claim 3,
wherein a first row number is larger than a second row number,
the first row number is the number of rows in which the imaging device reads out the pixel signals in the first read-out mode, and
the second row number is the number of rows in which the imaging device reads out the pixel signals in the second read-out mode.

5. The endoscope device according to claim 3,
wherein the control unit controls a column number on the basis of the position of the measurement coordinates, and
the column number is the number of columns in which the imaging device reads out the pixel signals in the second read-out mode.

6. The endoscope device according to claim 5,
wherein a first column number is larger than a second column number,
the first column number is the number of columns in which the imaging device reads out the pixel signals in the first read-out mode, and
the second column number is the number of columns in which the imaging device reads out the pixel signals in the second read-out mode.

7. The endoscope device according to claim 3,
wherein the imaging device reads out the pixel signals from the pixels disposed in a measurement row in the second read-out mode, and the measurement row includes the pixel corresponding to the measurement coordinates.

8. The endoscope device according to claim 7,
wherein when the imaging device reads out the pixel signals from the pixels disposed in the measurement row in the second read-out mode, the control unit causes the imaging condition switching unit to switch the imaging conditions.

9. The endoscope device according to claim 1,
wherein a time period in which the pixel signals are read out from the pixels in each row of the plurality of rows includes a blanking time,
the blanking time is a time period from a timing at which read-out of the pixel signal is completed in one row to a timing at which read-out of the pixel signal is started in a row different from the one row, and
the blanking time when the imaging device reads out the pixel signals in the second read-out mode is shorter than the blanking time when the imaging device reads out the pixel signals in the first read-out mode.

10. The endoscope device according to claim 1,
wherein the control unit equalizes brightnesses of the images for at least two frame periods used in the measurement of the subject by the measurement unit.

11. The endoscope device according to claim 1,
wherein the measurement unit executes the measurement on the basis of a first image and a second image,
the first image is generated on the basis of the pixel signals of the pixels exposed in a first exposure period,
the second image is generated on the basis of the pixel signals of the pixels exposed in a second exposure period,
the first exposure period includes a timing at which the instruction for the measurement of the subject is generated,
the second exposure period is started after the imaging condition switching unit completes the switching between imaging conditions, and
the control unit equalizes a length of the first exposure period with a length of the second exposure period on the basis of the length of the second exposure period determined in advance.

12. The endoscope device according to claim 1,
wherein the measurement unit executes the measurement on the basis of a first image and a second image,
the first image is generated on the basis of the pixel signals of the pixels exposed in a first exposure period,
the second image is generated on the basis of the pixel signals of the pixels exposed in a second exposure period,
the first exposure period includes a timing at which the instruction for the measurement of the subject is generated,
the second exposure period is started after the imaging condition switching unit completes the switching between imaging conditions, and
the control unit equalizes a length of the second exposure period with a length of the first exposure period on the basis of the length of the first exposure period.

13. The endoscope device according to claim 1, further comprising a light source that generates illumination light with which the subject is irradiated,
wherein the measurement unit executes the measurement on the basis of a first image and a second image,
the first image is generated on the basis of the pixel signals of the pixels exposed in a first exposure period,
the second image is generated on the basis of the pixel signals of the pixels exposed in a second exposure period,
the first exposure period includes a timing at which the instruction for the measurement of the subject is generated,
the second exposure period is started after the imaging condition switching unit completes the switching between imaging conditions,
the light source generates the illumination light in the first exposure period and the second exposure period, and
the control unit controls the amount of light of the light source in the second exposure period on the basis of brightness of the first image.

14. The endoscope device according to claim 1,
wherein the control unit controls a row number on the basis of an estimated time,
the estimated time is a time period estimated in the switching between imaging conditions by the imaging condition switching unit, and
the row number is the number of rows in which the imaging device reads out the pixel signals in the second read-out mode.

15. The endoscope device according to claim 14, further comprising a temperature detection unit that detects a temperature of the imaging condition switching unit,
wherein the control unit controls the row number on the basis of the temperature detected by the temperature detection unit.

16. The endoscope device according to claim 1,
wherein the plurality of imaging conditions include a first imaging condition and a second imaging condition,
the first imaging condition and the second imaging condition are different from each other,
the control unit controls a third row number on the basis of a first estimated time,
the first estimated time is a time period estimated in the switching between imaging conditions from the first imaging condition to the second imaging condition by the imaging condition switching unit,
the third row number is the number of rows in which the imaging device reads out the pixel signals in the second read-out mode,
the control unit controls a fourth row number on the basis of a second estimated time,
the second estimated time is a time period estimated in the switching between imaging conditions from the second imaging condition to the first imaging condition by the imaging condition switching unit, and
the fourth row number is the number of rows in which the imaging device reads out the pixel signals in the second read-out mode.

17. The endoscope device according to claim 1,
wherein the measurement unit executes the measurement on the basis of the pixel signals of a measurement row in the image,
the measurement row includes at least two rows which are continuous, and
any one of the at least two rows includes the pixel corresponding to the measurement coordinates.

18. The endoscope device according to claim 1,
wherein the imaging condition switching unit sets any one of a first optical path and a second optical path as an imaging optical path, to form only any one of a first optical image of the subject and a second optical image of the subject in an imaging region of the imaging device.

19. The endoscope device according to claim 1,
wherein the imaging condition switching unit includes a light source that generates white light and pattern light, the pattern light having a spatial structure in which a bright portion and a dark portion are included,
the control unit causes the imaging condition switching unit to switch a state of the light source from a first state to a second state,
the first state is a state in which the subject is irradiated with the white light,
the second state is a state in which the subject is irradiated with the pattern light,
the imaging device operates in the first read-out mode when the light source is in the first state, and
the imaging device operates in the second read-out mode when the light source is in the second state.

20. The endoscope device according to claim 1,
wherein the images of the at least two frame periods are generated on the basis of the pixel signals which are read out in the second read-out mode by the imaging device.

* * * * *